(12) United States Patent
Isacoff et al.

(10) Patent No.: US 10,745,453 B2
(45) Date of Patent: Aug. 18, 2020

(54) COMPOSITIONS AND METHODS FOR ENHANCING VISUAL FUNCTION

(71) Applicant: The Regents of the University of California, Oakland, CA (US)

(72) Inventors: Ehud Y. Isacoff, Berkeley, CA (US); Michael H. Berry, Berkeley, CA (US); Amy Holt, Berkeley, CA (US); Meike Visel, El Cerrito, CA (US); Autoosa Salari, Berkeley, CA (US); John G. Flannery, Berkeley, CA (US); Benjamin M. Gaub, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/279,576

(22) Filed: Feb. 19, 2019

(65) Prior Publication Data

US 2019/0169244 A1 Jun. 6, 2019

Related U.S. Application Data

(63) Continuation of application No. PCT/US2018/060669, filed on Nov. 13, 2018.

(60) Provisional application No. 62/641,783, filed on Mar. 12, 2018, provisional application No. 62/589,476, filed on Nov. 21, 2017, provisional application No. 62/585,237, filed on Nov. 13, 2017.

(51) Int. Cl.
| | | |
|---|---|---|
| *A61K 48/00* | (2006.01) | |
| *C07K 14/47* | (2006.01) | |
| *C12N 15/864* | (2006.01) | |
| *C12N 5/10* | (2006.01) | |
| *A61P 27/04* | (2006.01) | |
| *C12N 15/85* | (2006.01) | |
| *A61K 9/00* | (2006.01) | |
| *A61K 9/51* | (2006.01) | |
| *A61K 38/00* | (2006.01) | |

(52) U.S. Cl.
CPC ............ *C07K 14/47* (2013.01); *A61K 9/0019* (2013.01); *A61K 9/0048* (2013.01); *A61K 9/5138* (2013.01); *A61K 9/5153* (2013.01); *A61K 48/0058* (2013.01); *A61K 48/0075* (2013.01); *A61K 48/0083* (2013.01); *A61P 27/04* (2018.01); *C12N 15/85* (2013.01); *A61K 38/00* (2013.01); *C12N 2750/14143* (2013.01)

(58) Field of Classification Search
None
See application file for complete search history.

(56) References Cited

U.S. PATENT DOCUMENTS

| | | |
|---|---|---|
| 2003/0113798 A1 | 6/2003 | Burmer et al. |
| 2012/0172419 A1* | 7/2012 | Neitz .................. A61B 5/0496 514/44 R |
| 2014/0171376 A1 | 6/2014 | Van Wyk et al. |
| 2016/0015288 A1 | 1/2016 | Neitz et al. |
| 2016/0361437 A1 | 12/2016 | Lucas et al. |

FOREIGN PATENT DOCUMENTS

| | | |
|---|---|---|
| WO | 2015142941 | 9/2015 |
| WO | 2017055421 | 4/2017 |
| WO | 2018134168 | 7/2018 |

OTHER PUBLICATIONS

Ferguson et al, Systemic Delivery of Oncolytic Viruses: Hopes and Hurdles, Advances in Virology vol. 2012, pp. 1-14.*
Yang et al, Virus-Mediated Transduction of Murine Retina with Adeno-Associated Virus: Effects of Viral Capsid and Genome Size, Journal of Virology, Aug. 2002, p. 7651-7660.*
Carleton et al, Rod and Cone Opsin Families Differ in Spectral Tuning Domains but Not Signal Transducing Domains as Judged by Saturated Evolutionary Trace Analysis, J Mol Evol (2005) 61:75-89.*
De Silva et al. (2017) "Long-term restoration of visual function in end-stage retinal degeneration using subretinal human melanopsin gene therapy" Proceedings of the National Academy of Sciences, 114(42):11211-11216.
Gaub et al. (2015) "Optogenetic Vision Restoration Using Rhodopsin for Enhanced Sensitivity" Molecular Therapy, 23(10)1562-1571.
Imai, et al.; "Single amino acid residue as a functional determinant of rod and cone visual pigments"; PNAS; vol. 94, pp. 2322-2326 (Mar. 1997).
Insinna, et al.; "An S-Opsin Knock-In Mouse (F81Y) Reveals a Role for the Native Ligand 11-cis-Retinal in Cone Opsin Biosynthesis"; The Journal of Neuroscience; vol. 32, No. 23, pp. 8094-8104 (Jun. 6, 2012).
Kefalov, et al.; "Role of visual pigment properties in rod and cone phototransduction"; Nature; vol. 425, No. 6957, pp. 526-531 (Oct. 2, 2003).
Kefalov, et al.; "Breaking the Covalent Bond—A Pigment Property that Contributes to Desensitization in Cones"; Neuron; vol. 46, No. 6, pp. 879-890 (Jun. 16, 2005).
Masseck, et al.; "Vertebrate Cone Opsins Enable Sustained and Highly Sensitive Rapid Control of $G_{i/o}$ Signaling in Anxiety Circuitry"; Neuron; vol. 81, pp. 1263-1273 (Mar. 19, 2014).
Nathans, et al.; "Molecular Genetics of Human Color Vision: The Genes Encoding Blue, Green and Red Pigments"; Science; vol. 232; pp. 193-202 (Apr. 11, 1986).

(Continued)

*Primary Examiner* — Maria Marvich
(74) *Attorney, Agent, or Firm* — Bozicevic Field & Francis, LLP; Paula A. Borden

(57) ABSTRACT

The present disclosure provides a method of restoring or enhancing visual function in an individual, the method comprising administering to the individual a nucleic acid comprising a nucleotide sequence encoding one or more of a medium wavelength cone opsin (MW-opsin), a long wavelength cone opsin (LW-opsin), and a short wavelength cone opsin (SW-opsin). One or more of the MW-opsin, LW-opsin, and SW-opsin is expressed in a retinal cell in the individual, thereby restoring or enhancing visual function.

26 Claims, 23 Drawing Sheets

Specification includes a Sequence Listing.

(56) References Cited

OTHER PUBLICATIONS

Shi, et al.; "Signaling Properties of a Short-Wave Cone Visual Pigment and Its Role in Phototransduction"; The Journal of Neuroscience; vol. 27, No. 38, pp. 10084-10093 (Sep. 19, 2007).
Solomon, et al.; "The machinery of colour vision"; vol. 8, pp. 276-286 (Apr. 2007).
Terakita; "The opsins"; Genome Biology; vol. 6, No. 213, 9 pages (2005).
Kelley, et al.; "DNA nanoparticles are safe and nontoxic in non-human primate eyes"; International Journal of Nanomedicine; vol. 13, pp. 1361-1379 (2018).
Patel, et al.; "Lipid nanoparticles for delivery of messenger RNA to the back of the eye"; Journal of Controlled Release; vol. 303, pp. 91-100 (2019).
Wang, et al.; "Nanoparticles as Delivery Vehicles for the Treatment of Retinal Degenerative Diseases"; Adv. Exp. Med. Biol.; vol. 1074, pp. 117-123 (2018).
Li, et al.; "Cone-specific expression using a human red opsin promoter in recombinant AAV"; Vision Research; vol. 48, pp. 332-338 (2008).
Mancuso, et al.; "Gene therapy for red-green colour blindness in adult primates"; Nature; vol. 461, pp. 784-787 (Oct. 8, 2009).

\* cited by examiner

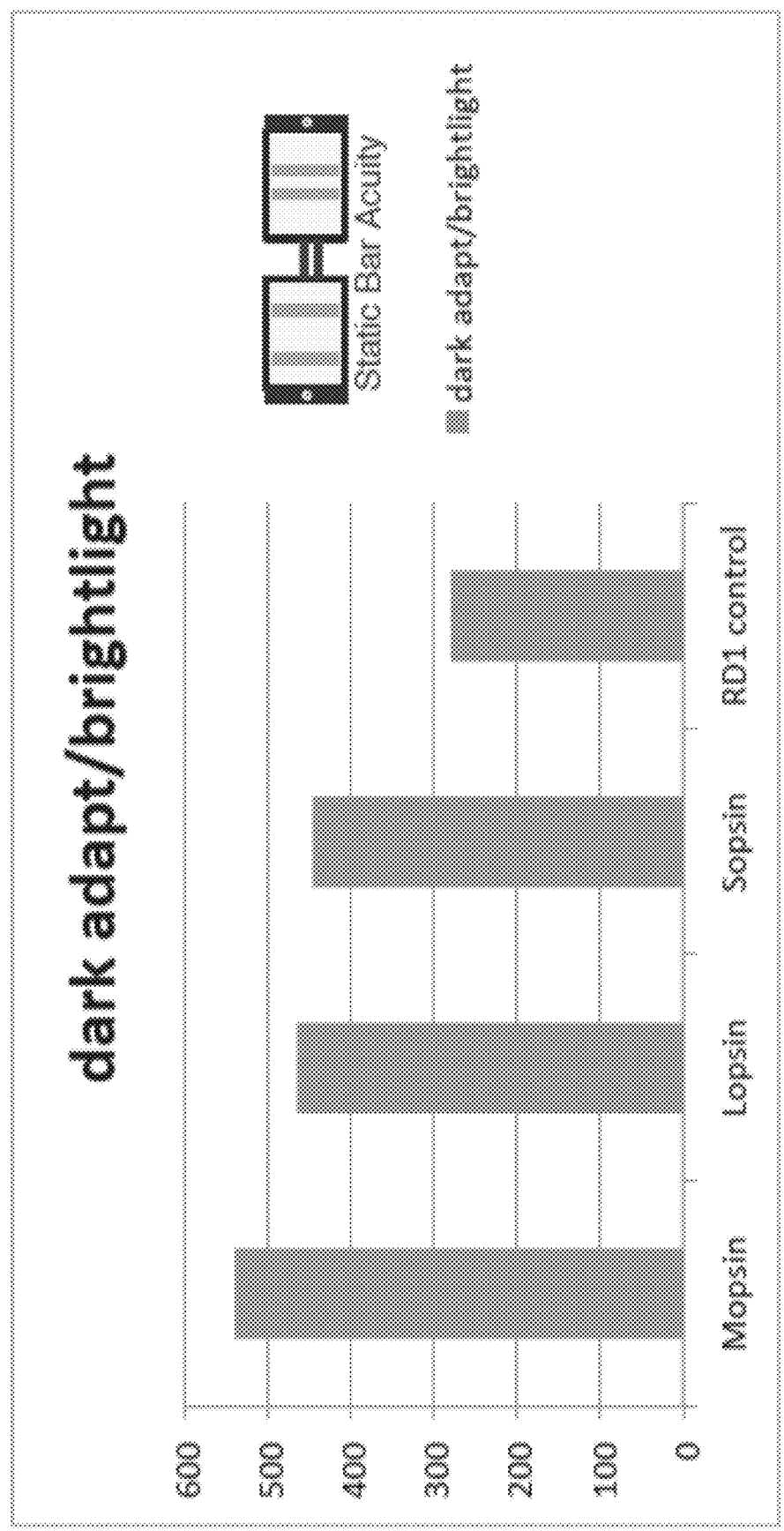
FIG. 6 Learned pattern discrimination of parallel bars at different distances (1 vs 6 cm) in *rd1* mice expressing either MW-opsin, LW-opsin or SW-opsin in RGCs, compared to untreated *rd1* control. Proportion of time spent avoiding pattern paired with shock.

FIG. 11 (Table 1)

| Light dark avoidance - white light | Fisher's exact test (one sided) | Significance? |
|---|---|---|
| *rd1* control vs *rd1* mw-opsin | 0.048 | Yes |
| *rd1* control vs *wt* | 0.048 | Yes |
| *rd1* rhodopsin vs *rd1* mw-opsin | 0.545 | No |
| *rd1* rhodopsin vs *wt* | 0.545 | No |
| *rd1* mw-opsin vs *wt* | N/A | No |

| Light dark avoidance - color | Fisher's exact test (one sided) | Significance? |
|---|---|---|
| *rd1* control - green vs *rd1* control - blue | 0.778 | No |
| rd1control - green vs rd1 rhodopsin - blue | 0.024 | Yes |
| rd1control - green vs rd1 mw opsin - blue | 0.722 | No |
| rd1 control - blue vs. rd1 rhodopsin - green | 0.103 | No |
| rd1 control - blue vs rd1 rhodopsin - blue | 0.024 | Yes |
| rd1 control blue vs rd1 mw opsin - green | 0.103 | No |
| rd1 control blue vs rd1 mw opsin - blue | 0.722 | No |
| rd1 rhodopsin - green vs rd1 mw opsin - green | 0.778 | No |
| rd1 rhodopsin - blue vs rd1 mw opsin - green | 0.5 | No |
| rd1 rhodopsin - blue vs rd1 mw opsin - blue | 0.048 | Yes |
| rd1 mw opsin - green vs rd1 mw opsin - blue | 0.167 | No |

| Light dark avoidance - white | Fisher's exact test (one sided) | Significance? |
|---|---|---|
| *rd1* control vs *rd1* rhodopsin | 0.119 | No |
| *rd1* control vs *rd1* mw-opsin | 0.048 | Yes |
| *rd1* control vs *wt* | 0.048 | Yes |

| Horizontal vs. vertical parallel bars | Pearson's Chi-Square Test (2-sided) | Fisher's exact test (one sided) | Significance? |
|---|---|---|---|
| *rd1* control vs *rd1* mw-opsin | 0.001 | 0.002 | Yes |
| rd1 control vs rd1 rhodopsin | 0.522 | 0.5 | No |
| *rd1* mw-opsin vs *rd1* rhodopsin | 0.005 | 0.01 | Yes |
| *rd1* mw-opsin vs wt | | 0.313 | No |
| *rd1* rhodopsin vs wt | | 0.249 | No |

| parallel bars static | Pearson's Chi-Square Test (2-sided) | Fisher's exact test (one sided) | Significance? |
|---|---|---|---|
| rd1 control vs rd1 mw opsin | 0.001 | 0.003 | Yes |
| rd1 control vs wt | 0.006 | 0.015 | Yes |
| rd1 mw opsin vs wt | | N/A | No |

| moving bars | Pearson's Chi-Square Test (2-sided) | Fisher's exact test (one sided) | Significance? |
|---|---|---|---|
| rd1 control vs rd1 mw opsin | 0.001 | 0.001 | Yes |
| rd1 control vs wt | <0.001 | <0.001 | Yes |
| rd1 mw opsin vs wt | | N/A | No |

| Adaptation - Light dark avoidance | | Fisher's exact test (one sided) | Significance? |
|---|---|---|---|
| *rd1* control - green vs *rd1* mw-opsin light adapted, indoor | | 0.278 | No |
| *rd1* control - green vs *rd1* mw-opsin light adapted, outdoor | | 0.047 | Yes |
| *rd1* control - green vs *rd1* mw-opsin dark adapted, indoor | | 0.013 | Yes |
| | Pearson's Chi-Square Test (2-sided) | Fisher's exact test (one sided) | |
| rd1 mw-opsin -light adapted, indoor stimuli vs dark adapted, indoor | 0.033 | 0.045 | Yes |

| adaptation - parallel bars | Fisher's exact test (one sided) | Significance? |
|---|---|---|
| rd1 control vs rd1 mw-opsin light adapted, dim indoor | 0.121 | No |
| rd1 control vs rd1 mw-opsin light adapted, indoor | 0.01 | Yes |
| rd1 control vs rd1 mw-opsin dark adapted, dim indoor | 0.007 | Yes |
| rd1 control vs rd1 mw-opsin dark adapted, indoor | 0.007 | Yes |
| rd1 control vs rd1 mw-opsin dark adapted, dim indoor | 0.007 | Yes |
| rd1 control vs rd1 mw-opsin dark adapted, indoor | 0.007 | Yes |

FIG. 12A

```
Hu        6  EEEFYLFKNISSVGPWDGPQYHIAPVWAFYLQAAFMGTVFLLIGFPLNAMVLVATLRYKKL  65
Mo        4  EDDFYLFQNISSVGPWDGPQYHLAPVWAFRLQAAFMGEVFFVGTPLNAIVLVATLHYKKL   63
Chimera      EDDFYLFQNISSVGPWDGPQYHLAPVWAFYLQAAFMGTVFLLIGFPLNAMVLVATLHYKKL Hu       66  RQPLNYILVNVSFGGFLLLCIFSVFPVFVASCNGYFVFGRHVCALEGFLGTVAGLVTGWSL  125
Mo       64  RQPLNYILVNVSLGGFLFCIFSVFTVFIASCHGYFLFGRHVCALEAFLGSVAGLVTGWSL   123
Chimera      RQPLNYILVNVSFGGFLLLCIFSVFPVFVASCNGYFVFGRHVCALEGFLGTVAGLVTGWSL Hu      126  AFLAFERYIVICKPFGNFRFSSKHALTVVLATWTIGIGVSIPPFFGWSRFIPEGLQCSCG  185
Mo      124  AFLAFERYVVICKPFGSIRFNSKHALMVVLATWIIGIGVSIPPFFGWSRFIPEGLQCSCG  183
Chimera      AFLAFERYVVICKPFGSIRFNSKHALTVVLATWTIGIGVSIPPFFGWSRFIPEGLQCSCG Hu      186  PDWYTVGTKYRSESYTWFLFIFCFIVPLSLICFSYTQLLRALKAVAAQQQESATTQKAER  245
Mo      184  PDWYTVGTKYRSEYTWFLFIECFIIPLSLICFSYSQLLRTLRAVAAQQQESATTQKAER   243
Chimera      PDWYTVGTKYRSESYTWFLFIECFIVPLSLICFSYTQLLRALRAVAAQQQESATTQKAER Hu      246  EVSRMVVVMVGSFCVCYVPYAAFAMYMVNNRNHGLDLRLVTIPSFFSKSACTYNPIIYCF  305
Mo      244  EVSHMVVVMVGSFCLCYVPYAALAMYMVNNRNHGLDLRLVTIPAFFSKSSCVYNPIIYCF  303
Chimera      EVSHMVVVMVGSFCVCYVPYAAFAMYMVNNRNHGLDLRLVTIPSFFSKSACTYNPIIYCF
```

FIG. 12B

| | | |
|---|---|---|
| Hu | 306 | MNKQFQACIMKMVCGKAMTDESDTCSSQKTEVSTVSSTQVGPN | 348 |
| Mo | 304 | MNKQFRACILEMVCRKPMADESDVSGSQKTEVSTVSSKVGPH | 346 |
| Chimera | | MNKQFRACILEMVCRKPMADESDVSGSQKTEVSTVSSKVGPH | a b

COMPOSITIONS AND METHODS FOR ENHANCING VISUAL FUNCTION

CROSS-REFERENCE

This application is a continuation of application PCT/US2018/060669 filed Nov. 13, 2018 which claims priority to provisional application U.S. Provisional Patent Application No. 62/585,237, filed Nov. 13, 2017, U.S. Provisional Patent Application No. 62/589,476, filed Nov. 21, 2017, and U.S. Provisional Patent Application No. 62/641,783, filed Mar. 12, 2018, each of which applications is incorporated herein by reference in its entirety.

STATEMENT REGARDING FEDERALLY SPONSORED RESEARCH

This invention was made with government support under EY018241 awarded by the National Institutes of Health. The government has certain rights in the invention.

INTRODUCTION

Inherited and age-related retinal degenerative diseases cause progressive loss of rod and cone photoreceptors, leading to complete blindness. Despite loss of the light-sensing cells required for vision, downstream neurons of the inner retina survive in a functional state, providing a target for optogenetic therapy. To date, optogenetic approaches have encountered certain limitations, including: a) very low light sensitivity in microbial opsins and chemically engineered mammalian receptors; b) very slow kinetics in retinal opsins; and c) a lack of the mechanisms of adaptation that provides natural vision with high sensitivity across a very wide range of ambient light levels.

There is a need in the art for improved optogenetic approaches to treating ocular disorders.

SUMMARY

The present disclosure provides a method of restoring or enhancing visual function in an individual, the method comprising administering to the individual a nucleic acid comprising a nucleotide sequence encoding one or more of a medium wavelength cone opsin (MW-opsin), a long wavelength cone opsin (LW-opsin), and a short wavelength cone opsin (SW-opsin). One or more of the MW-opsin, LW-opsin, and SW-opsin is expressed in a retinal cell in the individual, thereby restoring or enhancing visual function.

BRIEF DESCRIPTION OF THE DRAWINGS

FIG. 6 depicts behavioral tests demonstrating restoration of the ability to distinguish between parallel lines at 1 versus 6 cm distance by MW-opsin, LW-opsin, and SW-opsin.

FIG. 11 provides Table 1, which depicts statistical significance of light avoidance and learned visually-guided behavior.

FIG. 12A-12B provide an alignment of amino acid sequences of human SW-opsin (SEQ ID NO:5) and mouse SW-opsin (SEQ ID NO:6), and also provide an amino acid sequence of an example of a human/mouse SW-opsin chimera (SEQ ID NO:7). Transmembrane (TM) domains of human SW-opsin and chimeric human/mouse SW-opsin are underlined; intracellular domains of mouse SW-opsin and chimeric human/mouse SW-opsin are double underlined.

DEFINITIONS

Figures 1A, 1B, 1C:
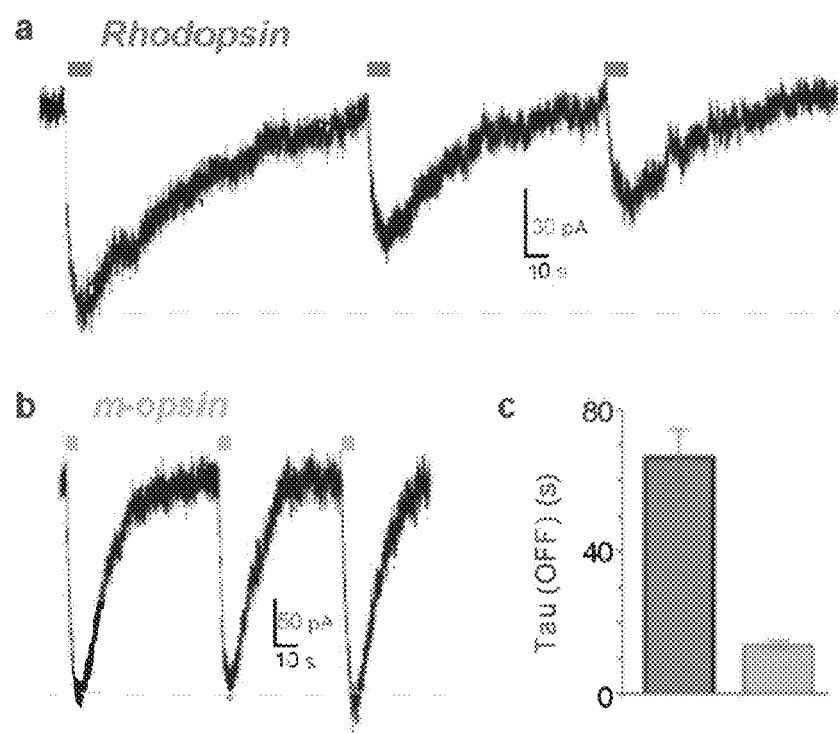
FIG. 1A-1C depict that activation by light of MW-opsin or rhodopsin turns on GIRK channels to generate an inward photocurrent at negative holding potentials in high external potassium.

The term "retinal cell" can refer herein to any of the cell types that comprise the retina, such as retinal ganglion cells; amacrine cells; horizontal cells; bipolar cells; and photoreceptor cells including rods and cones.

"Operatively linked" or "operably linked" refers to a juxtaposition of genetic elements, wherein the elements are in a relationship permitting them to operate in the expected manner. For instance, a promoter is operatively linked to a coding region if the promoter helps initiate transcription of the coding sequence. There may be intervening residues between the promoter and coding region so long as this functional relationship is maintained.

An "expression vector" is a vector comprising a region which encodes a polypeptide of interest, and is used for effecting the expression of the protein in an intended target cell. An expression vector also comprises control elements operatively linked to the encoding region to facilitate expression of the protein in the target. The combination of control elements and a gene or genes to which they are operably linked for expression is sometimes referred to as an "expression cassette," a large number of which are known and available in the art or can be readily constructed from components that are available in the art.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease or at risk of acquiring the disease but has not yet been diagnosed as having it; (b) inhibiting the disease, i.e., arresting its development; (c) relieving the disease, i.e., causing regression of the disease; and (d) replacing a lost function that results from the disease.

The terms "individual," "host," "subject," and "patient" are used interchangeably herein, and refer to a mammal, including, but not limited to, human and non-human primates, including simians and humans; mammalian sport animals (e.g., horses, camels, etc.); mammalian farm animals (e.g., sheep, goats, cows, etc.); mammalian pets (dogs, cats, etc.); and rodents (e.g., mice, rats, etc.). In some cases, the individual is a human.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an MW-opsin polypeptide" includes a plurality of such polypeptides and reference to "the retinal" includes reference to one or more retinal cells and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides a method of restoring or enhancing visual function in an individual, the method comprising administering to the individual a nucleic acid comprising a nucleotide sequence encoding one or more of a medium wavelength cone opsin (MW-opsin), a long wavelength cone opsin (LW-opsin), and a short wavelength cone opsin (SW-opsin). One or more of the MW-opsin, LW-opsin, and SW-opsin is expressed in a retinal cell in the individual, thereby restoring or enhancing visual function.

An MW-opsin polypeptide can comprise an amino acid sequence having at least 85%, at least 90%, at least 95%, at least 98%, at least 99%, or 100%, amino acid sequence identity to the following human MW-opsin amino acid sequence:

```
                                          (SEQ ID NO: 1)
MAQQWSLQRL AGRHPQDSYE DSTQSSIFTY TNSNSTRGPF

EGPNYHIAPR WVYHLTSVWM IFVVIASVFT NGLVLAATMK

FKKLRHPLNW ILVNLAVADL AETVIASTIS VVNQVYGYFV

LGHPMCVLEG YTVSLCGITG LWSLAIISWE RWMVVCKPFG

NVRFDAKLAI VGIAFSWIWA AVWTAPPIFG WSRYWPHGLK

TSCGPDVFSG SSYPGVQSYM IVLMVTCCIT PLSIIVLCYL

QVWLAIRAVA KQQKESESTQ KAEKEVTRMV VVMVLAFCFC

WGPYAFFACF AAANPGYPFH PLMAALPAFF AKSATIYNPV

IYVFMNRQFR NCILQLFGKK VDDGSELSSA SKTEVSSVSS VSPA.
```

An MW-opsin polypeptide can comprise an amino acid sequence having at least 85%, at least 90%, at least 95%, at least 98%, at least 99%, or 100%, amino acid sequence identity to the following mouse MW-opsin amino acid sequence:

(SEQ ID NO: 8)
```
MAQRLTGEQT LDHYEDSTHA SIFTYTNSNS TKGPFEGPNY
HIAPRWVYHL TSTWMILVVV ASVFTNGLVL AATMRFKKLR
HPLNWILVNL AVADLAETII ASTISVVNQI YGYFVLGHPL
CVIEGYIVSL CGITGLWSLA IISWERWLVV CKPFGNVRFD
AKLATVGIVF SWVWAAIWTA PPIFGWSRYW PYGLKTSCGP
DVFSGTSYPG VQSYMMVLMV TCCIFPLSII VLCYLQVWLA
IRAVAKQQKE SESTQKAEKE VTRMVVVMVF AYCLCWGPYT
FFACFATAHP GYAFHPLVAS LPSYFAKSAT IYNPIIYVFM
NRQFRNCILH LFGKKVDDSS ELSSTSKTEV SSVSSVSPA
```

A rhodopsin polypeptide can comprise an amino acid sequence having at least 85%, at least 90%, at least 95%, at least 98%, at least 99%, or 100%, amino acid sequence identity to the following rhodopsin amino acid sequence:

(SEQ ID NO: 2)
```
MNGTEGPNFY VPFSNATGVV RSPFEYPQYY LAEPWQFSML
AAYMFLLIVL GFPINFLTLY VTVQHKKLRT PLNYILLNLA
VADLFMVLGG FTSTLYTSLH GYFVFGPTGC NLEGFFATLG
GEIALWSLVV LAIERYVVVC KPMSNFRFGE NHAIMGVAFT
WVMALACAAP PLAGWSRYIP EGLQCSCGID YYTLKPEVNN
ESFVIYMFVV HFTIPMIIIF FCYGQLVFTV KEAAAQQQES
ATTQKAEKEV TRMVIIMVIA FLICWVPYAS VAFYIFTHQG
SNFGPIFMTI PAFFAKSAAI YNPVIYIMMN KQFRNCMLTT
ICCGKNPLGD DEASATVSKT ETSQVAPA.
```

A channelrhodopsin polypeptide can comprise an amino acid sequence having at least 85%, at least 90%, at least 95%, at least 98%, at least 99%, or 100%, amino acid sequence identity to the following channelrhodopsin amino acid sequence:

(SEQ ID NO: 3)
```
MDYGGALSAVGRELLFVTNPVVVNGSVLVPEDQCYCAGWIESRGTNGAQT
ASNVLQWLAAGFSILLLMFYAYQTWKSTCGWEEIYVCAIEMVKVILEFFF
EFKNPSMLYLATGHRVQWLRYAEWLLTCPVILIHLSNLTGLSNDYSRRTM
GLLVSDIGTIVWGATSAMATGYVKVIFFCLGLCYGANTFFHAAKAYIEGY
HTVPKGRCRQVVTGMAWLFFVSWGMFPILFILGPEGFGVLSVYGSTVGHT
IIDLMSKNCWGLLGHYLRVLIHEHILIHGDIRKTTKLNIGGTEIEVETLV
EDEAEAGAVP.
```

An LW-opsin can comprise an amino acid sequence having at least 85%, at least 90%, at least 95%, at least 98%, at least 99%, or 100%, amino acid sequence identity to the following human LW-opsin amino acid sequence:

(SEQ ID NO: 4)
```
MAQQWSLQRL AGRHPQDSYE DSTQSSIFTY TNSNSTRGPF
EGPNYHIAPR WVYHLTSVWM IFVVTASVFT NGLVLAATMK
FKKLRHPLNW ILVNLAVADL AETVIASTIS IVNQVSGYFV
LGHPMCVLEG YTVSLCGITG LWSLAIISWE RWMVVCKPFG
NVRFDAKLAI VGIAFSWIWA AVWTAPPIFG WSRYWPHGLK
TSCGPDVFSG SSYPGVQSYM IVLMVTCCII PLAIIMLCYL
QVWLAIRAVA KQQKESESTQ KAEKEVTRMV VVMIFAYCVC
WGPYTFFACF AAANPGYAFH PLMAALPAYF AKSATIYNPV
IYVFMNRQFR NCILQLFGKK VDDGSELSSA SKTEVSSVSS VSPA.
```

An LW-opsin can comprise an amino acid sequence having at least 85%, at least 90%, at least 95%, at least 98%, at least 99%, or 100%, amino acid sequence identity to the following mouse LW-opsin amino acid sequence:

(SEQ ID NO: 9)
```
MNGTEGPNFY VPFSNVTGVV RSPFEQPQYY LAEPWQFSML
AAYMFLLIVL GFPINFLTLY VTVQHKKLRT PLNYILLNLA
VADLFMVFGG FTTTLYTSLH GYFVFGPTGC NLEGFFATLG
GEIALWSLVV LAIERYVVVC KPMSNFRFGE NHAIMGVVFT
WIMALACAAP PLVGWSRYIP EGMQCSCGID YYTLKPEVNN
ESFVIYMFVV HFTIPMIVIF FCYGQLVFTV KEAAAQQQES
ATTQKAEKEV TRMVIIMVIF FLICWLPYAS VAFYIFTHQG
SNFGPIFMTL PAFFAKSSSI YNPVIYIMLN KQFRNCMLTT
LCCGKNPLGD DDASATASKT ETSQVAPA.
```

An SW-opsin polypeptide can comprise an amino acid sequence having at least 85%, at least 87%, at least 90%, at least 95%, at least 98%, at least 99%, or 100%, amino acid sequence identity to the following human SW-opsin amino acid sequence:

(SEQ ID NO: 5)
```
MRKMSEEEFY LFKNISSVGP WDGPQYHIAP VWAFYLQAAF
MGTVFLIGFP LNAMVLVATL RYKKLRQPLN YILVNVSFGG
FLLCIFSVFP VFVASCNGYF VFGRHVCALE GFLGTVAGLV
TGWSLAFLAF ERYIVICKPF GNFRFSSKHA LTVVLATWTI
GIGVSIPPFF GWSRFIPEGL QCSCGPDWYT VGTKYRSESY
TWFLFIFCFI VPLSLICFSY TQLLRALKAV AAQQQESATT
QKAEREVSRM VVVMVGSFCV CYVPYAAFAM YMVNNRNHGL
DLRLVTIPSF FSKSACIYNP IIYCFMNKQF QACIMKMVCG
KAMTDESDTC SSQKTEVSTV SSTQVGPN.
```

In some cases, an SW-opsin comprising an amino acid sequence having at least 87%, at least 90%, at least 95%, at least 98%, at least 99%, or 100%, amino acid sequence identity to human SW-opsin (SEQ ID NO:5) responds to light in the visible range, and exhibits excitatory activity.

An SW-opsin polypeptide can comprise an amino acid sequence having at least 87%, at least 90%, at least 95%, at least 98%, at least 99%, or 100%, amino acid sequence identity to the following mouse SW-opsin amino acid sequence:

(SEQ ID NO: 6)
```
MSGEDDFYLF QNISSVGPWD GPQYHLAPVW AFRLQAAFMG

FVFFVGTPLN AIVLVATLHY KKLRQPLNYI LVNVSLGGFL

FCIFSVFTVF IASCHGYFLF GRHVCALEAF LGSVAGLVTG

WSLAFLAFER YVVICKPFGS IRFNSKHALM VVLATWIIGI

GVSIPPFFGW SRFIPEGLQC SCGPDWYTVG TKYRSEYYTW

FLFIFCFIIP LSLICFSYSQ LLRTLRAVAA QQQESATTQK

AEREVSHMVV VMVGSFCLCY VPYAALAMYM VNNRNHGLDL

RLVTIPAFFS KSSCVYNPII YCFMNKQFRA CILEMVCRKP

MADESDVSGS QKTEVSTVSS SKVGPH.
```

In some cases, an SW-opsin comprising an amino acid sequence having at least 87%, at least 90%, at least 95%, at least 98%, at least 99%, or 100%, amino acid sequence identity to mouse SW-opsin (SEQ ID NO:6) responds to light in the ultraviolet range, and exhibits inhibitory activity.

In some cases, both a human SW-opsin and a mouse SW-opsin are produced in a retinal cell in an individual. In some cases, both a human SW-opsin and a mouse SW-opsin (but not an LW-opsin or an MW-opsin) are produced in a retinal cell in an individual. In some cases, both a human SW-opsin and a mouse SW-opsin, as well as an LW-opsin (but not an MW-opsin,) are produced in a retinal cell in an individual. In some cases, both a human SW-opsin and a mouse SW-opsin, as well as an MW-opsin (but not an LW-opsin), are produced in a retinal cell in an individual. In some cases, both a human SW-opsin and a mouse SW-opsin, as well as an LW-opsin an an MW-opsin, are produced in a retinal cell in an individual. For example, in some cases, a first recombinant expression vector comprising a nucleotide sequence encoding an SW-opsin polypeptide comprising an amino acid sequence having at least 87%, at least 90%, at least 95%, at least 98%, at least 99%, or 100%, amino acid sequence identity to human SW-opsin (SEQ ID NO:5); and a second first recombinant expression vector comprising a nucleotide sequence encoding an SW-opsin polypeptide comprising an amino acid sequence having at least 87%, at least 90%, at least 95%, at least 98%, at least 99%, or 100%, amino acid sequence identity to mouse SW-opsin (SEQ ID NO:6) are introduced into a retinal cell.

In some cases, both an MW-opsin and an LW-opsin (but not an SW-opsin) are produced in a retinal cell in an individual. In some cases, both an MW-opsin and an SW-opsin (but not an LW-opsin) are produced in a retinal cell in an individual. In some cases, an MW-opsin, an LW-opsin, and an SW-opsin are expressed in a retinal cell in an individual.

In some cases, a suitable opsin is a chimeric opsin, e.g., an opsin that includes an amino acid sequence(s) from a first species and an amino acid sequence(s) from a second species. For example, in some cases, a chimeric opsin comprises intracellular portions of mouse SW-opsin, and transmembrane portions of human SW-opsin. An example of a suitable chimeric SW-opsin is depicted in FIG. 12A-12B.

In some cases, a suitable chimeric SW-opsin comprises an amino acid sequence having at least at least 90%, at least 95%, at least 98%, at least 99%, or 100%, amino acid sequence identity to the chimeric SW-opsin depicted in FIG. 12A-12B, which chimeric SW-opsin has the following amino acid sequence:

(SEQ ID NO: 7)
```
EDDFYLFQNISSVGPWDGPQYHLAPVWAFYLQAAFMGTVFLIGFPLNAMV

LVATLHYKKLRQPLNYILVNVSFGGFLLCIFSVFPVFVASCNGYFVFGRH

VCALEGFLGTVAGLVTGWSLAFLAFERYVVICKPFGSIRFNSKHALTVVL

ATWTIGIGVSIPPFFGWSRFIPEGLQCSCGPDWYTVGTKYRSESYTWFLF

IFCFIVPLSLICFSYTQLLRALRAVAAQQQESATTQKAEREVSHMVVVMV

GSFCVCYVPYAAFAMYMVNNRNHGLDLRLVTIPSFFSKSACIYNPIIYCF

MNKQFRACILEMVCRKPMADESDVSGSQKTEVSTVSSSKVGPH.
```

An MW-opsin and/or an LW-opsin and/or an SW-opsin can be used in combination with a heterologous opsin, e.g., a non-mammalian opsin such as an algal opsin, an archaeal opsin, or a variant thereof. Suitable heterologous opsins include depolarizing opsins such as the channelrhodopsin ChR2 (Zhang et al. (2007) *Nature* 446:633; GenBank ABO64386.1) derived from *Chlamydomonas reinhardtii*; a step function opsin (SFO) protein (Berndt et al. (2009) *Nat. Neurosci.* 12:229) or a stabilized step function opsin (SSFO) protein (WO 2010/056970; Yizhar et al. (2011) *Nature* 477:171); a cation channel derived from *Volvox carteri* (VChR1—NCBI Gene ID: 9619570; U.S. Pat. No. 9,249, 200); a C1V1 chimeric protein derived from the VChR1 protein of *Volvox carteri* and the ChR1 protein from *Chlamydomonas reinhardtii* (U.S. Pat. No. 9,175,095); a C1C2 chimeric protein derived from the ChR1 and the ChR2 proteins from *Chlamydomonas reinhardtii* (Lin et al. (2009) *Biophys. J.* 96:1803); a red shifted variant of a depolarizing light-responsive polypeptide derived from *Chlamydomonas reinhardtii*, where such light-responsive polypeptides are referred to as "ReaChR" (Lin et al. (2013) *Nat. Neurosci.* 16:1499); CnChR2 (Genbank Accession No.: AHH02139), derived from *Chlamydomonas* noctigama; a CsChrimson chimeric protein derived from a CsChR (Genbank Accession No.: AHH02144; Klapoetke et al. (2014) *Nature Methods* 11:338) protein of *Chloromonas subdivisa*; ShChR1 (Genbank Accession No.: AHH02106), derived from *Stigeoclonium helveticum*; a "ChETA" opsin (Gunaydin et al. (2010 *Nat. Neurosci.* 13:387) a "SwiChR" protein (WO 2015/148974); a "bReaChes" protein (WO/2017/048808); and the like. Other suitable depolarizing opsins are known in the art; see, e.g., Zhang et al. (2011) *Cell* 147:1446; Deisseroth (2015) *Nature Neurosci.* 18:1213; Berndt and Deisseroth (2015) *Science* 349:590; and the like.

Expression of an MW-opsin polypeptide and/or an LW-opsin polypeptide and/or an SW-opsin polypeptide in a retinal cell in an individual provides for patterned vision and image recognition by the individual. Image recognition can be of a static image and/or of a moving image.

Expression of an MW-opsin polypeptide and/or an LW-opsin polypeptide and/or an SW-opsin polypeptide in a retinal cell in an individual provides for image recognition at a light intensity of from about $10^{-4}$ W/cm$^2$ to about 10 W/cm$^2$. For example, in some cases, expression of an MW-opsin polypeptide and/or an LW-opsin polypeptide and/or an SW-opsin polypeptide in a retinal cell in an individual provides for image recognition at a light intensity of from about $10^{-2}$ W/cm$^2$ to about $10^{-4}$ W/cm$^2$, from about $10^{-4}$ W/cm$^2$ to about 1 W/cm$^2$, from about $10^{-4}$ W/cm$^2$ to about $10^{-1}$ W/cm$^2$, or from about $10^{-4}$ W/cm$^2$ to about $5 \times 10^{-1}$ W/cm². In some cases, expression of an MW-opsin polypeptide and/or an LW-opsin polypeptide and/or an SW-opsin polypeptide in a retinal cell in an individual provides for image recognition at a light intensity of from about $10^{-4}$ W/cm² to about $10^{-3}$ W/cm², from about $10^{-3}$ W/cm² to about $10^{-2}$ W/cm², from about $10^{-2}$ W/cm² to about $10^{-1}$ W/cm², or from about $10^{-1}$ W/cm² to about 1 W/cm². In some cases, expression of an MW-opsin polypeptide and/or an LW-opsin polypeptide and/or an SW-opsin polypeptide in a retinal cell in an individual provides for image recognition at a light intensity of up to 2 W/cm² up to 3 W/cm², up to 4 W/cm², up to 5 W/cm², or up to 10 W/cm². Expression of an MW-opsin polypeptide and/or an LW-opsin polypeptide and/or an SW-opsin polypeptide in a retinal cell in an individual provides for image recognition at a light intensity of less than 5 W/cm², less than 4 W/cm², less than 3 W/cm², or less than 2 W/cm².

Expression of an MW-opsin polypeptide and/or an LW-opsin polypeptide and/or an SW-opsin polypeptide in a retinal cell in an individual provides for image recognition by the individual at a light intensity that is at least 10-fold lower than the light intensity required to provide for image recognition by an individual expressing a channelrhodopsin polypeptide (e.g., a polypeptide comprising the amino acid sequence set forth in SEQ ID NO:3) in a retinal cell. For example, expression of an MW-opsin polypeptide and/or an LW-opsin polypeptide and/or an SW-opsin polypeptide in a retinal cell in an individual provides for image recognition by the individual at a light intensity that is at least 10-fold lower, at least 25-fold lower, at least 50-fold lower, at least 100-fold lower, at least 150-fold lower, at least 200-fold lower, at least 300-fold lower, at least 400-fold lower, or at least 500-fold lower, than the light intensity required to provide for image recognition by an individual expressing a channelrhodopsin polypeptide in a retinal cell.

Expression of an MW-opsin polypeptide and/or an LW-opsin polypeptide and/or an SW-opsin polypeptide in a retinal cell provides for kinetics that are at least 2-fold faster than the kinetics conferred on a retinal cell by a rhodopsin polypeptide (e.g., a polypeptide comprising the amino acid sequence set forth in SEQ ID NO:2). For example, expression of an MW-opsin polypeptide and/or an LW-opsin polypeptide and/or an SW-opsin polypeptide in a retinal cell provides for kinetics that are at least 2-fold, at least 5-fold, at least 10-fold, at least 15-fold, at least 20-fold, at least 25-fold, at least 30-fold, at least 50-fold, at least 100-fold, or more than 100-fold, faster than the kinetics conferred on a retinal cell by a rhodopsin polypeptide.

A method of the present disclosure comprises delivery to an eye of an individual a nucleic acid comprising a nucleotide sequence encoding an MW-opsin polypeptide and/or an LW-opsin polypeptide and/or an SW-opsin polypeptide. In some cases, the nucleotide sequence is operably linked to a transcriptional control element that is functional in a mammalian cell. In some cases, the nucleotide sequence is operably linked to a transcriptional control element that provides for expression in a retinal cell, e.g., that provides for selective expression in a retinal cell. In some cases, the nucleotide sequence is operably linked to a promoter that provides for expression in a retinal cell, e.g., that provides for selective expression in a retinal cell. In some cases, the nucleotide sequence is operably linked to a promoter that generally provides for expression in a eukaryotic or mammalian cell.

Suitable promoters include, but are not limited to, a CAG promoter (Miyazaki et al. (1989) *Gene* 79:269); a cytomegalovirus (CMV) promoter; a glutamate metabotropic receptor-6 (grm6) promoter (Cronin et al. (2014) *EMBO Mol. Med.* 6:1175); a Pleiades promoter (Portales-Casamar et al. (2010) *Proc. Natl. Acad. Sci. USA* 107:16589); a choline acetyltransferase (ChAT) promoter (Misawa et al. (1992) *J. Biol. Chem.* 267:20392); a vesicular glutamate transporter (V-glut) promoter (Zhang et al. (2011) *Brain Res.* 1377:1); a glutamic acid decarboxylase (GAD) promoter (Rasmussen et al. (2007) *Brain Res.* 1144:19; Ritter et al. (2016) *J. Gene Med.* 18:27); a cholecystokinin (CCK) promoter (Ritter et al. (2016) *J. Gene Med.* 18:27); a parvalbumin (PV) promoter; a somatostatin (SST) promoter; a neuropeptide Y (NPY) promoter; and a vasoactive intestinal peptide (VIP) promoter. Suitable promoters include, but are not limited to, a red cone opsin promoter, rhodopsin promoter, a rhodopsin kinase promoter, and a GluR promoter (e.g., a GluR6 promoter; also referred to as grm6). Suitable promoters include, but are not limited to, a vitelliform macular dystrophy 2 (VMD2) gene promoter, and an interphotoreceptor retinoid-binding protein (IRBP) gene promoter. Also suitable for use is an L7 promoter (Oberdick et al. (1990) *Science* 248:223), a thy-1 promoter, a recoverin promoter (Wiechmann and Howard (2003) *Curr. Eye Res.* 26:25); a calbindin promoter; and a beta-actin promoter. Suitable promoters include synthetic (non-naturally occurring) promoter/enhancer combinations.

In some cases, a nucleic acid comprising a nucleotide sequence encoding an MW-opsin polypeptide and/or an LW-opsin polypeptide and/or an SW-opsin polypeptide is in a recombinant expression vector. Suitable expression vectors include, but are not limited to, a lentivirus vector, a herpes simplex virus (HSV) vector, an adenovirus vector, a retroviral vector, an adenoassociated virus (AAV) vector, and the like. Thus, in some cases, a nucleic acid comprising a nucleotide sequence encoding an MW-opsin polypeptide and/or an LW-opsin polypeptide and/or an SW-opsin polypeptide is a recombinant lentivirus vector, a recombinant HSV vector, a recombinant adenovirus vector, a recombinant retrovirus vector, or a recombinant AAV vector.

In some cases, a nucleic acid (e.g., a recombinant expression vector) comprising a nucleotide sequence encoding an MW-opsin polypeptide and/or an LW-opsin polypeptide and/or an SW-opsin polypeptide is complexed with a nanoparticle.

In some cases, a nucleic acid comprising a nucleotide sequence encoding an MW-opsin polypeptide and/or an LW-opsin polypeptide and/or an SW-opsin polypeptide is recombinant AAV (rAAV) vector. In some cases, the rAAV vector comprises a nucleotide sequence encoding a variant AAV capsid protein, where the variant AAV capsid protein confers infectivity of a retinal cell and/or the ability to cross the inner limiting membrane (ILM) in the eye. See, e.g., Day et al. (2014) *Adv. Exp. Med. Biol.* 801:687; Boye et al. (2016) *J. Virol.* 90:4215; Vandenberghe and Auricchio (2012) *Gene Therapy* 19:162; Klimczak et al. (2009) *PLoS One* 4:e7467; U.S. Patent Publication No. 2012/0164106; and U.S. Patent Publication No. 2016/0017295.

Retinal cells include retinal ganglion cells; amacrine cells; horizontal cells; bipolar cells; and photoreceptor cells including rods and cones.

In some cases, a method of the present disclosure comprises administering to an individual in need thereof a pharmaceutical composition comprising: a) a nucleic acid (e.g., a recombinant expression vector) comprising a nucleotide sequence encoding an MW-opsin and/or an LW-opsin polypeptide and/or an SW-opsin polypeptide; and b) a pharmaceutically acceptable excipient.

A pharmaceutical composition comprising a nucleic acid (e.g., a recombinant expression vector) comprising a nucleotide sequence encoding an MW-opsin and/or an LW-opsin and/or an SW-opsin polypeptide may be administered to a patient alone, or in combination with other supplementary active agents. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilisate, tablet, pill, pellet, capsule, powder, syrup, elixir or any other dosage form suitable for administration.

A pharmaceutical composition comprising a nucleic acid (e.g., a recombinant expression vector) comprising a nucleotide sequence encoding an MW-opsin polypeptide and/or an LW-opsin polypeptide and/or an SW-opsin polypeptide can optionally include a pharmaceutically acceptable carrier(s) that facilitate processing of an active ingredient into pharmaceutically acceptable compositions. As used herein, the term "pharmacologically acceptable carrier" refers to any carrier that has substantially no long-term or permanent detrimental effect when administered and encompasses terms such as "pharmacologically acceptable vehicle, stabilizer, diluent, auxiliary or excipient." Such a carrier generally is mixed with an active compound (e.g., a nucleic acid of the present disclosure), or permitted to dilute or enclose the active compound and can be a solid, semi-solid, or liquid agent. It is understood that the active ingredients can be non-soluble or can be delivered as a suspension in the desired carrier or diluent. Any of a variety of pharmaceutically acceptable carriers can be used including, without limitation, aqueous media such as, e.g., distilled, deionized water, saline; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in "Pharmaceutical Dosage Forms and Drug Delivery Systems" (Howard C. Ansel et al., eds., Lippincott Williams & Wilkins Publishers, 7$^{th}$ ed. 1999); "Remington: The Science and Practice of Pharmacy" (Alfonso R. Gennaro ed., Lippincott, Williams & Wilkins, 20 2000); "Goodman & Gilman's The Pharmacological Basis of Therapeutics" Joel G. Hardman et al., eds., McGraw-Hill Professional, 10.sup.th ed. 2001); and "Handbook of Pharmaceutical Excipients" (Raymond C. Rowe et al., APhA Publications, 4$^{th}$ edition 2003).

A pharmaceutical composition can optionally include, without limitation, other pharmaceutically acceptable components, including, without limitation, buffers, preservatives, tonicity adjusters, salts, antioxidants, physiological substances, pharmacological substances, bulking agents, emulsifying agents, wetting agents, sweetening or flavoring agents, and the like. Various buffers and means for adjusting pH can be used to prepare a pharmaceutical composition, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate and a stabilized oxy chloro composition, for example, PURITE™. Tonicity adjustors suitable for inclusion in a pharmaceutical composition include, without limitation, salts such as, e.g., sodium chloride, potassium chloride, mannitol or glycerin and other pharmaceutically acceptable tonicity adjustor. It is understood that these and other substances known in the art of pharmacology can be included in a pharmaceutical composition.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

In some cases, a nucleic acid (e.g., a recombinant expression vector) comprising a nucleotide sequence encoding an MW-opsin polypeptide and/or an LW-opsin polypeptide and/or an SW-opsin polypeptide is formulated with one or more biocompatible polymers. Suitable biocompatible polymers include, but are not limited to, polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, poly(vinylpyrrolidone), polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulfate sodium salt poly-methyl methacrylate), poly(ethyl methacrylate), poly (butyl methacrylate), poly(isobutyl methacrylate\ poly (hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene poly (ethylene glycol), poly(ethylene oxide), poly(ethylene terephthalate), poly(vinyl alcohols), polyvinyl acetate, polyvinyl chloride polystyrene, poly(vinyl pyrrolidone), polyhyaluronic acids, casein, gelatin, glutin, polyanhydrides, polyacrylic acid, alginate, chitosan, poly(methyl methacrylates), poly(ethyl methacrylates), poly(butyl methacrylate), poly (isobutyl methacrylate), poly(hexyl methacrylate) poly(isodecyl methaerylate), poly(lauryl methacrylate), poly(phenyl methacrylate), poly(methyl acrylate), poly(isopropyl acrylatee), poly(isobutyl acrylate), poly(octadecyl acrylate) and combinations of any of the forgoing.

In some cases, a nucleic acid (e.g., a recombinant expression vector) comprising a nucleotide sequence encoding an MW-opsin polypeptide and/or an LW-opsin polypeptide and/or an SW-opsin polypeptide is formulated in a liposome. See, e.g., U.S. Patent Publication No. 2017/0119666. In some cases, a nucleic acid (e.g., a recombinant expression vector) comprising a nucleotide sequence encoding an MW-opsin polypeptide and/or an LW-opsin polypeptide and/or an SW-opsin polypeptide is formulated in a nanoparticle. Nanoparticles include, e.g., polyalkylcyanoacrylate nanoparticles, nanoparticles comprising poly(lactic acid), nanoparticles comprising poly(lactic-co-glycolic acid) (PLGA) nanoparticles, and the like. In some cases, a nucleic acid (e.g., a recombinant expression vector) comprising a nucleotide sequence encoding an MW-opsin polypeptide and/or an LW-opsin polypeptide and/or an SW-opsin polypeptide is formulated in a hydrogel. Suitable hydrogel components include, but are not limited to, silk (see, e.g., U.S. Patent Publication No. 2017/0173161), poly(lactic acid) (PLA), poly(glycolic acid) (PGA), poly(lactide-co-glycolide) (PLGA), polyesters, poly(ortho ester), poly(phosphazine), poly(phosphate ester), polycaprolactone, gelatin, collagen, cellulose, hyaluronan, poly(ethylene glycol) (PEG), triblock copolymers, polylysine, poly(ethylene oxide), poly(vinyl pyrrolidone), hyaluronic acid, acrylated hyaluronic acid, poly(N-isopropylacrylamide), and the like.

In some cases, a composition comprising a nucleic acid (e.g., a recombinant expression vector) comprising a nucleotide sequence encoding an MW-opsin polypeptide and/or an LW-opsin polypeptide and/or an SW-opsin polypeptide is present in a buffered saline solution. In some cases, a composition comprising a recombinant viral expression vector comprising a nucleotide sequence encoding an MW-opsin and/or an LW-opsin and/or an SW-opsin polypeptide is present in a buffered saline solution in an amount of from about $10^8$ to about $10^{15}$ viral genomes (vg) in a volume of from about 50 µL to about 1000 µL. For instance, in some cases, a composition comprising a recombinant viral expression vector comprising a nucleotide sequence encoding an MW-opsin and/or an LW-opsin and/or an SW-opsin polypeptide is present in a buffered saline solution in an amount of from about $10^8$ vg to about $10^9$ vg, from about $10^9$ vg to about $10^{10}$ vg, from about $10^{10}$ vg to about $10^{11}$ vg, from about $10^{11}$ vg to about $10^{12}$ vg, from about $10^{12}$ vg to about $10^{13}$ vg, from about $10^{13}$ vg to about $10^{14}$ vg, or from about $10^{14}$ vg to about $10^{15}$ vg, in a volume of from about 50 µL to about 75 µL, from about 75 µL to about 100 µL, from about 100 µL to about 150 µL, from about 150 µL to about 200 µL, from about 200 µL to about 300 µL, from about 300 µL to about 400 µL, from about 400 µL to about 500 µL, from about 500 µL to about 600 µL, from about 600 µL to about 700 µL, from about 800 µL to about 900 µL, or from about 900 µL to about 1000 µL. In some cases, a composition comprising a nucleic acid (e.g., a recombinant expression vector) comprising a nucleotide sequence encoding an MW-opsin and/or an LW-opsin and/or an SW-opsin polypeptide is present in a buffered saline solution containing a non-ionic detergent in a concentration of about 0.001%. Suitable non-ionic detergents include, e.g., Pluronic F68®. In some cases, a composition comprising a recombinant viral expression vector comprising a nucleotide sequence encoding an MW-opsin and/or an LW-opsin and/or an SW-opsin polypeptide is present in a buffered saline solution in an amount of from about $10^8$ vg to about $10^9$ vg, from about $10^9$ vg to about $10^{10}$ vg, from about $10^{10}$ vg to about $10^{11}$ vg, from about $10^{11}$ vg to about $10^{12}$ vg, from about $10^{12}$ vg to about $10^{13}$ vg, from about $10^{13}$ vg to about $10^{14}$ vg, or from about $10^{14}$ vg to about $10^{15}$ vg, in a volume of from about 50 µL to about 75 µL, from about 75 µL to about 100 µL, from about 100 µL to about 150 µL, from about 150 µL to about 200 µL, from about 200 µL to about 300 µL, from about 300 µL to about 400 µL, from about 400 µL to about 500 µL, from about 500 µL to about 600 µL, from about 600 µL to about 700 µL, from about 800 µL to about 900 µL, or from about 900 µL to about 1000 µL, where the buffered saline solution comprises a non-ionic detergent in a concentration of about 0.001%. A saline solution can comprise 0.9% NaCl.

A nucleic acid (e.g., a recombinant expression vector, such as a recombinant viral vector) comprising a nucleotide sequence encoding an MW-opsin and/or an LW-opsin and/or an SW-opsin polypeptide can be administered to an individual in need thereof by any of a variety of routes of administration. Suitable routes of administration include, e.g., periocular, intraocular, intravitreal, subconjunctive, retrobulbar, into the sclera, and intercameral. In some cases, a nucleic acid (e.g., a recombinant expression vector) comprising a nucleotide sequence encoding an MW-opsin and/or an LW-opsin and/or an SW-opsin polypeptide is delivered by intravitreal injection. In some cases, a nucleic acid (e.g., a recombinant expression vector) comprising a nucleotide sequence encoding an MW-opsin and/or an LW-opsin and/or an SW-opsin polypeptide is delivered intraocularly. In some cases, a nucleic acid (e.g., a recombinant expression vector) comprising a nucleotide sequence encoding an MW-opsin and/or an LW-opsin and/or an SW-opsin polypeptide is delivered via sub-retinal injection.

In some cases, a method of the present disclosure comprises administering to an individual in need thereof a single administration (per eye) of a composition comprising a nucleic acid (e.g., a recombinant expression vector, such as a recombinant viral vector) comprising a nucleotide sequence encoding an MW-opsin and/or an LW-opsin and/or an SW-opsin polypeptide.

In some cases, multiple doses of a nucleic acid (e.g., a recombinant expression vector) comprising a nucleotide sequence encoding an MW-opsin and/or an LW-opsin are administered to an individual. The frequency of administration can vary depending on any of a variety of factors, e.g., severity of the symptoms, etc. For example, in some cases, a nucleic acid (e.g., a recombinant expression vector) comprising a nucleotide sequence encoding an MW-opsin and/or an LW-opsin and/or an SW-opsin polypeptide is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

A nucleic acid (e.g., a recombinant expression vector) comprising a nucleotide sequence encoding an MW-opsin and/or an LW-opsin and/or an SW-opsin polypeptide can be administered to an individual over a period of time of from about 1 day to about 1 year or more than 1 year. For example, a nucleic acid (e.g., a recombinant expression vector) comprising a nucleotide sequence encoding an MW-opsin and/or an LW-opsin and/or an SW-opsin polypeptide can be administered to an individual for a period of time of from 1 week to 2 weeks, from 2 weeks to 1 month, from 1 month to 4 months, from 4 months to 6 months, from 6 months to 1 year, or more than 1 year.

Where a nucleic acid comprising a nucleotide sequence is a recombinant viral expression vector comprising a nucleotide sequence encoding an MW-opsin and/or an LW-opsin and/or an SW-opsin polypeptide, the recombinant viral vector can be administered in an amount of from about $10^8$ vg to about $10^9$ vg, from about $10^9$ vg to about $10^{10}$ vg, from about $10^{10}$ vg to about $10^{11}$ vg, from about $10^{11}$ vg to about $10^{12}$ vg, from about $10^{12}$ vg to about $10^{13}$ vg, from about $10^{13}$ vg to about $10^{14}$ vg, or from about $10^{14}$ vg to about $10^{15}$ vg, per dose.

A nucleic acid (e.g., a recombinant expression vector) comprising a nucleotide sequence encoding an MW-opsin and/or an LW-opsin and/or an SW-opsin polypeptide is administered in an amount effective to increase visual function in an individual by at least 10%, at least 15%, at least 20%, at least 25%, at least 30%, at least 40%, at least 50%, at least 2-fold, at least 5-fold, at least 10-fold, or more than 10-fold, compared with the visual function before administration of the nucleic acid. Tests for visual function are known in the art, and any known test can be applied to assess visual function.

Individuals suitable for treatment with a method of the present disclosure include individuals having reduced visual function due to loss of rod and cone photoreceptors. In some cases, the individual has an inherited retinal degenerative disease such as retinitis pigmentosa, retinoschisis, or Leber's Congenital Amaurosis. In some cases, the individual has an ocular disease (e.g., an inherited ocular disease) selected from retinitis pigmentosa, macular degeneration, age-related macular degeneration, retinoschisis, and Leber's Congenital Amaurosis, and diabetic retinopathy. Individuals suitable for treatment with a method of the present disclosure include individuals having a retinal degeneration condition in which the natural light sensitivity is lost and vision is therefore compromised, but where neurons late in the retinal circuit (e.g. bipolar cells or amacrine interneurons or ganglion cells that output to the brain) are spared and can be made directly sensitive to light by introduction of the cone opsin(s).

Individuals suitable for treatment with a method of the present disclosure include individuals having retinal damage that is traumatic or acute, with no genetic or inherited basis. For example, in some cases, the individual has experienced retinal detachment resulting from blunt trauma, such as a blast injury (e.g., in a military battle), or resulting from an impact to the head, e.g., in the course of an auto accident or other accident resulting in impact to the head. In some instances, the photoreceptors are lost due to traumatic detachment of the retina from the underlying RPE, but the inner retinal neurons are intact. Individuals suitable for treatment with a method of the present disclosure include individuals having photoreceptor loss due to acute light damage, laser exposure, or chemical toxicity.

Compositions

The present disclosure provides compositions comprising one or more recombinant nucleic acid vectors comprising one or more nucleotide sequences encoding one or more cone opsins. When the composition is administered to an individual in need thereof, the one or more nucleotide sequences encoding the one or more cone opsins are expressed in an eye of a subject in need thereof, such that the one or more cone opsins are produced in the eye of the subject, one or more beneficial clinical outcomes results. For example, when the composition is administered to an eye of an individual in need thereof, the one or more nucleotide sequences encoding the one or more cone opsins are expressed in an eye of a subject in need thereof, such that the one or more cone opsins are produced in the eye of the subject, one or more beneficial clinical outcomes results. When the one or more nucleotide sequences encoding the one or more cone opsins are expressed in an eye of a subject in need thereof, such that the one or more cone opsins are produced in the eye of the subject, one or more beneficial clinical outcomes results. Beneficial clinical outcomes include: 1) the subject can distinguish between an image comprising a vertical line and an image comprising a horizontal line in a spatial pattern discrimination assay; 2) the subject can distinguish between an image comprising a static line and an image comprising a moving line in a spatial pattern discrimination assay; 3) the subject can distinguish between flashing light and constant light in a temporal light pattern assay; 4) the subject can recognize an image at a light intensity of from about $10^{-4}$ W/cm$^2$ to about 10 W/cm$^2$ in an image recognition assay; and 5) subject can distinguish between an area with white light and an area without white light in a light avoidance assay.

Whether a composition provides one or more of the above-noted beneficial clinical outcomes can be determined using tests that are known in the art. See e.g., Leinonen and Tanila (2017) *Behavioural Brain Research* pii: S0166-4328 (17)30870-7; Caporale et al. (2011). *Molecular Therapy* 19, 1212-9; Gaub et al. (2014) *Proc. Natl. Acad. Sci. USA* 111, E5574-83; Gaub et al. (2015) *Molecular Therapy* 23:1562; and Berry et al. (2017) *Nat. Commun.* 8:1862.

The present disclosure composition comprising one or more recombinant nucleic acid vectors comprising one or more nucleotide sequences encoding one or more cone opsins, wherein, when: i) the composition is administered to an individual in need thereof; or ii) the composition is administered to an eye of an individual in need thereof, such that the one or more nucleotide sequences is expressed in an eye of a subject in need thereof (such that the one or more opsins is produced in the eye of the subject), the subject can distinguish between an image comprising a vertical line and an image comprising a horizontal line in a spatial pattern discrimination assay. The present disclosure composition comprising one or more recombinant nucleic acid vectors comprising one or more nucleotide sequences encoding one or more cone opsins, wherein, when the one or more nucleotide sequences is expressed in an eye of a subject in need thereof (such that the one or more opsins is produced in the eye of the subject), the subject can distinguish between an image comprising a vertical line and an image comprising a horizontal line in a spatial pattern discrimination assay.

The present disclosure composition comprising one or more recombinant nucleic acid vectors comprising one or more nucleotide sequences encoding one or more cone opsins, wherein, when: i) the composition is administered to an individual in need thereof; or ii) the composition is administered to an eye of an individual in need thereof, such that the one or more nucleotide sequences is expressed in an eye of a subject in need thereof (such that the one or more opsins is produced in the eye of the subject), the subject can distinguish between an image comprising a static line and an image comprising a moving line in a spatial pattern discrimination assay. The present disclosure provides a composition comprising one or more recombinant nucleic acid vectors comprising one or more nucleotide sequences encoding one or more cone opsins, wherein, when said one or more nucleotide sequences is expressed in an eye of a subject in need thereof (such that the one or more opsins is produced in the eye of the subject), the subject can distinguish between an image comprising a static line and an image comprising a moving line in a spatial pattern discrimination assay.

The present disclosure composition comprising one or more recombinant nucleic acid vectors comprising one or more nucleotide sequences encoding one or more cone opsins, wherein, when: i) the composition is administered to an individual in need thereof; or ii) the composition is administered to an eye of an individual in need thereof, such that the one or more nucleotide sequences is expressed in an eye of a subject in need thereof (such that the one or more opsins is produced in the eye of the subject), the subject can distinguish between flashing light and constant light in a temporal light pattern assay. The present disclosure provides a composition comprising one or more recombinant nucleic acid vectors comprising one or more nucleotide sequences encoding one or more cone opsins, wherein, when said one or more nucleotide sequences is expressed in an eye of a subject in need thereof (such that the one or more opsins is produced in the eye of the subject), the subject can distinguish between flashing light and constant light in a temporal light pattern assay.

The present disclosure composition comprising one or more recombinant nucleic acid vectors comprising one or more nucleotide sequences encoding one or more cone opsins, wherein, when: i) the composition is administered to an individual in need thereof; or ii) the composition is administered to an eye of an individual in need thereof, such that the one or more nucleotide sequences is expressed in an eye of a subject in need thereof (such that the one or more opsins is produced in the eye of the subject), the subject can recognize an image at a light intensity of from about $10^{-4}$ W/cm$^2$ to about 10 W/cm$^2$ in an image recognition assay. The present disclosure provides a composition comprising one or more recombinant nucleic acid vectors comprising one or more nucleotide sequences encoding one or more cone opsins, wherein, when said one or more nucleotide sequences is expressed in an eye of a subject in need thereof (such that the one or more opsins is produced in the eye of the subject), the subject can recognize an image at a light intensity of from about $10^{-4}$ W/cm$^2$ to about 10 W/cm$^2$ (e.g., a light intensity of from about $10^{-4}$ W/cm$^2$ to about $10^{-3}$ W/cm$^2$, from about $10^{-3}$ W/cm$^2$ to about $10^2$ W/cm$^2$, from about $10^{-2}$ W/cm$^2$ to about $10^{-1}$ W/cm$^2$, or from about $10^{-1}$ W/cm$^2$ to about 1 W/cm$^2$. In some cases, expression of an MW-opsin polypeptide and/or an LW-opsin polypeptide and/or an SW-opsin polypeptide in a retinal cell in an individual provides for image recognition at a light intensity of up to 2 W/cm$^2$ up to 3 W/cm$^2$, up to 4 W/cm$^2$, up to 5 W/cm$^2$, or up to 10 W/cm$^2$) in an image recognition assay.

The present disclosure composition comprising one or more recombinant nucleic acid vectors comprising one or more nucleotide sequences encoding one or more cone opsins, wherein, when: i) the composition is administered to an individual in need thereof; or ii) the composition is administered to an eye of an individual in need thereof, such that the one or more nucleotide sequences is expressed in an eye of a subject in need thereof (such that the one or more opsins is produced in the eye of the subject), the subject can distinguish between an area with white light and an area without white light in a light avoidance assay. The present disclosure provides a composition comprising one or more recombinant nucleic acid vectors comprising one or more nucleotide sequences encoding one or more cone opsins, wherein, when said one or more nucleotide sequences is expressed in an eye of a subject in need thereof (such that the one or more opsins is produced in the eye of the subject), the subject can distinguish between an area with white light and an area without white light in a light avoidance assay.

Cone opsins that can be encoded by the one or more recombinant nucleic acids present in a composition of the present disclosure are described above, and include, e.g., an MW-opsin, an LW-opsin, an SW-opsin, a chimeric opsin, and the like.

In some cases, the one or more cone opsins encoded by the one or more recombinant nucleic acids present in a composition of the present disclosure is selected from the group consisting of:

a) an MW-opsin comprising an amino acid sequence having at least 85%, at least 90%, at least 95%, at least 98%, at least 99%, or 100%, amino acid sequence identity to the amino acid sequence set forth in SEQ ID NO:1;

b) an LW-opsin comprising an amino acid sequence having at least 85%, at least 90%, at least 95%, at least 98%, at least 99%, or 100%, amino acid sequence identity to the amino acid sequence set forth in SEQ ID NO:4;

c) an SW-opsin comprising an amino acid sequence having at least 85%, at least 90%, at least 95%, at least 98%, at least 99%, or 100%, amino acid sequence identity to the amino acid sequence set forth in SEQ ID NO:5; and d) a chimeric SW-opsin comprising: i) intracellular portions of a mouse SW-opsin comprising an amino acid sequence having at least 85%, at least 87%, at least 90%, at least 95%, at least 98%, at least 99%, or 100%, amino acid sequence identity to the amino acid sequence set forth in SEQ ID NO:6; and ii) transmembrane portions of a human SW-opsin comprising an amino acid sequence having at least 85%, at least 87%, at least 90%, at least 95%, at least 98%, at least 99%, or 100%, amino acid sequence identity to the amino acid sequence set forth in SEQ ID NO:5.

In some cases, a composition of the present disclosure comprises a recombinant nucleic acid comprising a nucleotide sequence that encodes a single cone opsin. In some cases, the one or more recombinant nucleic acid vectors present in a composition of the present disclosure comprises one or more nucleotide sequences encoding 2 different cone opsins. For example, in some cases, the one or more recombinant nucleic acid vectors present in a composition of the present disclosure comprises one or more nucleotide sequences encoding an MW-opsin and an LW-opsin. As another example, in some cases, the one or more recombinant nucleic acid vectors present in a composition of the present disclosure comprises one or more nucleotide sequences encoding an MW-opsin and an SW-opsin. As another example, in some cases, the one or more recombinant nucleic acid vectors present in a composition of the present disclosure comprises one or more nucleotide sequences encoding an LW-opsin and an SW-opsin. The 2 different cone opsins can be encoded on a single recombinant nucleic acid. The 2 different cone opsins can be encoded on 2 separate recombinant nucleic acids.

In some cases, the one or more recombinant nucleic acid vectors present in a composition of the present disclosure comprises one or more nucleotide sequences encoding 3 different cone opsins. For example, in some cases, the one or more recombinant nucleic acid vectors present in a composition of the present disclosure comprises one or more nucleotide sequences encoding an MW-opsin, an SW-opsin, and an LW-opsin. The 3 different cone opsins can be encoded on a single recombinant nucleic acid. The 3 different cone opsins can be encoded on 3 separate recombinant nucleic acids.

Suitable recombinant nucleic acid vectors include a recombinant adeno-associated viral vector, a recombinant lentiviral vector, a recombinant herpes simplex virus vector, and a recombinant retroviral vector. In some cases, the one or more recombinant nucleic acid vectors is/are recombinant adeno-associated virus vectors. In some instances, the recombinant AAV vector comprises a nucleotide sequence encoding a variant capsid polypeptide that confers increased infectivity of a retinal cell and/or confers increased ability to cross the inner limiting membrane, compared to a wild-type AAV capsid.

A nucleotide sequence encoding a cone opsin can be operably linked to one or more transcriptional control elements. For example, a nucleotide sequence encoding a cone opsin can be operably linked to a promoter. Examples of suitable promoters include, but are not limited to, a synapsin promoter, a CAG promoter, a CMV promoter, a grm6 promoter, a Pleiades promoter, a ChAT promoter, a V-glut promoter, a GAD promoter, a PV promoter, a somatostatin (SST) promoter, a neuropeptide Y (NPY) promoter, a VIP promoter, a red cone opsin promoter, rhodopsin promoter, a rhodopsin kinase promoter, vitelliform macular dystrophy 2 (VMD2) gene promoter, and an interphotoreceptor retinoid-binding protein (IRBP) gene promoter.

A composition of the present disclosure is administered to an individual in need thereof. In some instances, the composition is administered directly to or into an eye of the individual, e.g., an eye that is affected by a vision disorder. In some cases, the subject has an ocular disease selected from retinitis pigmentosa, macular degeneration, retinoschisis, and Leber's Congenital Amaurosis, and diabetic retinopathy. In some cases, the subject has experienced retinal detachment or photoreceptor loss due to trauma or head injury. In some cases, the subject has a retinal degeneration condition in which the natural light sensitivity is lost and vision is therefore compromised, but where neurons late in the retinal circuit (e.g. bipolar cells or amacrine interneurons or ganglion cells that output to the brain) are spared and can be made directly sensitive to light by introduction of the cone opsin(s).

A composition of the present disclosure can include, in addition to the one or more recombinant nucleic acids, a pharmaceutically acceptable excipient. Suitable pharmaceutically acceptable excipients are known in the art, and are described elsewhere herein. In some cases, a composition of the present disclosure is suitable for administration to a human subject; e.g., in some cases, the composition is sterile and is free of pyrogens, contaminants, and the like.

Recombinant Viral Vector

The present disclosure provides a recombinant viral vector comprising a nucleotide sequence encoding an MW-opsin and/or an LW-opsin and/or an SW-opsin polypeptide. Suitable viral expression vectors include, but are not limited to, a lentivirus vector, a herpes simplex virus (HSV) vector, an adenovirus vector, a retroviral vector, an adenoassociated virus (AAV) vector, and the like. Thus, in some cases, a recombinant viral vector comprising a nucleotide sequence encoding an MW-opsin polypeptide and/or an LW-opsin polypeptide and/or an SW-opsin polypeptide is a recombinant lentivirus vector, a recombinant HSV vector, a recombinant adenovirus vector, a recombinant retrovirus vector, or a recombinant AAV vector.

In some cases, the nucleotide sequence encoding the MW-opsin and/or the LW-opsin, and/or the SW-opsin is operably linked to a promoter that provides for expression in a retinal cell. In some cases, the nucleotide sequence is operably linked to a promoter that generally provides for expression in a eukaryotic or mammalian cell.

Suitable promoters include, but are not limited to, a CAG promoter (Miyazaki et al. (1989) Gene 79:269); a cytomegalovirus (CMV) promoter; a glutamate metabotropic receptor-6 (grm6) promoter (Cronin et al. (2014) EMBO Mol. Med. 6:1175); a Pleiades promoter (Portales-Casamar et al. (2010) Proc. Natl. Acad. Sci. USA 107:16589); a choline acetyltransferase (ChAT) promoter (Misawa et al. (1992) J. Biol. Chem. 267:20392); a vesicular glutamate transporter (V-glut) promoter (Zhang et al. (2011) Brain Res. 1377:1); a glutamic acid decarboxylase (GAD) promoter (Rasmussen et al. (2007) Brain Res. 1144:19; Ritter et al. (2016) J. Gene Med. 18:27); a cholecystokinin (CCK) promoter (Ritter et al. (2016) J. Gene Med. 18:27); a parvalbumin (PV) promoter; a somatostatin (SST) promoter; a neuropeptide Y (NPY) promoter; and a vasoactive intestinal peptide (VIP) promoter. Suitable promoters include, but are not limited to, a red cone opsin promoter, rhodopsin promoter, a rhodopsin kinase promoter, and a GluR promoter (e.g., a GluR6 promoter). Suitable promoters include, but are not limited to, a vitelliform macular dystrophy 2 (VMD2) gene promoter, and an interphotoreceptor retinoid-binding protein (IRBP) gene promoter. Also suitable for use is an L7 promoter (Oberdick et al. (1990) Science 248:223), a thy-1 promoter, a recoverin promoter (Wiechmann and Howard (2003) Curr. Eye Res. 26:25); a calbindin promoter; and a beta-actin promoter.

In some cases, a recombinant viral vector of the present disclosure comprises nucleotide sequences encoding an MW-opsin, an LW-opsin, and an SW-opsin. In some cases, the nucleotide sequences encoding an MW-opsin, an LW-opsin, and an SW-opsin are operably linked to a single promoter. In some cases, a recombinant viral vector comprises an internal ribosome entry site (IRES) between the nucleotide sequences encoding the MW-opsin and the LW-opsin, and between the nucleotide sequences encoding the LW-opsin and the SW-opsin.

In some cases, a recombinant viral vector comprising a nucleotide sequence encoding an MW-opsin and/or an LW-opsin polypeptide and/or an SW-opsin polypeptide is recombinant AAV (rAAV) vector. In some cases, the rAAV vector comprises: i) a nucleotide sequence encoding an MW-opsin and/or an LW-opsin polypeptide and/or an SW-opsin polypeptide; and ii) a nucleotide sequence encoding a variant AAV capsid protein, where the variant AAV capsid protein confers infectivity of a retinal cell and/or increased ability to cross the inner limiting membrane (ILM) in the eye, compared to a parental wild-type AAV. See, e.g., Day et al. (2014) Adv. Exp. Med. Biol. 801:687; Boye et al. (2016) J. Virol. 90:4215; Vandenberghe and Auricchio (2012) Gene Therapy 19:162; Klimczak et al. (2009) PLoS One 4:e7467; U.S. Patent Publication No. 2012/0164106; and U.S. Patent Publication No. 2016/0017295.

For example, a variant AAV capsid protein can comprise an amino acid substitution at amino acid 451 of an AAV6 capsid, or the corresponding position in another AAV serotype. In some cases, the amino acid substitution at amino acid 451 of an AAV6 capsid, or the corresponding position in another AAV serotype, is an asparagine to aspartic acid substitution. As another example, a variant AAV capsid protein can comprise an amino acid substitution at amino acid 532 of an AAV6 capsid, or the corresponding position in another AAV serotype. In some cases, the amino acid substitution at amino acid 532 of an AAV6 capsid, or the corresponding position in another AAV serotype, is an aspartic acid to asparagine substitution.

```
The AAV6 capsid can have the following amino acid
sequence:
                                    (SEQ ID NO: 10)
MAADGYLPDWLEDNLSEGIREWWDLKPGAPKPKANQQKQDDGRGLVLPGY

KYLGPFNGLDKGEPVNAADAAALEHDKAYDQQLKAGDNPYLRYNHADAEF
```

-continued
QERLQEDTSFGGNLGRAVFQAKKRVLEPFGLVEEGAKTAPGKKRPVEQSP

QEPDSSSGIGKTGQQPAKKRLNFGQTGDSESVPDPQPLGEPPATPAAVGP

TTMASGGGAPMADNNEGADGVGNASGNWHCDSTWLGDRVITTSTRTWALP

TYNNHLYKQISSASTGASNDNHYFGYSTPWGYFDFNRFHCHFSPRDWQRL

INNNWGFRPKRLNFKLFNIQVKEVTTNDGVTTIANNLTSTVQVFSDSEYQ

LPYVLGSAHQGCLPPFPADVFMIPQYGYLTLNNGSQAVGRSSFYCLEYFP

SQMLRTGNNFTFSYTFEDVPFHSSYAHSQSLDRLMNPLIDQYLYYLNRTQ

NQSGSAQNKDLLFSRGSPAGMSVQPKNWLPGPCYRQQRVSKTKTDNNNSN

FTWTGASKYNLNGRESIINPGTAMASHKDKDKFFPMSGVMIFGKESAGA

SNTALDNVMITDEEEIKATNPVATERFGTVAVNLQSSSTDPATGDVHVMG

ALPGMVWQDRDVYLQGPIWAKIPHTDGHFHPSPLMGGFGLKHPPPQILIK

NTPVPANPPAEFSATKFASFITQYSTGQVSVEIEWELQKENSKRWNPEVQ

YTSNYAKSANVDFTVDNNGLYTEPRPIGTRYLTRPL, where Asn- 451 and Asp-532 are bolded and underlined.

In some cases, the AAV capsid protein comprises
the following amino acid sequence:
(SEQ ID NO: 11)
MAADGYLPDWLEDNLSEGIREWWDLKPGAPKPKANQQKQDDGRGLVLPGY

KYLGPFNGLDKGEPVNAADAAALEHDKAYDQQLKAGDNPYLRYNHADAEF

QERLQEDTSFGGNLGRAVFQAKKRVLEPFGLVEEGAKTAPGKKRPVEQSP

QEPDSSSGIGKTGQQPAKKRLNFGQTGDSESVPDPQPLGEPPATPAAVGP

TTMASGGGAPMADNNEGADGVGNASGNWHCDSTWLGDRVITTSTRTWALP

TYNNHLYKQISSASTGASNDNHYFGYSTPWGYFDFNRFHCHFSPRDWQRL

INNNWGFRPKRLNFKLFNVQVKEVTTNDGVTTIANNLTSTVQVFSDSEYQ

LPYVLGSAHQGCLPPFPADVFMIPQYGYLTLNNGSQAVGRSSFYCLEYFP

SQMLRTGNNFTFSYTFEDVPFHSSYAHSQSLDRLMNPLIDQYLYYLNRTQ

DQSGSAQNKDLLFSRGSPAGMSVQPKNWLPGPCYRQQRVSKTKTDNNNSN

FTWTGASKYNLNGRESIINPGTAMASHKDKNKFFPMSGVMIFGKESAGA

SNTALDNVMITDEEEIKATNPVATERFGTVAVNLQSSSTDPATGDVHVMG

ALPGMVWQDRDVYLQGPIWAKIPHTDGHFHPSPLMGGFGLKNPPPQILIK

NTPVPANPPAEFSATKFASFITQYSTGQVSVEIEWELQKENSKRWNPEVQ

YTSNYAKSANVDFTVDNNGLYTEPRPIGTRYLTRPL.

The present disclosure provides a method of delivering an MW-opsin and/or an LW-opsin and/or an SW-opsin to a retinal cell, the method comprising administering a recombinant viral vector of the present disclosure (or a viral particle comprising the recombinant viral vector) to the eye of an individual. Following administration of the recombinant viral vector (or viral particle comprising the recombinant viral vector), the MW-opsin is produced in the retinal cell.

The present disclosure provides a method of enhancing or restoring visual function in an individual, the method comprising administering a recombinant viral vector of the present disclosure (or a viral particle comprising the recombinant viral vector) to the eye of an individual. Following administration of the recombinant viral vector (or viral particle comprising the recombinant viral vector), the MW-opsin and/or an LW-opsin and/or an SW-opsin is produced in the retinal cell. Production of the MW-opsin and/or the LW-opsin and/or the SW-opsin in the retinal cell provides for enhanced or restored visual function in the individual.

The present disclosure provides a pharmaceutical composition comprising: a) a recombinant viral vector of the present disclosure, or a viral particle comprising the recombinant viral vector; and b) a pharmaceutically acceptable excipient. Suitable pharmaceutically acceptable excipients are described above.

The present disclosure provides a method of delivering an MW-opsin and/or an LW-opsin and/or an SW-opsin to a retinal cell, the method comprising administering a pharmaceutical composition comprising a recombinant viral vector (or a viral particle comprising the recombinant viral vector) to the eye of an individual. Following administration of the recombinant viral vector (or viral particle comprising the recombinant viral vector), the MW-opsin and/or an LW-opsin and/or an SW-opsin is produced in the retinal cell.

The present disclosure provides a method of enhancing or restoring visual function in an individual, the method comprising administering a pharmaceutical composition comprising a recombinant viral vector of the present disclosure (or a viral particle comprising the recombinant viral vector) to the eye of an individual. Following administration of the recombinant viral vector (or viral particle comprising the recombinant viral vector), the MW-opsin and/or an LW-opsin and/or an SW-opsin is produced in the retinal cell. Production of the MW-opsin and/or an LW-opsin and/or an SW-opsin in the retinal cell provides for enhanced or restored visual function in the individual.

A recombinant expression vector of the present disclosure (or a viral particle comprising the recombinant viral vector) can be administered to an individual in need thereof by any of a variety of routes of administration. Suitable routes of administration include, e.g., periocular, intraocular, intravitreal, subconjunctive, retrobulbar, into the sclera, and intercameral. In some cases, recombinant expression vector of the present disclosure (or a viral particle comprising the recombinant viral vector) is delivered by intravitreal injection. In some cases, a recombinant expression vector of the present disclosure (or a viral particle comprising the recombinant viral vector) is delivered intraocularly. In some cases, recombinant expression vector of the present disclosure (or a viral particle comprising the recombinant viral vector) is delivered via sub-retinal injection.

Individuals suitable for treatment with a method of the present disclosure include individuals having reduced visual function due to loss of rod and cone photoreceptors. In some cases, the individual has an inherited retinal degenerative disease. In some cases, the individual has an ocular disease selected from retinitis pigmentosa, macular degeneration, retinoschisis, and Leber's Congenital Amaurosis, and diabetic retinopathy. In some cases, the individual has an age-related retinal degenerative disease. In some cases, the individual has age-related macular degeneration.

EXAMPLES OF NON-LIMITING ASPECTS OF THE DISCLOSURE

Aspects, including embodiments, of the present subject matter described above may be beneficial alone or in combination, with one or more other aspects or embodiments. Without limiting the foregoing description, certain non-limiting aspects of the disclosure numbered 1-54 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A method of restoring or enhancing visual function in an individual, the method comprising administering to the individual a nucleic acid comprising a nucleotide sequence encoding a medium wavelength opsin (MW-opsin) and/or a long wavelength opsin (LW-opsin) and/or a short wavelength opsin (SW-opsin), wherein said administering provides for expression of the MW-opsin and/or the LW-opsin and/or the SW-opsin in a retinal cell in the individual and restoration or enhancement of visual function.

Aspect 2. The method of aspect 1, wherein the MW-opsin comprises an amino acid sequence having at least 85%, at least 90%, at least 95%, at least 98%, at least 99%, or 100%, amino acid sequence identity to the amino acid sequence set forth in SEQ ID NO:1; wherein the LW-opsin comprises an amino acid sequence having at least 85%, at least 90%, at least 95%, at least 98%, at least 99%, or 100%, amino acid sequence identity to the amino acid sequence set forth in SEQ ID NO:4, and wherein the SW-opsin comprises an amino acid sequence having at least 85%, at least 90%, at least 95%, at least 98%, at least 99%, or 100%, amino acid sequence identity to the amino acid sequence set forth in SEQ ID NO:5.

Aspect 3. The method of aspect 1, wherein the SW-opsin comprises an amino acid sequence having at least 87%, at least 90%, at least 95%, at least 98%, at least 99%, or 100%, amino acid sequence identity to the human SW-opsin amino acid sequence set forth in SEQ ID NO:5 or having at least 87% amino acid sequence identity to the mouse SW-opsin amino acid sequence set forth in SEQ ID NO:6.

Aspect 4. The method of aspect 1, comprising administering to the individual: i) a first nucleic acid comprising a nucleotide sequence encoding an SW-opsin comprising an amino acid sequence having at least 87%, at least 90%, at least 95%, at least 98%, at least 99%, or 100%, amino acid sequence identity to the human SW-opsin amino acid sequence set forth in SEQ ID NO:5; and ii) a second nucleic acid comprising a nucleotide sequence encoding an SW-opsin comprising an amino acid sequence having at least 87%, at least 90%, at least 95%, at least 98%, at least 99%, or 100%, amino acid sequence identity to the mouse SW-opsin amino acid sequence set forth in SEQ ID NO:6.

Aspect 5. The method of aspect 1, wherein the SW-opsin is a chimeric SW-opsin comprising mouse SW-opsin intracellular domains and human SW-opsin transmembrane domains.

Aspect 6. The method of aspect 5, wherein the chimeric SW-opsin comprises an amino acid sequence having at least 90%, at least 95%, at least 98%, at least 99%, or 100%, amino acid sequence identity to the chimeric SW-opsin amino acid sequence set forth in SEQ ID NO:7.

Aspect 7. The method of any one of aspects 1-6, wherein expression of the MW-opsin and/or the LW-opsin and/or the SW-opsin in the retinal cell provides for patterned vision and image recognition by the individual.

Aspect 8. The method of aspect 7, wherein the image recognition is of a static image or a pattern.

Aspect 9. The method of aspect 7, wherein the image recognition is of a moving image or a pattern.

Aspect 10. The method of any one of aspects 1-9, wherein expression of the MW-opsin and/or the LW-opsin and/or the SW-opsin in the retinal cell provides for image recognition at a light intensity of from about $10^{-4}$ W/cm$^2$ to about 1 W/cm$^2$.

Aspect 11. The method of any one of aspects 1-9, wherein expression of the MW-opsin and/or the LW-opsin and/or the SW-opsin in the retinal cell provides for image recognition at a light intensity that is at least 10-fold lower than the light intensity required to provide for image recognition by an individual expressing a channelrhodopsin polypeptide in a retinal cell.

Aspect 12. The method of any one of aspects 1-9, wherein expression of the MW-opsin and/or the LW-opsin and/or the SW-opsin in the retinal cell provides for kinetics that are at least 2-fold faster than the kinetics conferred on a retinal cell by a rhodopsin polypeptide.

Aspect 13. The method of any one of aspects 1-12, wherein the nucleic acid is a recombinant expression vector.

Aspect 14. The method of aspect 13, wherein the recombinant expression vector is a recombinant viral vector.

Aspect 15. The method of aspect 14, wherein the recombinant viral vector is an adeno-associated viral vector, a lentiviral vector, a herpes simplex virus vector, or a retroviral vector.

Aspect 16. The method of any one of aspects 1-15, wherein the nucleotide sequence is operably linked to a transcriptional control element that is functional in a retinal cell.

Aspect 17. The method of aspect 16, wherein the transcriptional control element is a retinal cell-specific promoter.

Aspect 18. The method of aspect 17, wherein the promoter is a synapsin promoter, a CAG promoter, a CMV promoter, a grm6 promoter, a Pleiades promoter, a ChAT promoter, a V-glut promoter, a GAD promoter, a PV promoter, a somatostatin (SST) promoter, a neuropeptide Y (NPY) promoter, a VIP promoter, a red cone opsin promoter, rhodopsin promoter, a rhodopsin kinase promoter, vitelliform macular dystrophy 2 (VMD2) gene promoter, or an interphotoreceptor retinoid-binding protein (IRBP) gene promoter.

Aspect 19. The method of any one of aspects 1-18, wherein said administering is via intraocular injection.

Aspect 20. The method of any one of aspects 1-18, wherein said administering is via intravitreal injection.

Aspect 21. The method of any one of aspects 1-18, wherein said administering is via subretinal injection.

Aspect 22. The method of any one of aspects 1-21, wherein the individual has an ocular disease selected from retinitis pigmentosa, macular degeneration, retinoschisis, and Leber's Congenital Amaurosis, and diabetic retinopathy.

Aspect 23. The method of any one of aspects 1-21, wherein the individual has experienced retinal detachment or photoreceptor loss due to trauma or head injury.

Aspect 24. The method of any one of aspects 1-23, wherein the nucleic acid is complexed with a nanoparticle.

Aspect 25. A recombinant viral vector comprising a nucleotide sequence encoding a medium wavelength opsin (MW-opsin) and/or a long wavelength opsin (LW-opsin) and/or a short wavelength opsin (SW-opsin).

Aspect 26. The recombinant viral vector of aspect 25, wherein the viral vector is an adenoassociated viral vector.

Aspect 27. The recombinant viral vector of aspect 25 or aspect 26, wherein the MW-opsin comprises an amino acid sequence having at least 85%, at least 90%, at least 95%, at least 98%, at least 99%, or 100%, amino acid sequence identity to the amino acid sequence set forth in SEQ ID NO:1; wherein the LW-opsin comprises an amino acid sequence having at least 85%, at least 90%, at least 95%, at least 98%, at least 99%, or 100%, amino acid sequence identity to the amino acid sequence set forth in SEQ ID NO:4, and wherein the SW-opsin comprises an amino acid sequence having at least 87%, at least 90%, at least 95%, at least 98%, at least 99%, or 100%, amino acid sequence identity to the amino acid sequence set forth in one of SEQ ID NOs:5-7.

Aspect 28. The recombinant viral vector of any one of aspects 25-27, wherein the nucleotide sequence is operably linked to a promoter.

Aspect 29. The recombinant viral vector of aspect 28, wherein the promoter is a synapsin promoter, a CAG promoter, a CMV promoter, a grm6 promoter, a Pleiades promoter, a ChAT promoter, a V-glut promoter, a GAD promoter, a PV promoter, a somatostatin (SST) promoter, a neuropeptide Y (NPY) promoter, a VIP promoter, a red cone opsin promoter, rhodopsin promoter, a rhodopsin kinase promoter, vitelliform macular dystrophy 2 (VMD2) gene promoter, or an interphotoreceptor retinoid-binding protein (IRBP) gene promoter.

Aspect 30. The recombinant viral vector of any one of aspects 25-29, wherein the recombinant viral vector is a recombinant AAV vector, wherein the recombinant AAV vector comprises a nucleotide sequence encoding a variant capsid polypeptide that confers increased infectivity of a retinal cell and/or confers increased ability to cross the inner limiting membrane, compared to a wild-type AAV capsid.

Aspect 31. A pharmaceutical composition comprising:
a) the recombinant viral vector of any one of aspects 25-30; and
b) a pharmaceutically acceptable excipient.

Aspect 32. A method of restoring or enhancing visual function in an individual, the method comprising administering to the individual the recombinant viral vector of any one of aspects 25-30, or the pharmaceutical composition of aspect 31, wherein said administering provides for expression of the MW-opsin and/or the LW-opsin and/or the SW-opsin in a retinal cell in the individual and restoration or enhancement of visual function.

Aspect 33. A chimeric SW-opsin comprising intracellular portions of a mouse SW-opsin comprising an amino acid sequence having at least 87%, at least 90%, at least 95%, at least 98%, at least 99%, or 100%, amino acid sequence identity to the amino acid sequence set forth in SEQ ID NO:6, and comprising transmembrane portions of a human SW-opsin comprising an amino acid sequence having at least 87%, at least 90%, at least 95%, at least 98%, at least 99%, or 100%, amino acid sequence identity to the amino acid sequence set forth in SEQ ID NO:5.

Aspect 34. The chimeric SW-opsin of aspect 33, comprising an amino acid sequence having at least 90% amino acid sequence identity to the amino acid sequence set forth in SEQ ID NO:7.

Aspect 35. A recombinant expression vector comprising a nucleotide sequence encoding the chimeric SW-opsin of aspect 33 or aspect 34.

Aspect 36. A composition comprising:
a) the recombinant expression vector of aspect 35; and
b) a pharmaceutically acceptable excipient.

Aspect 37. A composition comprising one or more recombinant nucleic acid vectors comprising one or more nucleotide sequences encoding one or more cone opsins, wherein, when said one or more nucleotide sequences is expressed in an eye of a subject in need thereof, said subject can distinguish between an image comprising a vertical line and an image comprising a horizontal line in a spatial pattern discrimination assay.

Aspect 38. A composition comprising one or more recombinant nucleic acid vectors comprising one or more nucleotide sequences encoding one or more cone opsins, wherein, when said one or more nucleotide sequences is expressed in an eye of a subject in need thereof, said subject can distinguish between an image comprising a static line and an image comprising a moving line in a spatial pattern discrimination assay.

Aspect 39. A composition comprising one or more recombinant nucleic acid vectors comprising one or more nucleotide sequences encoding one or more cone opsins, wherein, when said one or more nucleotide sequences is expressed in an eye of a subject in need thereof, said subject can distinguish between flashing light and constant light in a temporal light pattern assay.

Aspect 40. A composition comprising one or more recombinant nucleic acid vectors comprising one or more nucleotide sequences encoding one or more cone opsins, wherein, when said one or more nucleotide sequences is expressed in an eye of a subject in need thereof, said subject can recognize an image at a light intensity of from about $10^{-4}$ $W/cm^2$ to about 10 $W/cm^2$ in an image recognition assay.

Aspect 41. A composition comprising one or more recombinant nucleic acid vectors comprising one or more nucleotide sequences encoding one or more cone opsins, wherein, when said one or more nucleotide sequences is expressed in an eye of a subject in need thereof, said subject can distinguish between an area with white light and an area without white light in a light avoidance assay.

Aspect 42. The composition of any one of aspects 37-41, wherein the one or more cone opsins is selected from the group consisting of: a) an MW-opsin comprising an amino acid sequence having at least 85% amino acid sequence identity to the amino acid sequence set forth in SEQ ID NO:1; b) an LW-opsin comprising an amino acid sequence having at least 85% amino acid sequence identity to the amino acid sequence set forth in SEQ ID NO:4; c) an SW-opsin comprising an amino acid sequence having at least 85% amino acid sequence identity to the amino acid sequence set forth in SEQ ID NO:5; and d) a chimeric SW-opsin comprising: i) intracellular portions of a mouse SW-opsin comprising an amino acid sequence having at least 87% amino acid sequence identity to the amino acid sequence set forth in SEQ ID NO:6; and ii) transmembrane portions of a human SW-opsin comprising an amino acid sequence having at least 87% amino acid sequence identity to the amino acid sequence set forth in SEQ ID NO:5.

Aspect 43. The composition of any one of aspects 37-41, wherein the one or more recombinant nucleic acid vectors comprise one or more nucleotide sequences encoding 2 different cone opsins.

Aspect 44. The composition of any one of aspects 37-41, wherein the one or more recombinant nucleic acid vectors comprise one or more nucleotide sequences encoding 3 different cone opsins.

Aspect 45. The composition of any one of aspects 37-44, wherein the one or more recombinant nucleic acid vectors are an adeno-associated viral vector, a lentiviral vector, a herpes simplex virus vector, or a retroviral vector.

Aspect 46. The composition of any one of aspects 37-44, wherein the one or more recombinant nucleic acid vectors are recombinant adeno-associated virus vectors.

Aspect 47. The composition of aspect 46, wherein the recombinant AAV vector comprises a nucleotide sequence encoding a variant capsid polypeptide that confers increased infectivity of a retinal cell and/or confers increased ability to cross the inner limiting membrane, compared to a wild-type AAV capsid.

Aspect 48. The composition of any one of aspects 37-47, wherein the one or more nucleotide sequences are operably linked to a promoter.

Aspect 49. The composition of aspect 48, wherein the promoter is a synapsin promoter, a CAG promoter, a CMV promoter, a grm6 promoter, a Pleiades promoter, a ChAT promoter, a V-glut promoter, a GAD promoter, a PV promoter, a somatostatin (SST) promoter, a neuropeptide Y (NPY) promoter, a VIP promoter, a red cone opsin promoter, rhodopsin promoter, a rhodopsin kinase promoter, vitelliform macular dystrophy 2 (VMD2) gene promoter, or an interphotoreceptor retinoid-binding protein (IRBP) gene promoter.

Aspect 50. The composition of any one of aspects 37-49, wherein the subject has an ocular disease selected from retinitis pigmentosa, macular degeneration, retinoschisis, and Leber's Congenital Amaurosis, and diabetic retinopathy.

Aspect 51. The composition of any one of aspects 37-49, wherein the subject has experienced retinal detachment or photoreceptor loss due to trauma or head injury.

Aspect 52. The composition of any one of aspects 37-51, wherein the composition comprises a pharmaceutically acceptable excipient.

Aspect 53. The composition of aspect 52, wherein the pharmaceutically acceptable excipient comprises saline.

Aspect 54. The composition of any one of aspects 37-53, wherein the composition is sterile.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Effect of Expression of MW-Opsin in Retinal Cells In Vitro and In Vivo Inherited and age-related retinal degenerative diseases cause progressive loss of rod and cone photoreceptors, leading to complete blindness. Despite loss of the light-sensing cells required for vision, downstream neurons of the inner retina survive in a functional state, providing a target for optogenetic therapy. To date, optogenetic approaches have encountered two major limitations: very low light sensitivity in microbial opsins and very slow kinetics in retinal opsins. The data presented below show that the vertebrate medium wavelength cone opsin (MW-opsin) overcomes these limitations and supports patterned vision under low light. Expression of MW-opsin in retinal ganglion cells (RGCs) of blind rd1 mice introduces an ON transient light response that is highly sensitive to light with fast kinetics. MW-opsin restores photo-avoidance with similar light sensitivity to that seen in wildtype animals, three orders of magnitude below level required for microbial opsins, and on par with rhodopsin. MW-opsin enables rd1 animals to discriminate both between different temporal light patterns and between different spatial light patterns, even when the spatial patterns are in motion. In contrast, rd1 animals with rhodopsin in RGCs are incapable of both temporal and spatial discrimination. Strikingly, the MW-opsin light response adapts to ambient light over an ~1,000-fold range. Thus, MW-opsin combines speed, sensitivity and adaptation to restore adjustable patterned vision under realistic light intensities. LW-opsin and SW-opsin also support vision discrimination between static visual patterns, suggesting that the cone opsins can individually restore natural monochromatic vision and that, in combination, they may restore color vision.

Materials and Methods

Animals and AAVs

Mouse experiments were conducted under the express approval of the University of California Animal Care and Use Committee. wt mice (C57BL/6J) and rd1 mice (C3H) were purchased from the Jackson Laboratory and housed on a 12-h light/dark cycle with food and water ad libitum. cDNA encoding vertebrate medium wave cone opsin or rhodopsin was linked with yellow florescent protein (YFP) gene on the c-terminus and inserted in an established viral cassette under control of the human synapsin promoter (hsyn-1). Gene and promoter was flanked by inverted terminal repeat domains, stabilized by a polyadenylation signal sequence (polyA) with a woodchuck hepatitis post-transcriptional regulatory element (WPRE) and packaged in the AAV 2/2-4YF capsid. The titer of AAVs was determined via qPCR relative to inverted repeat domains standard and reported to contain $10^{10}$-$10^{12}$ viral genomes. AAVs were produced as previously described[15]. Vector was delivered in a 2 µl volume to the vitreous of the rd1 mouse eye via microinjection using a blunt 32-gauge Hamilton syringe though an incision made posterior of the or a serrata using a sharp 30-gauge needle. rAAV injections were at p30-p60 and in vivo and in vitro experiments at p90-p160. Mice were anesthetized with IP ketamine (72 mg/kg) and xylazine (64 mg/kg). Eyes were anesthetized with proparacaine (0.5%) and pupils were dilated with phenylephrine (2.5%) and tropicamide (1%).

Electrophysiology and Light Stimulation

HEK cell recordings were performed as previously described[15,51,52]. Briefly, cells were clamped in whole cell mode in a high external potassium solution (50 mM), and held at $V_H = -80$ mV, to provide an inward driving force for potassium. 5-10 s pulses of light were given at low intensity (1 mW cm$^{-2}$) at 535 nm (for MW-opsin) or 500 nm (for rhodopsin).

MEA recordings were performed on wt (C57BL/6J) mice, and untreated and treated rd1 mice at >p90 6-10 wks following AAV injection experimental retina were excised from the eye under dim red light, mounted on 4 µm cell membranes and placed in an incubator (35° C.) for 30 min and perfused with exogenous chromophore 9-cis retinal. Retinal tissue was placed ganglion cell side down[53] in the recording chamber (pMEA 100/30iR-Tpr; Multi Channel Systems) of a 60-channel MEA system with a constant perfusion of Ames recording media (32° C.). A Multi Channel Systems harp weight (Scientific Instruments—Slice grids) was placed on the retina to prevent movement and vacuum was applied to the retina using a pump (perforated MEA1060 system with CVP; Multi Channel Systems), improving electrode-to-tissue contact and to provide consistent signal-to-noise ratios across retinas. Additionally, a dry crystal of exogenous chromophore 9-cis retinal was dissolved in µl 100% ethanol under dark conditions. Dissolved retinal was then added to 100 µl matrigel on ice and added to the top of the harp, just above the retina, in order to supply a continues supply of chromophore. Additionally, 9-cis retinal was dissolved in the recording solution and perfused consistently into the recording chamber. Further detail regarding MEA methods are previously detailed in Gaub. et al. (2015)[15]. Illumination in vitro was by a 300-W mercury arc lamp (DG-4; Sutter Instruments) with a 535/50 nm bandpass filter for MW-opsin or a 510/89 nm bandpass filter for Rhodopsin. Light intensity was controlled by modifying the light source duty cycle or by using neutral density filters and ranged from 0.038 µW cm$^{-2}$ to 38.2 mW/cm$^2$. Relative comparisons with natural light intensities were obtained in various environments using direct light measurement with a power meter (Thorlabs). Spectral component of white light measured using a CCD Spectrometer with Fourier Transform Optical Spectrum Analyzer software (Thorlabs).

MEA Data Acquisition & Analysis

Retinal activity on the MEA was sampled at 25 kHz filtered between 100 and 2,000 Hz and recorded using MC_rack software (Multi Channel Systems). Voltage traces were converted to spike trains offline and the spikes recorded at each electrode were sorted into single units, which are defined as "cells," via principal component analysis using Offline Sorter (Plexon-64 bit) with each electrode commonly identifying 1-3 cells. Single-unit spike clusters were exported to MATLAB (MathWorks) and were analyzed and graphed with custom software. All firing rates were extracted from traces averaged over 3-10 light response cycles unless otherwise specified, details of which are denoted in figure legends. Responses across cells and across retina were normalized using the Light Response Index (LRI) adopted from Tochitsky, I., et al. (2014)[37] and Gaub et al. (2014)[47] (LRI=(peak firing rate in the light—average firing rate in dark)/peak firing rate in the light+average firing rate in dark). Under experiments where conditions were changed within retina (light sensitivity, light and dark adaption sensitivity, and dependence of response on flash duration) the responses were normalized to the peak of the greatest response from baseline and channels were tracked across all recording parameters. All curve fitting and kinetic analysis was performed in Clampfit 10.6 (Molecular Devices). Cells were defined as "responders" if the LRI satisfied the condition LRI>0.1 or LRI<−0.1. The width of response at half maximum of peak from baseline was determined with custom MATLAB (MathWorks) analysis software, which interpolated the traces of individual cells and applied smoothing before identifying FWHM. Intensity-response relations were fit with a single Boltzmann and normalized to the fit between 0 and 1.

Comparing Light Sensitivity of Optogenetic Probes

Figure 7:
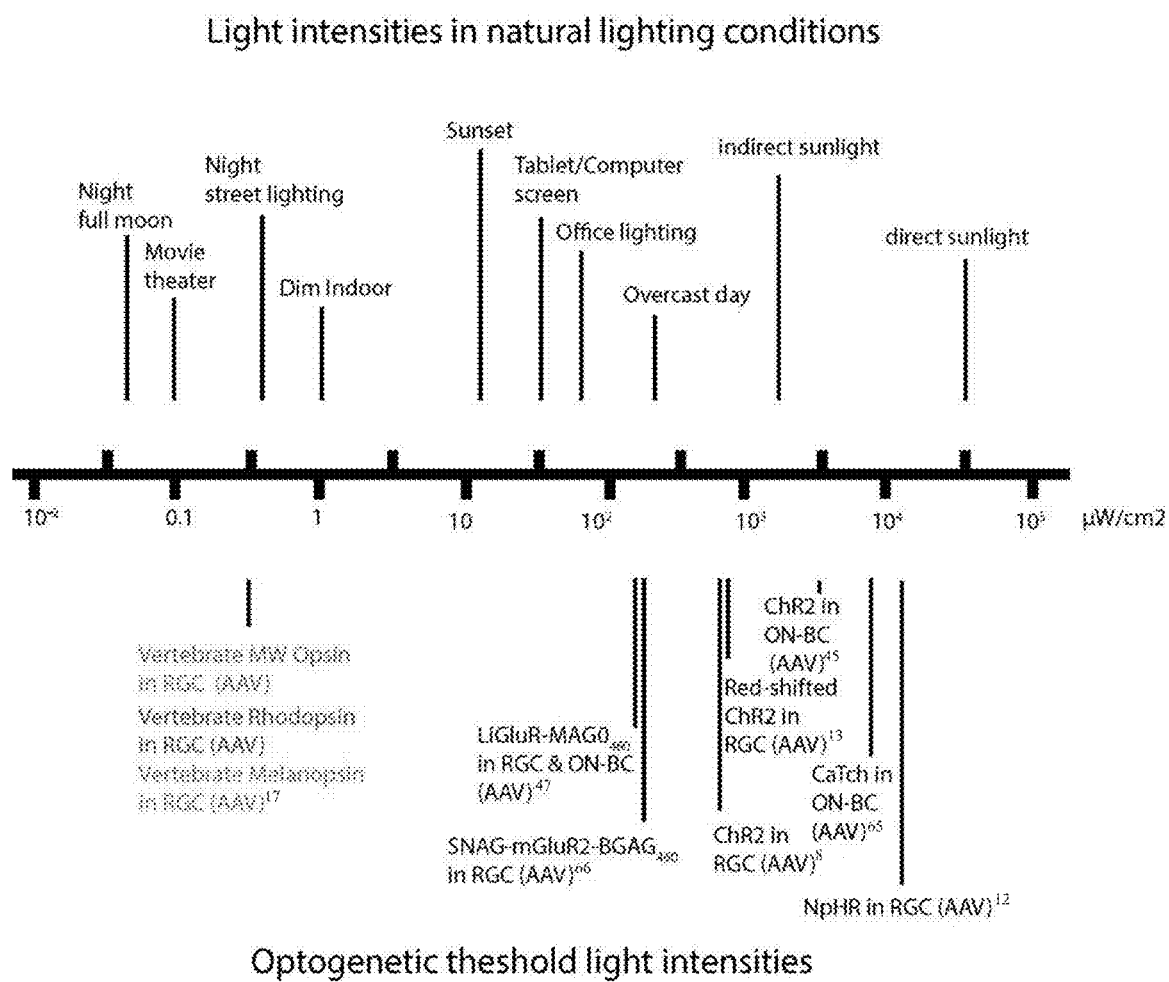
FIG. 7 depicts the threshold response of optogenetic systems in blind retinas compared to normal vision.

The natural sensitivity of human vision covers a wide range, from scotopic (dim $10^4$-$10^{11}$ photons cm$^{-2}$ s$^{-1}$) to photopic (bright $10^{10}$-$10^{17}$ photons cm$^{-2}$ s$^{-1}$), allowing perception under dynamic lighting conditions. To relate the sensitivity of MW-opsin to that of other optogenetic systems and of normal vision, experiments were performed that measured natural light intensities under various outdoor and indoor conditions using a portable power meter (Thorlabs), compared them to experimental paradigms and to light sensitivity thresholds (lowest measurable light responses) reported in the literature using monochromatic wavelengths of light at or near peak functional maxima in retinal explants isolated from rd1 mice to which the optogenetic probe was delivered via AAV transfection (FIG. 7).

Electrophysiology and Light Stimulation for In Vivo Brain Recordings

In vivo recordings were performed as previously described by Veit et. al. (2017)[58]. Mice were anesthetized with isoflurane (2.5% vapor concentration). The scalp was removed, the fascia retracted, and the skull lightly etched with a 27 gauge needle. Following application of Vetbond to the skull surface, a custom stainless steel headplate was fixed to the skull with dental cement (Metabond). Mice were allowed to recover from surgery for at least 2 days. Then mice were habituated for 2-5 days to head-fixation on a free-spinning circular treadmill. On the day of recording, mice were briefly anesthetized with isoflurane (2%), the skull over V1 was thinned, and a small (<250 µm) craniotomy was opened over the primary visual cortex with a fine needle. A16-channel linear electrode array with 25 micron spacing (NeuroNexus, Alx16-5 mm-25-177-A16) was guided into the brain using a micromanipulator (Sensapex) and a stereomicroscope (Leica). Electrical activity was amplified and digitized at 30 kHz (Spike Gadgets), and stored on a computer hard drive. The cortical depth of each electrical contact was determined by zeroing the bottom contact to the surface of the brain. The electrode was inserted close to perpendicular to the brain surface.

Visual stimuli were generated with Psychophysics Toolbox[59] running on an Apple Mac Mini and were presented on a gamma corrected 23-inch Eizo FORIS FS2333 LCD display with a 60-Hz refresh rate. The monitor was centered 15 cm from the right eye of the mouse covering roughly 108 by 61 degrees of visual angle. Mice were dark adapted for 7-10 minutes before every block of recordings. Two different stimulation paradigms were used: 1) Contrast: Mice were presented with 500 ms full screen flashes at 0.5 Hz of four different luminance levels (15, 25, 50 and 100% of maximal luminance) that were repeated 10 times in different random orders. 2) Flicker: Mice were presented with 20 500 ms full screen flashes (maximum luminance 116 µW cm$^{-2}$) at 0.0167 Hz (one per minute) or 100 flashes at 0.5, 1, 2 and 4 Hz in separate blocks.

In Vivo Cortical Recording Data, Acquisition and Analysis

Figures 19A, 19B, 19C, 19D, 19E:
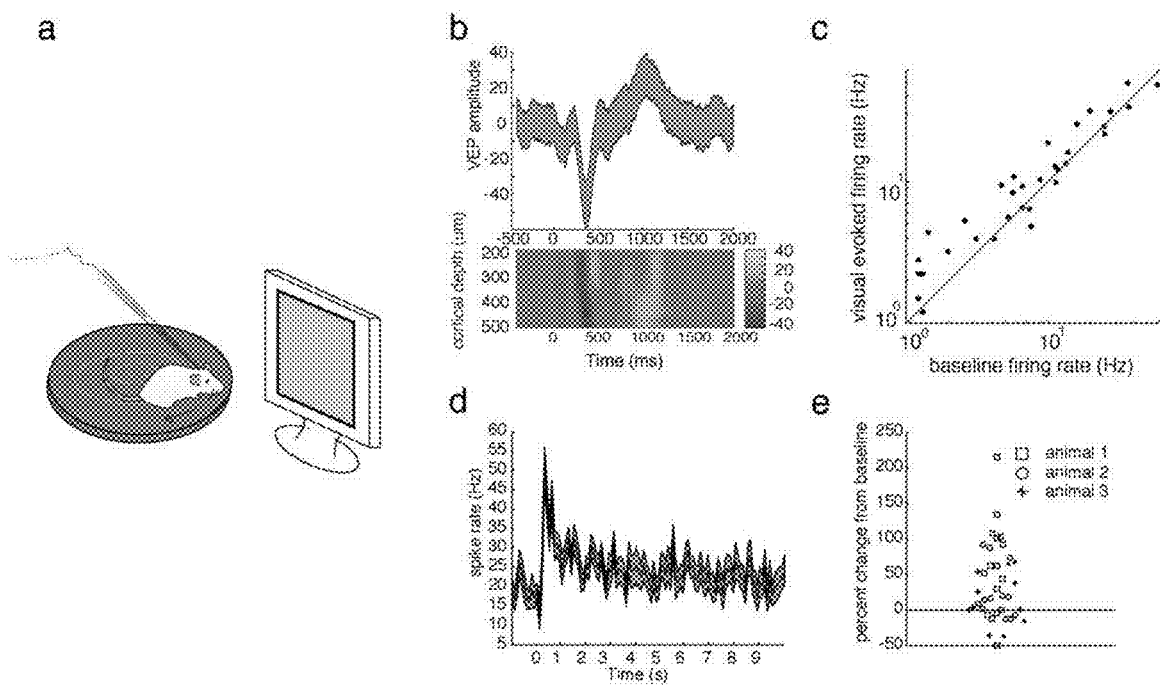
FIG. 19A-19E depict the in vivo light response in V1 of a rd1 mouse expressing MW-opsin.
Figures 20A, 20B:
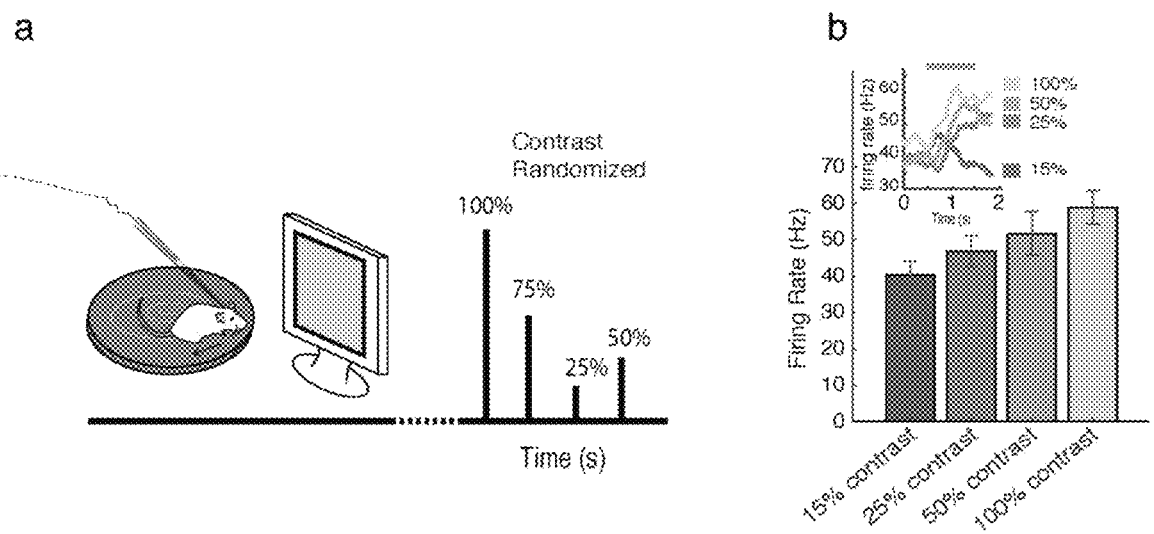
FIG. 20A-20B depict contrast detection in vivo in an MW-opsin expressing rd1 mouse.

Spiking activity was extracted by filtering the raw signal between 800 and 7000 Hz. Spike detection was performed using the UltraMega Sort package[60]. Detected spike waveforms were sorted using the MClust package (http://redishlab.neuroscience.umn.edu/MClust/MClust.html). Waveforms were first clustered automatically using KlustaKwik and then manually corrected to meet criteria for further analysis. Units with more than 2% of their individual waveforms violating a refractory period of 2 ms were classified as multi-units. The depth of each unit was assigned based on the calculated depth of the electrode on the array that exhibited its largest amplitude sorted waveform. Firing rates were computed by counting spikes in a two second window starting 250 ms after the onset of the visual stimulus for FIG. 20b and in a 5 s window starting directly after stimulus onset for FIG. 21c. Traces for Peri-stimulus time histograms (PSTHs) were generated by binning the spiking response into either 20 ms (FIG. 19) 50 ms (FIG. 20) or 25 ms (FIG. 21) bins and smoothing the resulting traces with a moving average filter. For FIG. 21, modulation amplitude was calculated on trial averaged spiking responses binned at 25 ms in a 2, 1, 0.5 or 0.25 s window for 0.5, 1, 2 and 4 Hz flicker respectively. Corresponding baseline modulation amplitudes were generated from trial averaging the same number of same-length windows from before the onset of the first visual stimulus (during the dark adaptation period). Local field potentials were extracted by low pass filtering the raw signal, sampled at 30 kHz, below 200 Hz and subsequent down-sampling to 1 kHz.

Statistics

To assess statistical significance of MEA recordings, nonparametric two-tailed Mann-Whitney U tests where applied. For learned dark avoidance behavior and the learned pattern discrimination behaviors significance was determined in two ways. (1) Significance for behavioral performance was calculated using two-tailed unpaired student's t-tests with Bonferroni correction when applicable. Significance was also determined by computing the proportion of successful performances (2). A success was defined as greater than the sum of the control group average and one S.D, and a failure was any value that did not achieve this criteria. Success ratios were then calculated for each condition. To determine significance in differences between conditions a pairwise contingency table was then constructed, and a Two-Sided Pearson's Chi-Square Test was initially conducted. To correct for conditions with a small n, a One-Sided Fisher's Exact Test was also conducted. FIG. 11 (Table 1).

Tissue Preparation and Immunohistochemistry

Mice >4-6 wks post-AAV2/2-hsyn-MW-coneopsin-YFP treatment were sacrificed, eyes were fixed in 4% paraformaldehyde (Ted Pella) (30 min), retinas were removed and washed thoroughly using PBS and flat mounted on slides using Vectashield (Vector Laboratories) medium impregnated with DAPI (cell nuclei stain—blue). For retinal sections, whole mounts were embedded in agarose (Sigma) and sectioned transverse using a vibratome (Leica Microsystems) at medium speed, maximum vibration, and 180-µm thickness. Retinal tissues used for immunohistochemistry on retinal cryosections or whole mounts were processed and examined by confocal microscopy (Leica TCS SP5; Leica Microsystems).

Passive Avoidance—Open Field Test

The open field test was performed as described previously[16,47]. Briefly, a two-compartment (light & dark) shuttle box (Colbourn Instruments) allows the mouse to move freely through a small opening that connects the two compartments. The light compartment was illuminated by a LCD panel over the compartment. White light as well as wavelengths of 535 nm and 460 nm were used at light intensity of ~100 µW cm$^{-2}$ (white light) & 0.5-25 µW cm$^{-2}$ (blue and green light) was homogeneously distributed throughout the floor. Day 1—mice were transferred into the testing box, and allowed to habituate to the new environment with their littermates for 45 min. Mice were then retuned in to their home cage and then tested individually. Day 2—Mice were placed in the light compartment and were given a maximum of 3 min to discover that there is a second compartment. A 15-min trial began when they crossed into the dark compartment, and time spent in the light was recorded. Mice that crossed the opening only once and stayed in the dark compartment for entire time were disqualified. For adaptation experiments mice were pre-exposed to 1 hr of white light (1 mW cm$^{-2}$) or dark exposure conditions then immediately performed the open field test. Animals movements were tracked using IR sensors on the shuttle box. Time spent on either side was collected and analyzed using the Graphic State, and Graphic State RT programs (Colbourn Instruments).

Visually Cued Fear-Conditioning Paradigm

Fear conditioning experiments were performed using Colbourn shock chambers-Colbourn Habitest chamber with test cage (Coulbourn Instruments, PA) with an LED screen mounted to the ceiling. On day 1—animals were brought into the testing room in their home cages and then individually acclimated to clean Colbourn shock chambers for 30 minutes. On day 2-3 animals were subjected to paired or unpaired light cued fear conditioning, consisting of 5 minutes habituation to the chamber (dark) followed by three shock trials at 0.7 mA over a span of 15 min. For paired trials, the transition from either static or flashing (2 Hz) on the LCD coincided with a brief foot shock at a 2 seconds intershock-interval (for 10 sec). For unpaired trials, animals also received shocks but were independent of the stimulus transition. These brief, low current shocks provided the minimal aversive stimuli to create a fearful memory associated with patterned light. On day 4 the flooring of box was replaced with plastic instead of shock grating. Mice were habituated to the chamber for 5 minutes and subjected to the same light stimulation protocol as on day 2 & 3 but without shock. Freezing behavior in anticipation of the shock was recorded by Colbourn's FreezeFrame software and normalized to movement behavior gathered before the stimulation. The performance was then compared between paired and unpaired cohorts in order to determine if a fear response was conditioned to the stimulus transition.

Modified Active Avoidance Protocol

Avoidance protocols were done using Colbourn shuttle box (H10-11M-SC) Colbourn Habitest Isolation Cubicle (H10-24), and the Graphic State and Graphic State RT software (Colbourn Instruments, PA). On Day 1—animals were acclimated to darkened procedure room for 30 minutes in their home cages, followed by individual acclimation to darkened shuttle box until animals were non-fearful and spending approximately equal amounts of time on each side of shuttle box (exploratory behavior). On day 2-3 iPad screens were mounted in shuttle cage wall and displayed two distinct images of equal shape, size, light intensity. Each run began when the animal moved to the other side of shuttle box from where it was placed. Each run was 15 minutes long. The aversive image side was paired with a foot shock of 0.7 mA at intervals of 5 seconds until the animal returned to the "safe" side. Any animal remaining on the aversive side for more than 60 seconds was removed from cage and that run was discarded. On Day 4 the light patterns were reversed (so the aversive screen is on what was formerly the "safe" side) to avoid a bias for location rather than pattern. Additionally, the flooring of the cage is replaced with plastic instead of shock grating. This ensures that the only related association with training day is the light stimuli. Again, animals were run for 15 minutes and time spent on each side was recorded. For light adaptation experiments, the same protocol was followed except that on day 4, the recall phase was preceded with either a light (65 W white bulb) or dark adaptation phase for one hour. iPad screens were dimmed or brightened to test adaptation to the different light intensities. Visual discrimination optical angle calculations were performed using the parameters of the behavioral shuttle cage (15.24×36 cm), the distance from the decision point (divider), the central position of the LCD panel (18.85 cm), and the parameters of the stimulus pattern (1-6 cm distance between the parallel lines) using the optical (physical) angle equation. Visual angle=$V=2\ \tan^{-1}((D/2)/(L))=18$ degrees=0.33-0.49 radians. Cycles per degree=$1/V$ 0.056 cpd. This is ~9-fold lower than performance in visually intact wt mice (~0.3-0.5 cpd) reported in other studies[39,54,55,56].

For exploratory behavior analysis, two objects were placed in a 50 cm×50 cm open field box. Animals were positioned in the empty box and allowed to explore freely over the course of 10 minutes. The following day, two novel objects were placed in the box and animals were again positioned along the wall of the box and allowed to explore freely for 10 minutes while the arena was filmed continuously. Using Noldus Technology Ethosvision XT v13.5, videos were analyzed for the latency to arrive at and explore each object, the velocity of travel (cm/s) and distance travelled (cm).

Results

Characterization of MW-Opsin in HEK293 Cells

Recent studies have established that vertebrate rhodopsin, found in rod outer segments, may be used ectopically to control Gi/o signaling in cultured cells, under low light intensities 25, but runs down with repeated stimulation and has slow deactivation[24,26]. The slow kinetics are also seen when rhodopsin is expressed in ON-bipolar cells of the blind retina[14,15], raising concern that it may not support vision of natural scenes because of movement of the observer and surrounding objects. The question was asked whether another vertebrate opsin would have the high sensitivity of rhodopsin, but faster kinetics. Melanopsin and extra-retinal opsins have each been measured outside of photoreceptor cells, in a variety of cell types, including in non-photoreceptor cells of the retina, and all found to be as slow or slower than rhodopsin[14-16,27,29]. Opsins from mammalian cone photoreceptor cells were chosen because these deactivate more rapidly in cones than does rhodopsin in rods[30]. Among the cone opsins, MW-opsin, which operates in the center of the visible spectrum, was chosen. Either MW-opsin or rhodopsin was expressed in HEK293T cells with GIRK1 (F137S), a version of the G protein-coupled inward-rectifier potassium channel that forms a homotetramer, which is activated by Gβγ following activation of a Gαi coupled receptor[31] (FIG. 1). In the presence of 9-cis-retinal (a functionally stable analog of the natural chromophore 11-cis-retinal), both MW-opsin and rhodopsin expressing cells displayed large inward photocurrents at negative holding potentials in high external potassium, which were triggered by low intensity (1 mW cm$^{-2}$) flashes of light at 535 nm (for MW-opsin) or 500 nm (for rhodopsin) (FIG. 1 $a,b$). Following illumination, the current elicited by MW-opsin decayed ~8× more rapidly than that elicited by rhodopsin, and recovered more completely, providing reproducible responses over repeated bouts of illumination (FIG. 1$a,c$), as shown earlier in heterologous cells for the short and long wave cone opsins[24]. This suggested that higher speed may be intrinsic to MW-opsin signaling, rather than a specialization of cones. MW-opsin was then tested in non-photoreceptor retinal neurons.

FIGS. 1$a$-1$c$. MW-Opsin and Rhodopsin Activation of GIRK Channels in HEK293 Cells. (a,b)

Representative traces of activation of homotetramer GIRK(F137S) channels by photo-stimulation of rhodopsin (a) or MW-opsin (b) measured in whole cell patch in 50 mM [K$^+$]$_{ext}$ at V$_H$=−80 mV in response to low intensity (1 mW cm$^{-2}$) pulses of light at 535 nm (for MW-opsin) or 500 nm (for rhodopsin). (c) Decay of photo-response (Tau OFF) for Rhodopsin (blue) and MW-opsin (green). Values are mean±SEM; n=6 (Rho), 8 (MW-opsin) cells.

MW-Opsin Restores Fast and Sensitive Light Responses to Blind Retina

Figures 2A, 2B, 2C, 2D, 2E, 2F, 2G:
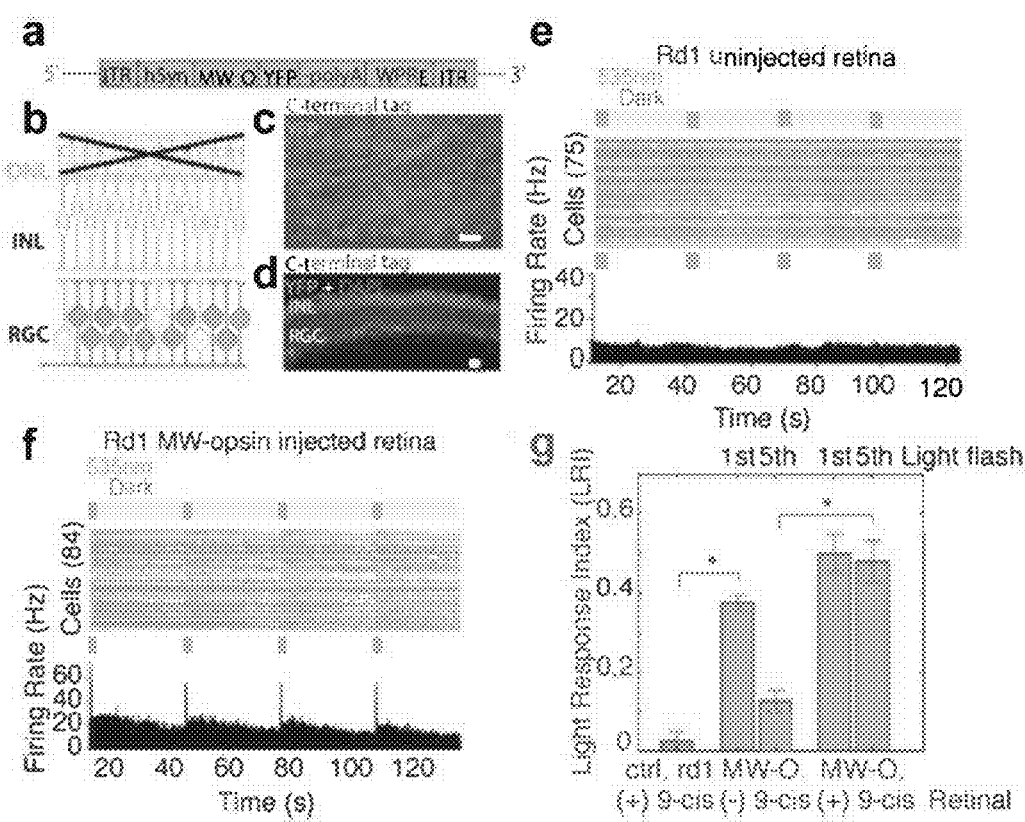
FIG. 2A-2G depict protein expression and light responses in retina isolated from rd1 mice, whose rods and cones have degenerated. Expression of MW-opsin in retinal cells is shown (FIG. 2A-2D), and light-evoked responses that are mediated by MW-opsin are shown (FIG. 2E-2G).

MW-opsin was tested in the retina of the rd1 mouse, which has a mutation in the PDE-6-β gene, resulting in progressive loss of rod and cone photoreceptor cells. MW-opsin under control of the human synapsin promoter (hSyn-1), with a yellow fluorescent (YFP) C-terminal tag for tracking expression, was packaged in AAV2/2(4YF) and injected intravitreally at postnatal day 45 (FIG. 2$a,b$). Retinas were isolated 4-8 weeks weeks later. Expression was found to be pan-retinal with a transfection rate of 45%±19% (SD), restricted to the RGC layer, and localized to the soma and dendrites of both ON- and OFF-RGCs (FIG. 2$c,d$ and 14), a well-defined expression profile consistent with previously shown targeting[32] and similar to expression of rhodopsin under identical parameters (FIG. 15). Retinas were mounted on a multi-electrode array (MEA), with the RGC layer in contact with the electrodes, to test for light-evoked activity. Due to complete photoreceptor degeneration in animals ≥3 months old[33], no light-evoked response was detected in the retina of control rd1 littermates (FIG. 2$e$), with the exception of a few RGCs which displayed slow responses characteristic of intrinsically photosensitive RGCs[57]. In contrast, retinas from animals injected with the MW-opsin encoding AAV displayed robust light-evoked increases in action potential firing, consisting of a large fast, transient component and a small (~30% in size) slow component (FIGS. 2$f, g$, 3$a$, 16, and 17). The light responses ran down with repeated bouts of light stimulation, as expected following removal of the retinal pigment epithelium, a source of 11-cis. The run down was reduced by the addition of 9-cis-retinal (a stable analog of 11-cis retinal) to the recording solution (FIG. 2$g$).

FIGS. 2$a$-2$g$. Expression and Function of MW-Opsin in RGCs of rd1 Mouse Retina. (a)

Viral DNA expression cassette. MW-opsin with YFP (green) under control of hSyn-1 promoter, flanked by inverted terminal repeat (ITR) domains, stabilized by a polyadenylation signal sequence (polyA) and a woodchuck hepatitis posttranscriptional regulatory element (WPRE). (b) Schematic of a degenerated rd1 mouse retina with targeted RGCs highlighted (green). ONL: outer nuclear layer. IPL: inner plexiform layer. Photoreceptor degeneration denoted in light gray. (c,d) En face view of flat mount (c) and transverse slice (d) confocal images of MW-opsin expression of rd1 mouse retina 4 wks after intravitreal injection of AAV2/2-hSyn-MW-opsin-YFP. Images of YFP fused to C terminal end of MW-opsin (green) show pan-retinal distribution (c) in RGC layer in relation to DAPI staining of nuclei (d, blue). Scales 60 μm (c) and 20 μm (d). (e,f) MEA recordings from uninjected control (e) and MW-opsin expressing (f) rd1 mouse retinas. (Top) Raster plot with spikes for each RGC (e: n=75 cells; g: n=84 units). (Bottom) Peristimulus time histogram (PSTH). Light stimulation protocol: 4 pulses of light of 1 s duration (λ=535 nm, green bars) separated by 30 s dark intervals. (g) Normalized Light response Index (LRI) for rd1 retina without (gray) and with MW-opsin expression (green) (gray: N=3 retinas, n=190 cells; green: N=6 retinas, n=273 cells). LRI for 1$^{st}$ and 5th light flash without (light green; N=3 retinas, n=106 cells) and with (dark green; N=3 retinas, n=167 cells) 9-cis retinal. Light intensity 3.38 mW cm$^{-2}$. Wavelength: λ=535 nm (MW-O), Values are mean±SEM. All cells refer to sorted units. Statistical significance assessed using Mann-Whitney U test (*p≤0.001).

Figures 14A, 14B:
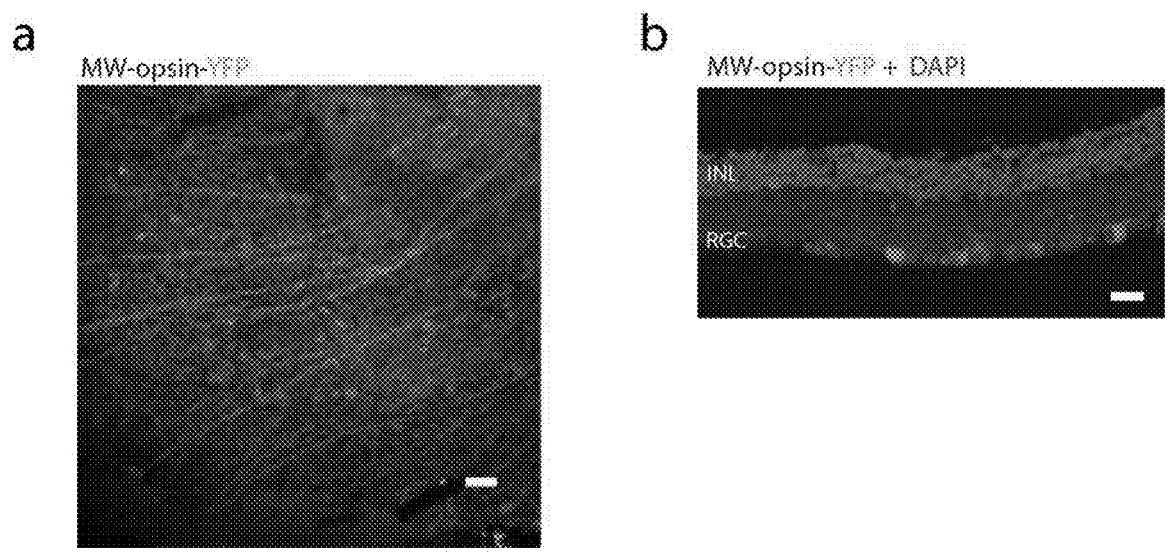
FIG. 14A-14B depict MW-opsin expression in rd1 mouse retina.

FIGS. 14$a$-14$b$. MW-Opsin Expresses in rd1 Mouse Retina.

Flat mount (a) and slice (b) confocal images of MW-opsin-YFP in RGCs of rd1 mouse retina 4-6 wks after intravitreal injection of AAV2/2-hSyn-MW-opsin-YFP. YFP fluorescence (green) and DAPI stain of nuclei (blue). INL=Inner nuclear layer, RGC=Retinal ganglion cell layer. Scale 40 µm (a) and 20 µm (b).

Figures 15A, 15B:
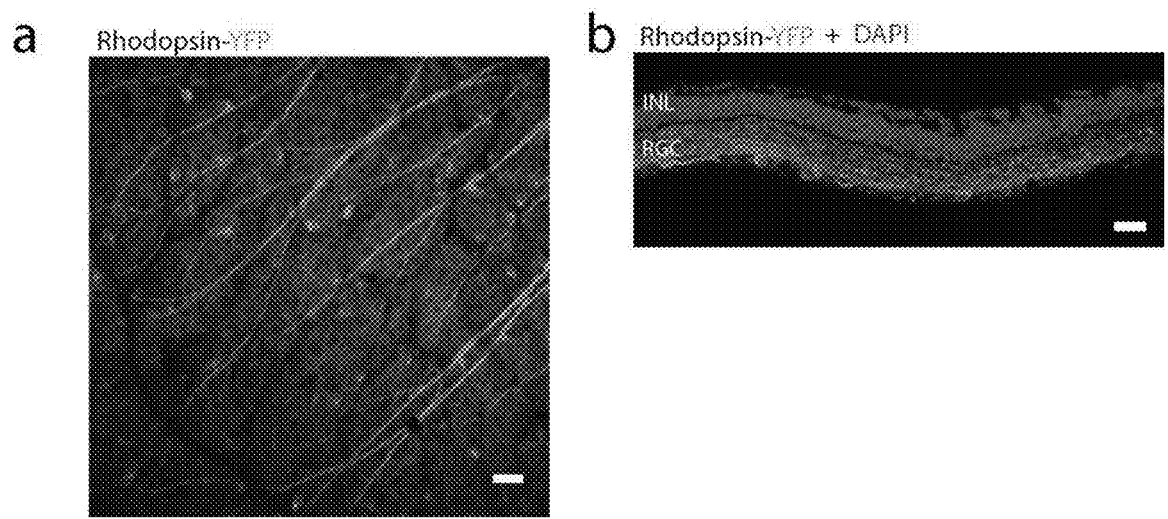
FIG. 15A-15B depict rhodopsin expression in rd1 mouse retina.
Figures 16A, 16B, 16C, 16D:
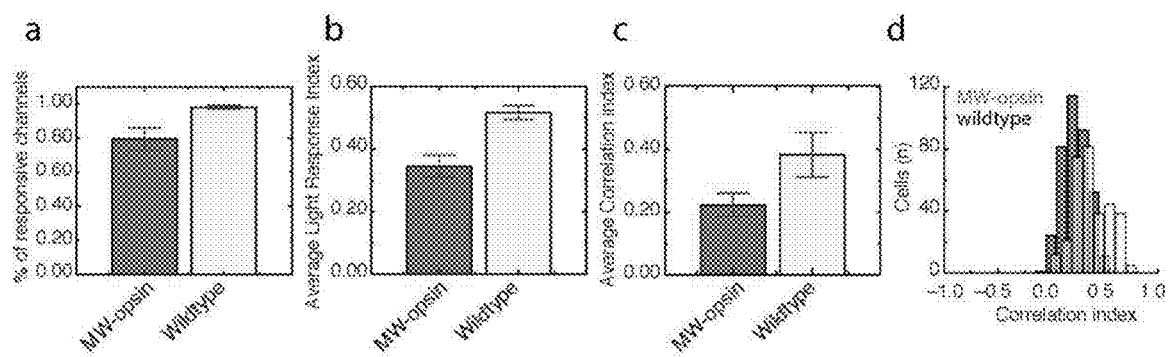
FIG. 16A-16D depict transduction efficiency of MW-opsin in rd1 retina.
Figures 17A, 17B, 17C, 17D:
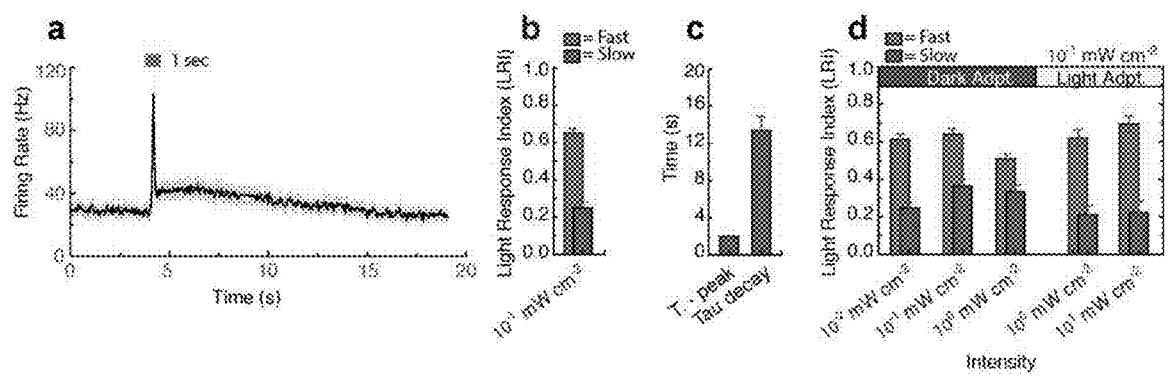
FIG. 17A-17D depict the characterization of slow component of light response in rd1 retina expressing MW-opsin.

FIGS. 15a-15b. Rhodopsin Expresses in rd1 Mouse Retina.

Flat mount (a) and slice (b) confocal images of rhodopsin-YFP in RGCs of rd1 mouse retina 4-6 wks after intravitreal injection of AAV2/2-hSyn-rhodopsin-YFP. YFP fluorescence (green) and DAPI stain of nuclei (blue). INL=Inner nuclear layer, RGC=Retinal ganglion cell layer. Scale 40 µm (a) and 20 µm (b).

FIGS. 16a-16d. Transduction Efficiency of MW-Opsin in rd1 Retina.

(a) Average percent of channels identified in retina of rd1 mouse expressing MW-opsin that display light responsiveness in MEA recordings. Light responsiveness defined as Light Responsive Index (LRI)>0.1, parameters established in Tochitsky et al. (2014)[37], Gaub. et al (2014)[47] and Berry et al. (2017)[62]. (LRI=peak firing rate in light—average firing rate in dark/peak firing rate in light+average firing rate in dark). (b) Average normalized response across retinas). (a,b) N=8 rd1 retinas, N=5 wt retinas. (c) Average cross-correlation values in MW-opsin rd1 (n=370 cells, N=3 retinas) and in wildtype (n=237 cells, N=3 retinas). Cross-correlation of all light-sensitive units in a period 1 s before to 2 s after the light pulse. (d) Correlative value distributions for light sensitive units within the same retina for MW-opsin (n=370 cells, N=3 retinas) and wt retina (n=237 cells, N=3 retinas).

FIGS. 17a-17d. Characterization of Slow Component of Light Response in rd1 Retina Expressing MW-Opsin. (a)

Representative trace of average RGC population response for rd1 expressing MW-opsin ($\lambda$=510 nm; pulse duration 1 sec; 5 flashes averaged at 30 sec interval) shows fast transient component and slow component of the light response (SEM in gray). (b) Comparison of LRI of fast transient (green) and slow (steel-gray) components of light response and their ratio (black) fast/slow) (n=122 channels, N=3 retinas). (c) Kinetics of slow component: time to peak (T.—peak) and time-constant of decay (tau decay). (d) LRI of fast (green) and slow (steel-gray) components under dark (left) and light (right) adapted conditions.

Figures 3A, 3B, 3C, 3D, 3E, 3F, 3G:
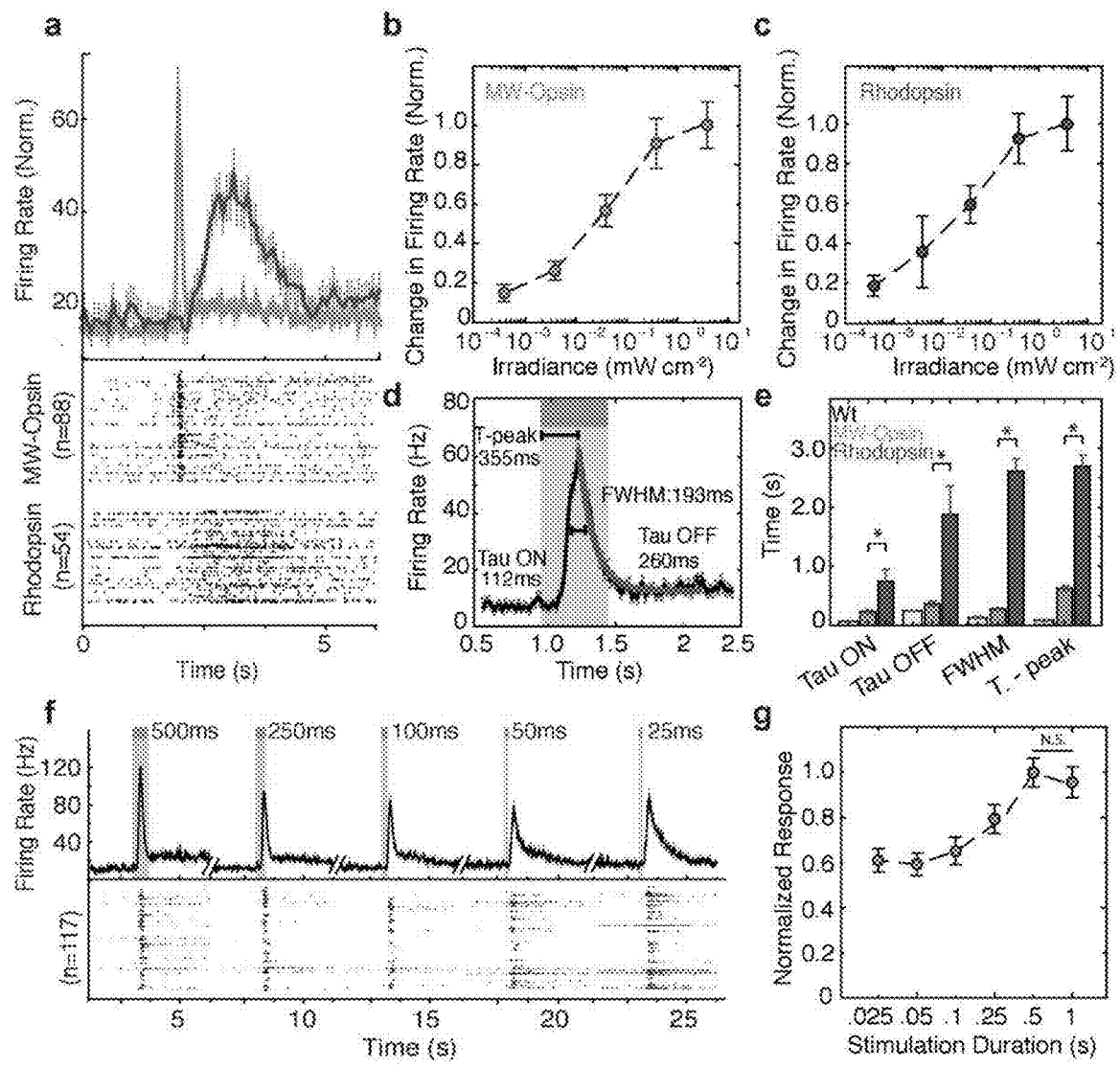
FIG. 3A-3G depict light response timing, size and high sensitivity of MW-opsin or rhodopsin in cells of retinas isolated from blind rd1 mice.
Figures 8A, 8B, 8C, 8D, 8E:
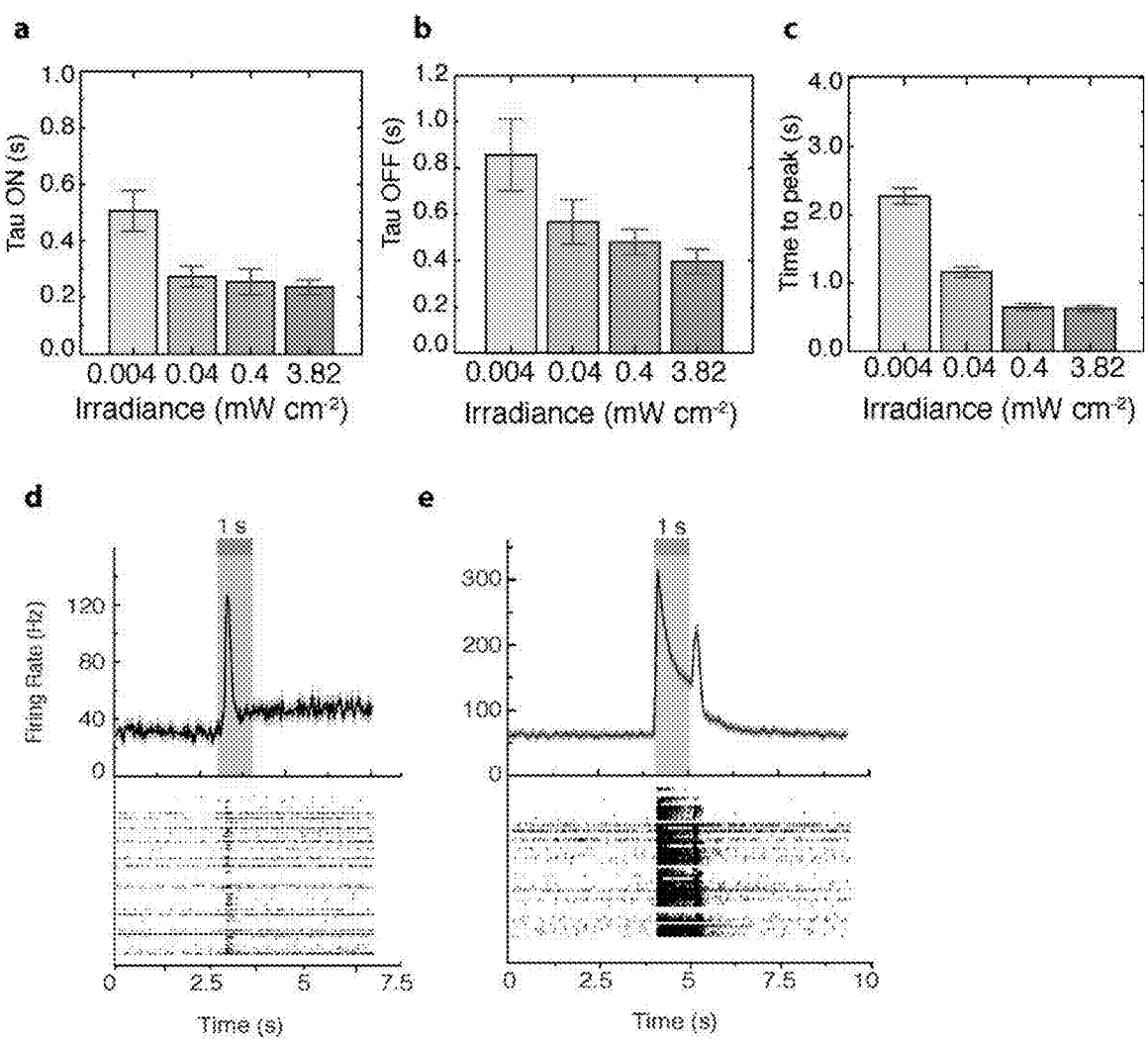
FIG. 8A-8E depict intensity dependent kinetic responses mediated by MW-opsin.

One potential advantage of retinal opsins is their high sensitivity to light in their normal cellular environments. Rhodopsin and melanopsin remain very sensitive when expressed ectopically[25], including in the retina as shown for rhodopsin in ON-BCs and RGCs and melanopsin in RGCs[14-17]. Consistent with this, MW-opsin in RGCs in the rd1 mouse retina was highly sensitive to light, to a degree that is indistinguishable from rhodopsin (FIG. 3b,c). This sensitivity is approximately 1000-fold higher than that of channelrhodopsin[8,13] or halorhodopsin[11,12] and within the range of normal indoor light intensities. FIG. 7. While similar in sensitivity to rhodopsin, MW-opsin had showed kinetics: ~3.5-fold faster rise and ~4-fold shorter time to peak at the start of the light pulse, and ~7-fold faster decay after the end of the light pulse (FIG. 3d,e), resulting in an impulse response that was 270±21 ms in duration at half amplitude, ~10-fold shorter than the 2.61±0.21 s duration at half-amplitude of the rhodopsin impulse response. Tau ON, time to peak, and tau OFF changed modestly with decreasing light intensities, maintaining the advantage in speed over rhodopsin (FIG. 8a-c)[14,15]. The rise and decay kinetics of the response in RGCs of rd1 retina expressing MW-opsin resembled those of the RGC transient ON-response seen in wt retina, except that the former had a longer latency (FIGS. 3e & 8d,e). The fast response kinetics and sensitivity of MW-opsin suggested that it would respond to brief flashes of light. Indeed, illumination pulses as short as 25 ms still triggered responses that reached ~60% of the maximal peak response (FIG. 3f,g), similar to what is seen in wt retina[34].

Figures 18A, 18B, 18C:
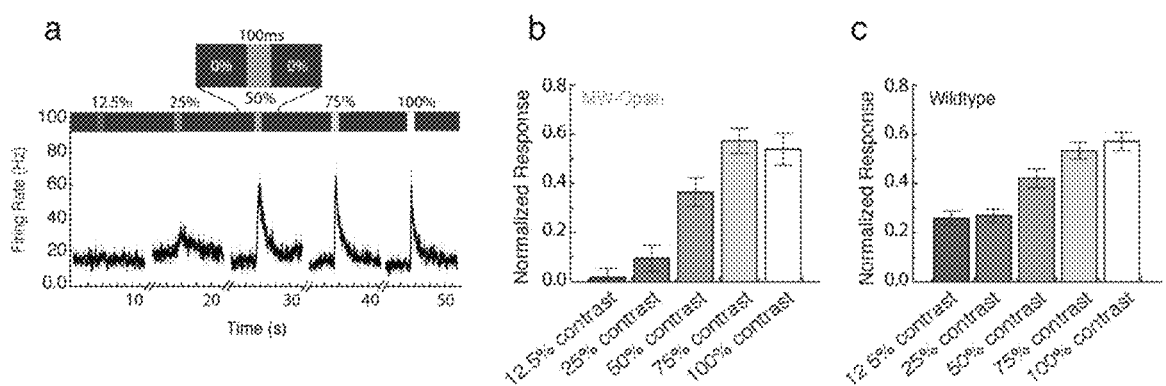
FIG. 18A-18C depict contrast detection in an isolated retina of an MW-opsin expressing rd1 mouse.

Contrast sensitivity in the excised retina and in primary visual cortex was examined in vivo by measuring responses to full-field gray scale steps. In the excised rd1 retina expressing MW-opsin, RGC activity changed in response to changes in brightness of as little as 25% (FIG. 18a,b), approaching but not equivalent to the contrast sensitivity of the wild type retina (FIG. 18c). In complementary in vivo experiments on rd1 animals expressing MW-opsin in RGCs, the experiments involved measuring single unit responses and visually evoked potentials across the layers of primary visual cortex in awake, free running animals (FIG. 19) and observing similar contrast sensitivity using a standard computer monitor (FIG. 20). The cortical responses followed flash frequencies up to at least 4 Hz (FIG. 21). The sensitivity and kinetics of the light responses imparted by MW-opsin in RGCs suggested that it may support visually-guided behavior.

FIGS. 3a-3g. Light Response in Isolated rd1 Mouse Retina with MW-Opsin in RGCs. (a)

(Top) Average response to 1 sec light flash of RGC population expressing MW-opsin (green) or rhodopsin (blue) in RGCs of rd1 mouse retina. (Bottom) Raster plot of average response of rd1 mouse retina RGCs to 5 flashes of 1 s duration light at 535 nm for MW-opsin (n=88 cells) and 510 nm for rhodopsin (n=54 cells) expressing in RGCs. (b,c) Light sensitivity for MW-opsin (N=2 retinas, n=127 cells) and Rhodopsin (N=2 retinas, n=95 cells) in RGCs of rd1 mouse retina. Peak firing rate normalized to maximum at highest intensity. (d,e) Time-course of light response. Population average traces with time from light onset to max excitation (time to peak: 355±21 ms), exponential fits for excitatory phase (Tau ON: 112±25 ms) and decay (Tau OFF: 260±31 ms) and full width at half max (FWHM: 183±85 ms) (e) for MW-opsin (d; e, green; N=3 retinas, n=95 cells) and rhodopsin (e, blue; N=2 retinas, n=67 cells). (f,g) Dependence of MW-opsin light response on flash duration. (f) Representative retina light response (n=117 cells): population average firing rate (top) and raster plot of unit responses (bottom). (h) Normalized peak responses for different stimulation durations (N=2 retina, n=183 cells). Light intensity $3.82 \times 10^{-1}$ mW cm$^{-2}$ unless specified, Wavelength: $\lambda$=535 nm (MW-opsin) or 510 nm (rhodopsin). N=# of retina, n=# of cells/units. All cells refer to sorted units. Values are mean±SEM. Statistical significance assessed using Mann-Whitney U test (*p≤0.001).

FIG. 7. Threshold response of optogenetic systems in blind retinas compared to normal vision. Comparison of threshold sensitivity of natural vision (top) to that of various optogenetic systems introduced to a defined set of surviving neurons in a retina following degeneration of photoreceptor cells (bottom). Mammalian MW-opsin (green), rhodopsin (blue) and melanopsin (cyan) are ~1000× more sensitive than microbial Channelrhodopsin2 and Halorodopsin. Threshold for alternative optogenetic approaches from Bi et al. (2006)[8], Zhang et al (2009)[12], Sengupta et al. (2016)[13], Doroudchi et al. (2011)[45], Gaub et al. (2014)[47], Cronin et al (2014)[65], Berry et al. (2017)[66] De Silva et al. (2017)[17]. (8) Bi et al. (2006) Channelrhodopsin expressed with AAV2-CAG promoter stimulated at 460 nm in rd1 mouse with sensitivity limit in RGCs=$2.2 \times 10^{15}$ photons cm$^{-2}$ s$^{-1}$~1 mW cm$^{-2}$. (12) Zhang et al (2009) Halorhodopsin expressed with AAV2-CMV promoter stimulated at 555-575 nm band pass in rd1 mouse with a sensitivity limit in RGCs=$5.8 \times 10^{16}$ photons $cm^{-2}$ $s^{-1}$~20 mW $cm^{-2}$. (13) Sengupta et al. (2016) Red-shifted channelrhodopsin expressed with AAV2-hSyn promoter stimulated at 595 nm in rd1 mouse with a sensitivity limit in RGCs=$2.5\times10^{15}$ photons $cm^{-2}$ $s^{-1}$~1 mW $cm^{-2}$. (45) Doroudchi et al. (2011) Channelrhodopsin expressed with AAV8-Y733F & SV-40 promoter stimulated at 450-490 nm band pass in rd10 mouse with a sensitivity limit in ON-BCs=$4\times10^{16}$ photons $cm^{-2}$ $s^{-1}$~17 mW $cm^{-2}$. (47) Gaub et al. (2014) LiGluR-$MAG_{460}$ expressed with AAV2-hSyn and AAV2-4×Grm6 promoter stimulated at 445/20 nm in rd1 mouse with a sensitivity limit in RGCs & ON-BCs=$7.1\times10^{14}$ photons $cm^{-2}$ $s^{-1}$~0.3 mW $cm^{-2}$. (65) Cronin et al (2014) Channelrhodopsin expressed with AAV2/8BP2 & 4×GRM6 promoter stimulated in rd1 mouse with a sensitivity limit in ON-BCs=$1\times10^{16}$ photons $cm^{-2}$ $s^{-1}$~5 mW $cm^{-2}$. (66) Berry et al. (2017) SNAG-MGluR2 expressed with AAV2-hSyn promoter stimulated at 445/50 nm in rd1 mouse with a sensitivity limit in RGCs=$1\times10^{14}$ photons $cm^{-2}$ $s^{-1}$~0.5 mW $cm^{-2}$. (17) De Silva et al. (2017) expressed with AAV2/8(Y733F) & CMV enhancer/CBA promoter stimulated at 480/20 nm in rd1 mouse with a Melanopsin sensitivity limit in RGCs=$1.20\times10^{12}$ photons $cm^{-2}$ $s^{-1}$~0.5 µW $cm^{-2}$.

FIGS. 8a-8e. Intensity-Dependent Kinetics of MW-Opsin Light Response. (a-c)

Dependence of light intensity (in seconds) of Tau ON (a), Tau OFF (b), and Time to peak (T-peak) (c) in rd1 retina expressing MW-opsin n=111 cells, N=3 retina. All cells refer to sorted units. Values are mean, error bars are SEM. Wavelength: λ=535 nm. (d,e) Average response of RGC population with SEM in gray (top) and averaged raster plot over 5 light flashes of 1 sec duration (bottom) for rd1 expressing MW-opsin (d; λ=510 nm; n=117 cells) and wt (e, white light; n=50 cells).

FIGS. 18a-18c. Contrast Detection in Isolated Retina of MW-Opsin Expressing rd1 Mouse.

MEA recording of responses to steps from dark to full-field gray scale of different intensities in example isolated retina from MW-opsin expressing rd1 mouse (average of 14 channels) (a). (b,c) Normalized change in RGC firing rate in response to changes in contrast for rd1 mice expressing MW-opsin (N=2 retinas) (b) and wt mice (N=2 retinas) (c). 100% light=25 µW $cm^{-2}$.

FIGS. 19a-19e. In Vivo Light Responses in V1 of rd1 Mouse Expressing MW-Opsin. (a)

Schematic of head-fixed mouse on a running wheel. Stimuli displayed on a standard computer monitor positioned within the visual field of one eye. (b) Responses to 500 ms light pulse. Top, representative visually evoked potential from layer 4 of V1 (average of 20 responses, shaded area represents mean±SEM). Bottom, heat map of responses of individual units from all 16 electrodes of the linear electrode array across the depth of the visual cortex (average of 20 responses). (c) Scatter plot of light-evoked versus baseline firing rate for 39 units across 3 rd1 mice expressing MW-opsin. (d) PSTH (binned at 50 ms) of a representative unit in response to a light flash. (e) Plot of percent change of neuronal firing following stimulation in 39 units across 3 mice.

FIGS. 20a-20d. Contrast Detection In Vivo in MW-Opsin Expressing rd1 Mouse.

(a) Illustration of visual cortex recordings in awake free running rd1 mouse expressing MW-opsin. Randomized contrast changes presented on a computer monitor placed within the animals' visual field. (b) Average firing rate in response to full field contrast steps (500 ms duration) recorded in layer 4 of V1. Inset shows PSTHs binned at 20 ms. 100% light=115 µW $cm^{-2}$.

Figures 21A, 21B, 21C:
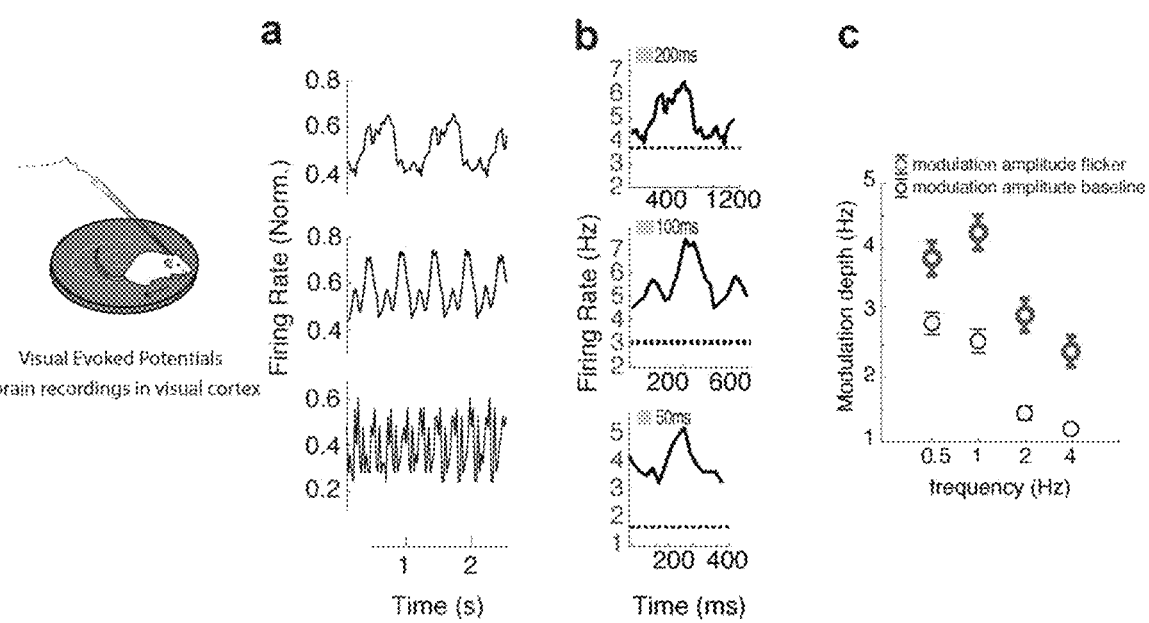
FIG. 21A-21C depict temporal properties of in vivo V1 responses in rd1 mice expressing MW-opsin.

FIGS. 21a-21c. Temporal Properties of In Vivo V1 Responses in rd1 Mice Expressing MW-Opsin. (a-c)

Changes in neuronal firing in the visual cortex induced by full field flickering stimuli of 1, 2 and 4 Hz across 100 cycles.

MW-Opsin Restores Innate Light Avoidance

Figures 4A, 4B, 4C, 4D, 4E, 4F, 4G, 4H, 4I:
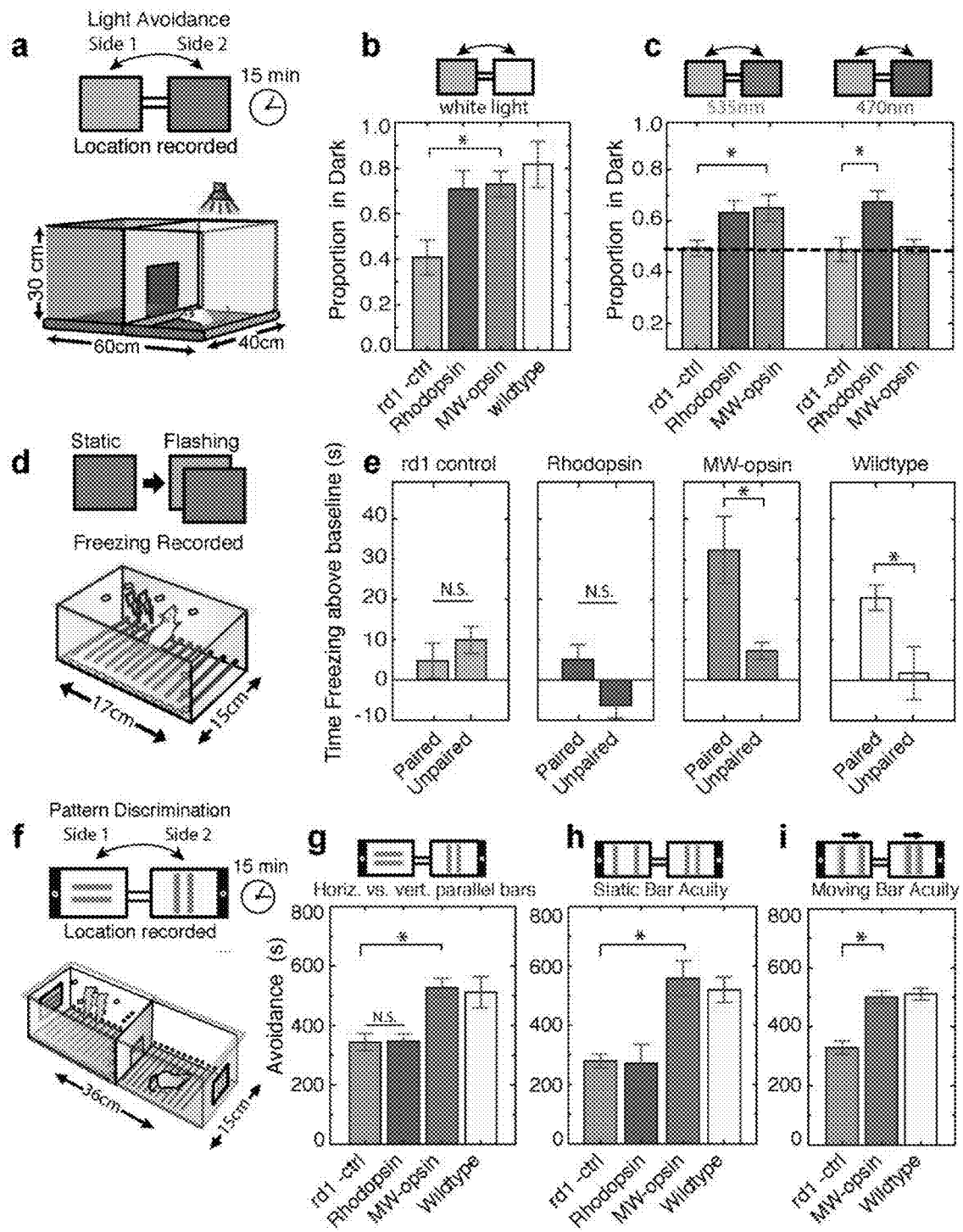
FIG. 4A-4I depict behavioral tests demonstrating equal ability to distinguish light from dark mediated by MW-opsin and rhodopsin in retinal cells of rd1 mice (FIG. 4A-4C), but that only MW-opsin enables animals to distinguish between flashing and constant light (FIG. 4D-4E) or between different spatial light patterns (FIG. 4F-4G). MW-opsin also supports wt-level line differentiation between parallel lines at different spacing that are displayed as still images or in motion (FIG. 4H-4I).
Figures 9A, 9B, 9C, 9D, 9E, 9F, 9G:
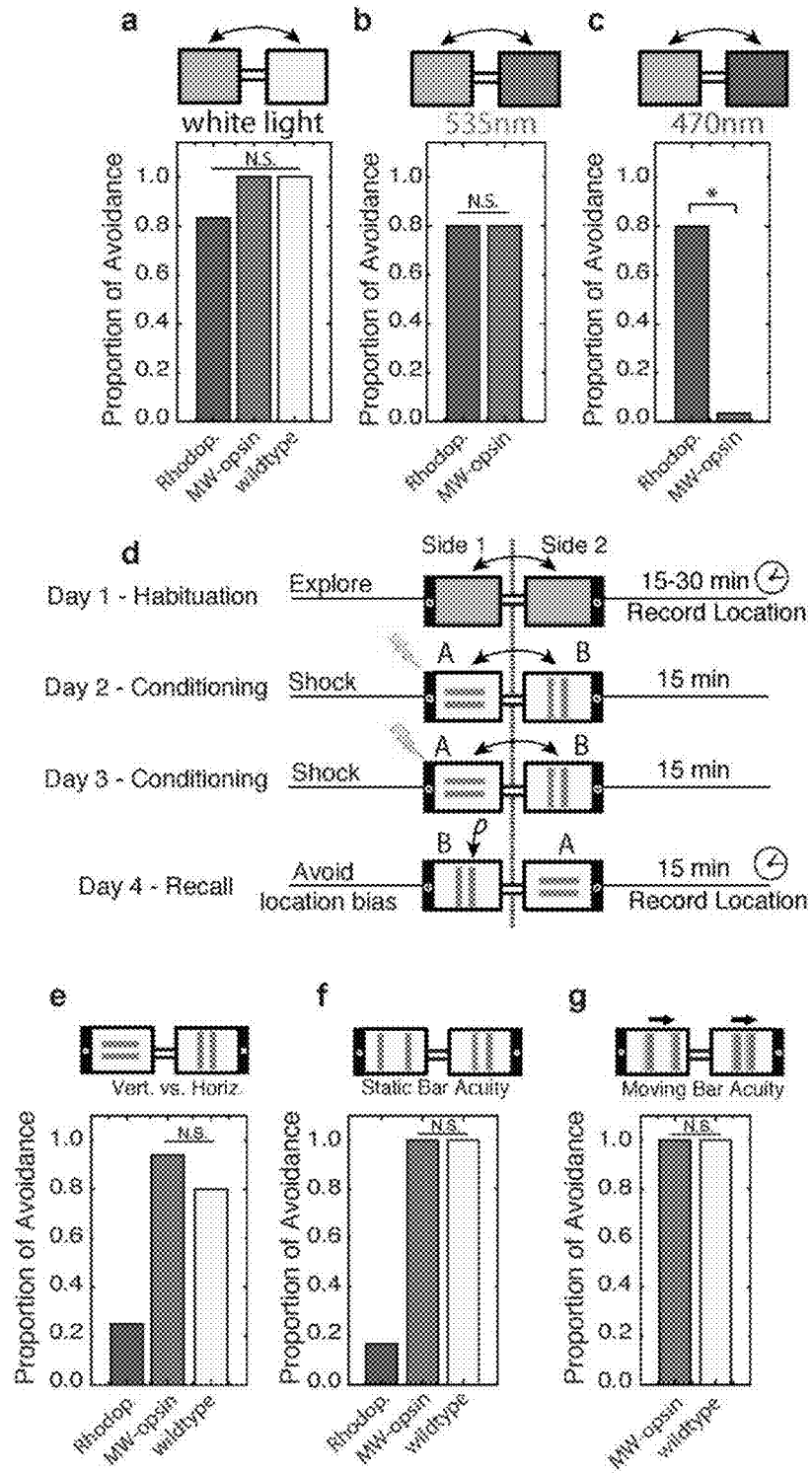
FIG. 9A-9G depict light avoidance and learned pattern discrimination behavior.

Having observed that MW-opsin produces large light responses at low intensities in the isolated rd1 retina, the intact animal was used to assess the ability of MW-opsin to support visual behavior. Sighted mice innately avoid illuminated areas, a survival mechanism associated with evading capture[35]. This behavior is lost following photoreceptor degeneration in the rd1 mouse model[9,16]. To determine if this behavior could be restored, rd1 mice with MW-opsin in RGCs were tested in a behavior box consisting of adjoining light and dark compartments (FIG. 4a). The fraction of time spent in each compartment was recorded and compared to rd1 mice that were not treated and to wt mice (FIG. 4, FIG. 9a-c, FIG. 11), as was the proportion of successful avoidance for each cohort (FIG. 9a-c; and FIG. 11, Table 1). The light compartment was illuminated with low intensity white light, equivalent to indoor office lighting (100 µW $cm^{-2}$). While untreated rd1 animals cannot distinguish by sight between the compartments, they spent about 40-50% of the time in the dark compartment, consistent with an established bias in favor of the light compartment due to familiarity with release location (see Methods) (FIG. 4b). In contrast, rd1 mice expressing either rhodopsin or MW-opsin showed a strong preference for the dark compartment, similar to normally sighted wt animals (FIG. 4b & FIG. 9a). Next, using the same behavioral paradigm, the white light was replaced with blue (460±22 nm) or green (534±25 nm) light and the intensity that was reduced to the lower end of the isolated retina intensity-response curves for MW-opsin and rhodopsin (1 µW $cm^{-2}$; FIG. 3b). Under green light both MW-opsin and rhodopsin expressing animals showed light avoidance (FIG. 4c, left & FIG. 9b), however, under blue light, only rhodopsin animals showed light-avoidance (FIG. 4c, right & FIG. 9c). This display of monochromatic sensitivity is consistent with the action spectrum of MW-opsin[36].

FIGS. 9a-9g. Light Avoidance and Learned Pattern Discrimination Behaviors. (a-c)

Proportion of successful avoidance of the light compartment (proportion of successful avoidance trials) for rd1 expressing rhodopsin in RGCs (blue; n=6 mice) or MW-opsin (green; n=5), and wt mice (white; n=5 mice) when illuminated with either (a) white light (100 µW $cm^{-2}$), (b) 25 µW $cm^{-2}$ green light (535 nm) or (c) 25 µW $cm^{-2}$ blue light (470 nm). Statistical significance assessed using Two-Sided Pearson's Chi-Square Test and One-Sided Fisher's Exact Test when applicable (FIG. 11). Success defined as avoidance greater than mean±S.D. of rd1 untreated control mice (See Methods). (d) Schematic of pattern discrimination experiment. Mice habituated at day 1, exposed to electric shock in association with specific pattern of light (stimulus A/B) paired randomly in either chamber on days 2 and 3 and tested (time spent in each chamber) on day 4, in absence of shock with light patterns reversed to avoid location bias. (e-g) Proportion of successful discrimination of the pattern paired with shock (proportion of successful avoidance trials) compared to rd1 untreated controls. (e) Horizontal vs. vertical parallel bars. Discrimination of parallel static (f) or moving (g) bars at distances of 1 vs. 6 cm. Respectively for e,f and g: rd1 rhodopsin (blue; n=8(e), 6(f) mice), rd1 MW-opsin (n=17(e), 11(f), 6(g) mice) and wt (n=5(e), 6(f), 9(g) mice). (25 µW cm$^{-2}$). Statistical significance assessed using Two-Sided Pearson's Chi-Square Test and One-Sided Fisher's Exact Test when applicable (FIG. 11). Success defined as avoidance greater than mean±S.D. of rd1 untreated control mice.

MW-Opsin Supports Detection of Temporal Light Patterns

Having observed that MW-opsin triggers faster light responses than does rhodopsin in the isolated rd1 retina, it was asked whether this would translate into a superior ability to discriminate between different temporal patterns of light. A visually cued fear-conditioning paradigm was used to test the ability of animals to differentiate flashing from constant light. Wt mice, or rd1 mice expressing either MW-opsin or rhodopsin in RGCs, were placed in a behavioral apparatus consisting of a single compartment in which a low intensity (100 µW cm$^{-2}$) LCD screen switched between constant light and flashing light (2 Hz). In each animal, either constant light or flashing light was consistently paired with a mild foot shock. This was done for 1 trial per day for 2 days (FIG. 4d) and animals were tested on day 3 with light cues presented in the absence of foot shock, with freezing time used to measure fear association, as done earlier[15,27,37]. Freezing time was measured over a period of 10 seconds following the switch of temporal light pattern. The measurements from animals in which the visual cue and shock were paired (paired group) were compared to measurements from a cohort of animals in which the training shocks were randomized (i.e. not paired consistently with one of the stimuli) (unpaired group). Freezing times in untreated rd1 mice did not differ between paired and unpaired conditions, consistent with the expected inability of the animals to see the visual cues (FIG. 4e, gray). In contrast, rd1 mice expressing MW-opsin in RGCs showed more freezing in the paired condition, as observed in wt animals (FIG. 4e, green and white). Strikingly, rd1 mice expressing rhodopsin in RGCs did not differ between paired and unpaired conditions (FIG. 4e, blue). This suggests that, unlike blind mice expressing MW-cone opsin, rhodopsin mice cannot discriminate light flashing at 2-Hz from constant light, consistent with the slow light response kinetics observed in MEA (FIG. 3e).

MW-Opsin Restores Spatial Pattern Discrimination

It was next determined if MW-opsin in RGCs would enable rd1 mice to detect spatial patterns of light. A behavioral chamber with two adjoining compartments (FIG. 4f), each with a low intensity LCD tablet (iPad) mounted on a wall, was used. Each tablet displayed a pair of parallel lines. In one case, the lines were oriented vertically (II) and in the other horizontally (=). For MW-opsin the wavelength was centered at 535 nm (520-560) and for rhodopsin at 497 nm (480-520) (FIG. 9d). Initially, mice were given time to habituate to the compartments with the visual displays turned off (day 1). During a 2-day training period, an aversive foot shock was paired with either the vertically or horizontally oriented lines. The aversive cue was assigned randomly and maintained consistently for that animal. On day 4 the locations of the stimuli were switched to avoid location bias and conditioned avoidance was tested (FIG. 9d). It was found that rd1 animals with MW-opsin in RGCs showed avoidance of the aversive visual cue that was significantly greater than that seen in untreated rd1 control animals, and similar to that seen in wt mice (FIG. 4g and FIG. 9e). In contrast, rd1 animals with rhodopsin in RGCs did not differ from the untreated rd1 control animals and displayed a slight preference for the adverse stimulus, a clear example of location bias seen in blind animals. These observations indicate that MW-opsin restores the ability to recognize spatial light patterns, but that rhodopsin does not.

Having observed that MW-opsin supports spatial pattern recognition, the question was asked if mice could discriminate differences between lines of identical orientation but different spacing, a visual task adopted from tests of visual acuity in humans and animals[38,39]. Parallel vertical lines were separated by distances of either 1 or 6 cm. As above, an aversive foot shock was randomly paired with one of the stimuli during the training period on days 2 and 3, and recall was tested on day 4 as a measure of avoidance. It was found that rd1 mice expressing MW-opsin are able to distinguish between the two patterns with a performance preference for the non-aversive stimuli that was similar to that seen in wt mice, whereas rhodopsin expressing animals are similar to untreated rd1 mice (FIG. 4h, FIG. 9f, and FIG. 22). MW-opsin also supported line differentiation when the parallel lines were in motion (1 cm/sec) (FIGS. 4i and 9g).

The question was asked if the "refresh" rate of MW-opsin is fast enough to support recognition of line pattern when the pattern is in motion. To test this, the same close line differentiation task was performed, but now with the parallel lines moving at 5 cm per sec. It was found that rd1 mice expressing MW-opsin displayed a preference for the moving pattern that was paired with the non-aversive stimulus, and performed as well as did wt mice (FIG. 4i & FIG. 9g). These results indicate that MW-opsin in RGCs supports recognition of both static and moving spatial patterns at the low indoor light intensity of an LCD screen.

FIGS. 4a-4i. Light Avoidance and Learned Visually-Guided Behavior in rd1 Mice Expressing MW-Opsin or Rhodopsin in RGCs. (a) Schematic of light/dark box for light avoidance test. (b, c) Proportion of time spent in the dark compartment (proportion of avoidance) for rd1 control (gray; n=4 mice), rd1 expressing rhodopsin in RGCs (blue; n=6 mice) or MW-opsin (green; n=5), and wt mice (white; n=5 mice) when illuminated with either (b) white light (100 µW cm$^{-2}$), (c) 25 µW cm$^{-2}$ blue light (470 nm) (right) or green light (535 nm) (left). (d) Schematic of freezing response fear conditioning experiment. (e) Quantification of fear response for discrimination of temporally patterned stimulation. Time freezing above baseline is shown for when illumination transitions from static to 2 Hz frequency stimulation (100 µW cm$^{-2}$) was paired or unpaired with a electric shock for control rd1, rhodopsin, MW-opsin, and wt mice (n=4, 6, 12, 10 paired, n=7, 8, 7, 12 unpaired). (f) Schematic of pattern discrimination experiment. Mice habituated at day 1, then exposed to electric shock in association with specific pattern of light projected to ipads and paired randomly in either chamber (conditioning days 2 and 3). On day 4 recall tested (time spent in each chamber), in absence of shock with light patterns reversed to avoid location bias (See FIG. 8d). (g-i) Learned pattern discrimination. Time spent avoiding pattern paired with shock. (g) Horizontal vs. vertical parallel bars. (h) Discrimination of parallel static (h) or moving (i) bars at distances of 1 vs. 6 cm. Respectively for g,h and i: rd1 control (n=8, 5, 16 mice), rd1 rhodopsin (blue; n=8 mice), rd1 MW-opsin (n=17, 11, 6 mice) and wt (n=5, 6, 9 mice). (25 µW cm$^{-2}$). (Note, proportion of success for these experiments shown in FIG. 9a-c). Light intensity=25-100 µW cm$^{-2}$; Wavelength: =535 nm (MW-opsin), 510 nm (rhodopsin) or white light (MW-opsin). n=# of mice. Statistical significance assessed using Student's two-tailed t-test with Bonferroni correction: *p<0.01.

Figure 22A:
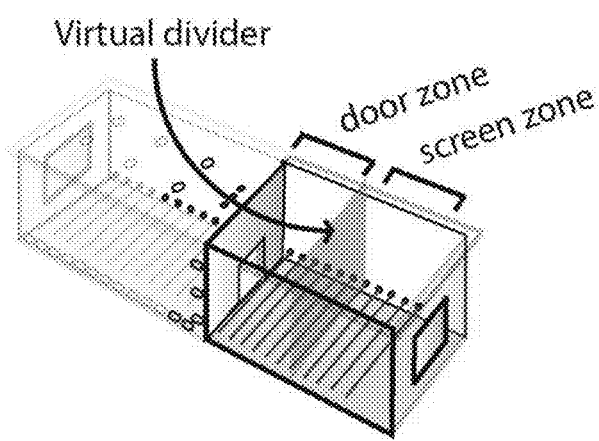
FIG. 22A-22B depict location preference in discrimination tasks.
Figure 22B:
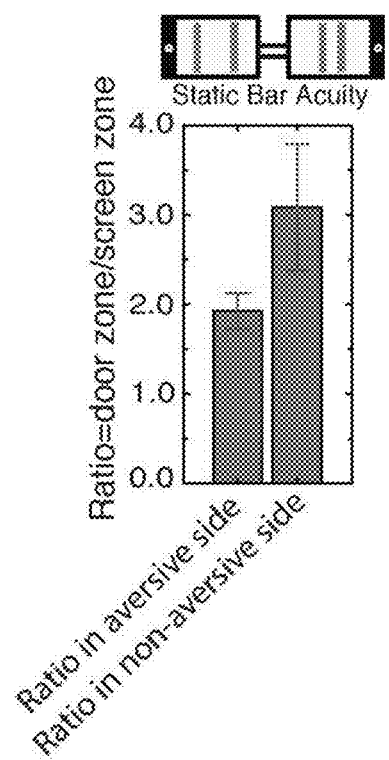

FIGS. 22a-22b. Location Preference in Discrimination Task. (a) Illustration of arena used in discrimination tasks, showing a virtual divider separating each compartment in half in order to determine the proportion of time spent near the central divider between the two chambers versus near the screen. (b) Ratio of time spent in the zone close to central divider versus zone closest to the screen for the aversive and non-aversive sides reveals preference for zone closest to the central divider. Values are mean; error bars are SEM.

MW-Opsin Undergoes Light Adaptation

A fundamental characteristic of vision is the ability to distinguish objects across a wide range of ambient light intensities. This adaptation is mediated by several different mechanisms in photoreceptor cells. The question was asked whether some aspect of adaptation would transfer to RGCs with MW-opsin. Retinas expressing MW-opsin in RGCs were excised, mounted on the MEA and perfused with 9 cis-retinal. The retina was first kept in complete darkness for 15 min (dark-adapted); then, a series of brief (1 s) flashes of green light (535±25 nm) at long intervals (60 sec) and over a range of intensities was tested. The light was then adapted for 10 minutes to a moderate indoor light level (light-adapted; white light at 100 $\mu W$ $cm^{-2}$) and the light pulse series was repeated.

Figures 5A, 5B, 5C, 5D, 5E, 5F:
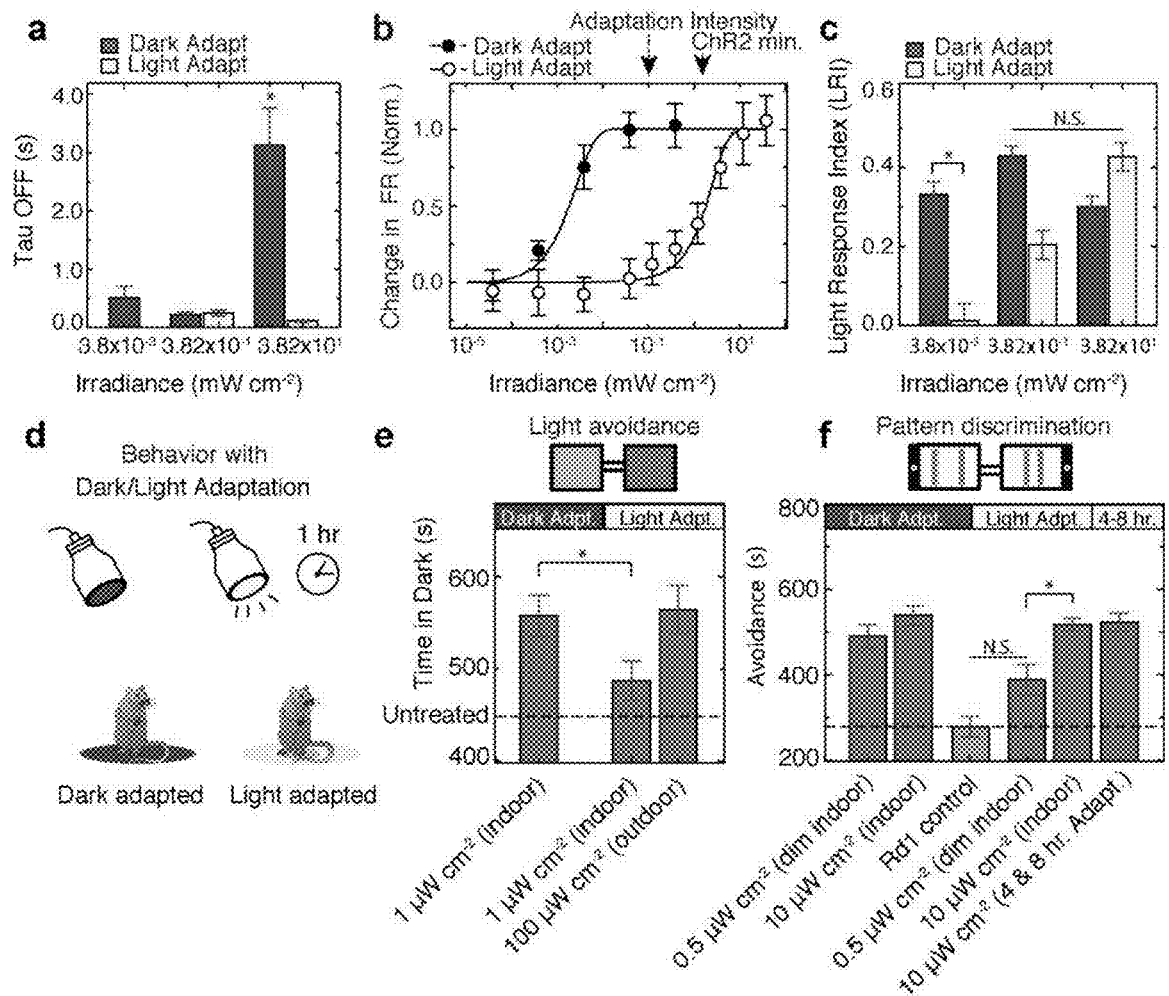
FIG. 5A-5F depict MW-opsin mediated light adaptation in rd1 mice: in MEA recordings on isolated retina (FIG. 5A-5C) and visually-guided behavior (FIG. 5D-5F).
Figures 10A, 10B, 10C, 10D, 10E, 10F, 10G:
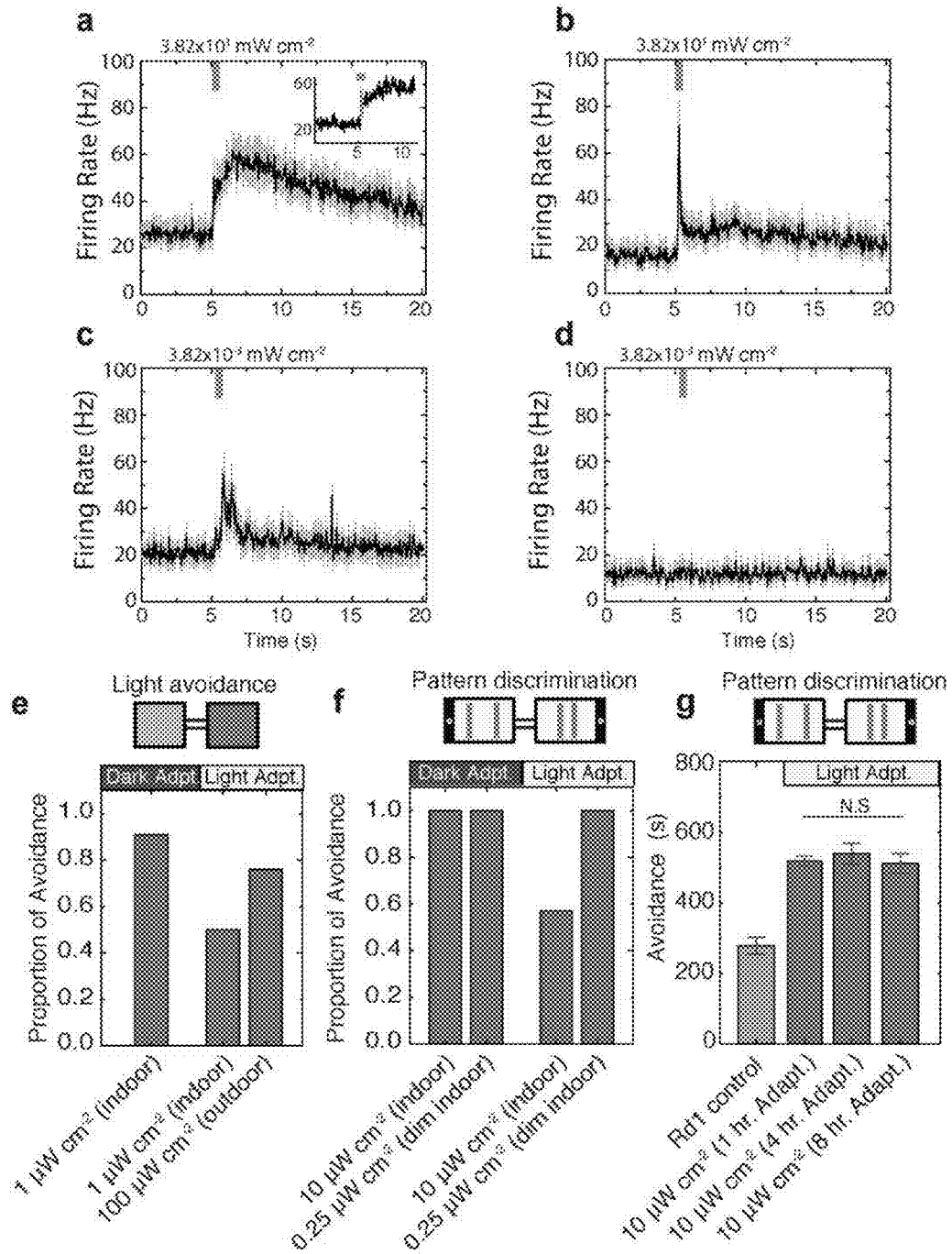
FIG. 10A-10G depict light adaptation of excised retina and behavioral mice.

The kinetics of the light responses was examined. The light response decayed rapidly, as shown above, for both the light and dark-adapted retina, except in one case: the response to a bright flash in the dark-adapted retina decayed ~12× more slowly (3.14±0.63 s, n=171, N=3) than the same retinas under light adapted conditions (FIG. 5a & FIG. 10a,b). Light responses driven by intact photoreceptors show similar behavior and this is believed to play a role in desensitization to subsequent stimulation[40,41] and to underlie the "afterimage" in humans following a bright flash that transiently obscures vision[42]. Because of its unusual properties, this response of the dark-adapted retina to the brightest light flash was excluded from the intensity-response analysis.

The intensity-response curve showed that the dark-adapted retinas had a high light sensitivity, responding at ~0.5 $\mu W$ $cm^{-2}$, whereas the light-adapted retinas were far less sensitive, requiring ~100 $\mu W$ $cm^{-2}$ to respond (FIGS. 5b,c and 10c,d). This adaptation shifted the intensity curve by ~3 orders of magnitude (780±82), N=3) (FIG. 5b,c).—A striking feature of the adaptation was that the maximal light response was similar in the dark-adapted and light-adapted retina (FIG. 5c), as shown earlier in native cone photoreceptors[43,44].

Having observed that the light response mediated by MW-opsin in RGCs undergoes light adaptation in the isolated retina, the question was asked if this would translate into visually useful light adaptation in the behaving animal. The MW-opsin-mediated light response in RGCs was examined in the context of light avoidance behavior. Prior to testing, rd1 mice expressing MW-opsin in RGCs were held for 1 hour either in complete darkness (dark adapted) or under indoor illumination (white light, 1 mW $cm^{-2}$/535 nm light component, 50 $\mu W$ $cm^{-2}$) (FIG. 5d). They were then tested immediately in the two-chamber light-dark box for light avoidance behavior where the light box had green (535 nm) illumination at either 1 $\mu W$ $cm^{-2}$ (indoor light) or 100 $\mu W$ $cm^{-2}$ (outdoor light). The light adapted MW-opsin expressing rd1 mice showed strong light avoidance when the test light was brighter (535 nm, 100 $\mu W$ $cm^{-2}$) than the light level to which they were light-adapted (FIG. 5e). The light avoidance was reduced when the test light was the dimmer (535 nm, 1 $\mu W$ $cm^{-2}$) than light level to which they were light-adapted (FIG. 5e & FIG. 10e). In contrast, the dim test light of 1 $\mu W$ $cm^{-2}$ produced a high level of light avoidance in the dark-adapted animals, indicating behaviorally relevant light adaptation.

The question was asked if the effect of light adaptation on light avoidance behavior would also operate for pattern recognition in a learned visual image discrimination task. As above (FIG. 4), mice were conditioned over a 3-day training period by pairing mild foot shock with one of two displays of parallel lines at differing spacing presented on LCD screens in two adjoining chambers (FIGS. 4h and 9d). Once again, mice were tested with only the visual stimulus on day 4, but this time, immediately before testing, they underwent 1 hour of either dark adaptation (no light) or light adaptation (white light) for 4 or 8 hrs. The intensity of the line patterns during the recall was either 0.25 $\mu W$ $cm^{-2}$ or 10 $\mu W$ $cm^{-2}$ following light adaptation. It was found that rd1 mice expressing MW-opsin in RGCs that had been dark-adapted were able to discriminate between the line patterns and avoid the aversive cue whether it was presented at the low (0.25 $\mu W$ $cm^{-2}$) or moderate (10 $\mu W$ $cm^{-2}$) indoor intensity (FIG. 5f & FIG. 10f). In contrast, light-adapted animals only succeeded with the brighter test line patterns and were identical in performance between the groups that were light adapted for 1, 4, and 8 hours (FIGS. 5f and 10g). The results show that spatial pattern recognition mediated by MW-opsin is adaptive over a range of natural light intensities.

MW-Opsin Restores Novel Object Exploration

Figures 13A, 13B, 13C, 13D, 13E, 13F, 13G, 13H, 13I, 13J, 13K, 13L:
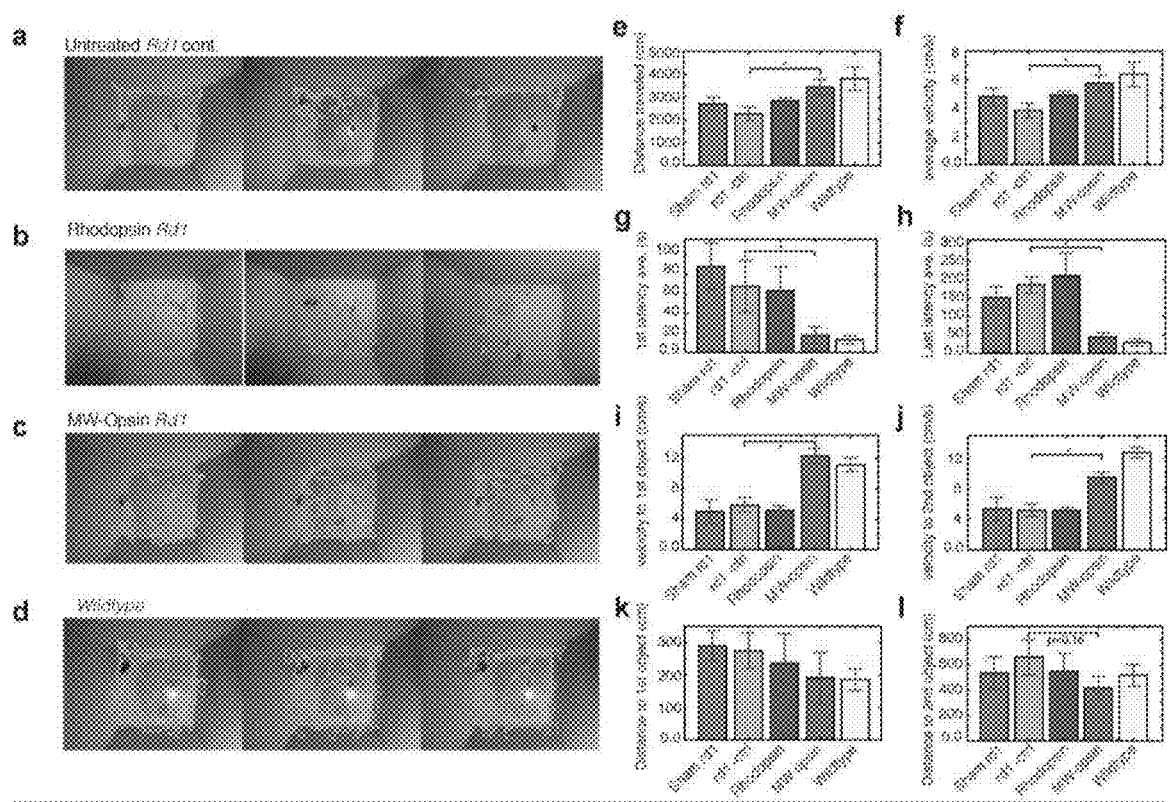
FIG. 13A-13L depict restoration of visually-guided exploratory behavior by MW-opsin.

The experiments above show that MW-opsin enables pattern recognition across a wide range of light intensities using illuminated displays. A question was how it would operate in a natural environment, where ambient, incidental light illuminates three-dimensional objects. To address this, experiments employed an open field arena that is commonly used to test novel object recognition and exploratory behavior[62, 63]. Mice naturally avoid open spaces and maintain proximity to walls of their environment. Exploratory excursions from these places of safety can be motivated by novel stimuli. Although mice employ multiple sensory modalities during exploration, vision has been shown to be critical for spatial navigation[64]. The arena consisted of a cube containing two distinct novel objects. The mouse was placed against the arena wall, far enough from the objects, which themselves were far enough apart, so that the chance of an accidental encounter was low whether the animal walked along the wall or explored the other object. rd1 untreated, rd1-sham injected, rd1 expressing rhodopsin or rd1 expressing MW-opsin mice, as well as wt animals, were filmed. Their movements were tracked for 10 minutes the first time that they were placed into the arena (FIG. 13a-d). It was found that wt animals travel 1.57-fold farther and moved at an average velocity 1.55-fold faster than blind rd1 animals, consistent with the known visual component of exploratory behavior. Strikingly, like wt animals, rd1 animals expressing MW-opsin traveled farther (by 1.39-fold) and faster (by 1.37-fold) than their untreated rd1 littermates (FIG. 13e,f), suggesting that MW-opsin supports normal novel object exploration. To analyze this further, experiments focused on aspects of exploratory behavior that most likely depend on vision at a distance; the latency to exploration of the novel objects and the velocity and distance traveled on the excursions to the objects. Sham injected and rhodopsin expressing rd1 mice performed similarly to untreated rd1 animals, but MW-opsin mice reached the first and second objects in 3.88-fold and 3.62-fold shorter times, respectively (FIG. 13g,h), moved at velocities that were 2.1-fold and 1.83-fold faster to the first and second objects, respectively (FIG. 13i,j), and took shorter pathways that were 0.69-fold and 0.64-fold the distance to the first and second objects, respectively (FIG. 13k,l), as compared to untreated rd1 mice. In each of these measures, MW-opsin expressing rd1 mice reached levels that were similar to those of wt animals (FIG. 13e-g). These results suggest that MW-opsin in RGCs provides previously blind animals with naturalistic vision of objects under ambient light.

FIGS. 5a-5f. Light Adaptation in RGC Activity and Visually-Guided Behavior Mediated by MW-Opsin. (a-c) MEA recordings in isolated retina of RGC light response mediated by MW-opsin in RGCs of rd1 mouse retina show sensitivity difference with retina adapted to dark versus light. (a) Light response decay (Tau OFF) as a function of flash intensity in dark versus light adapted condition (N=3 retinas, n=171 cells). (b) Example intensity-response curve for representative retina first dark adapted (filled symbols) then light adapted (open symbols) (n=57 cells). White light adaptation. ChR2 minimum value from Bi et al. (2006)[8] & Sengupta et al. (2016)[13]. (c) Average (error bars are SEM) normalized Light response Index (LRI) at 3 flash intensities in same retina, first dark adapted and then light adapted (N=3 retinas, n=171 cells). (d-f) Behavior shows light adaptation in visually-guided tasks. (d) Schematic of adaptation to dark or light prior to testing of innate avoidance behavior or learned pattern discrimination behavior. (e) Proportion of time spent in the dark compartment (proportion of avoidance) under outdoor light (100 $\mu W\ cm^{-2}$) or indoor light (1 $\mu W\ cm^{-2}$) following 1 hr. of adaptation to dark (n=11 mice) or adaptation to light (white light; 1 mW $cm^{-2}$/535 nm spectral component; 50 $\mu W\ cm^{-2}$; n=12,13 mice). (f) Learned pattern discrimination of parallel bars spaced at distances of 1 versus 6 cm displayed at low (0.25 $\mu W\ cm^{-2}$) or indoor (10 $\mu W\ cm^{-2}$) light levels following 1 hr. of adaptation to dark (n=8,8 mice) or light (white light; 1 mW $cm^{-2}$/535 nm spectral component; 50 $\mu W\ cm^{-2}$; n=7,7 mice). Dotted line denotes average performance of untreated rd1 control mice. Light intensity $3.82 \times 10^1$ mW $cm^{-2}$, Wavelength: $\lambda$=535 nm. All cells refer to sorted units. Values are mean±SEM. Statistical significance assessed using Mann-Whitney U test (*p≤0.01). Student's two-tailed t-test with Bonferroni correction: *p<0.05.

FIGS. 10a-10g. Light Adaptation in Excised Retina and Mouse Visual Behavior. (a-d) Representative trace of average RGC population response in retina expressing MW-opsin (n=57). Response to 500 ms light flashes of $3.82 \times 10^1$ mW $cm^{-2}$ (a,b) or $3.82 \times 10^{-3}$ mW $cm^{-2}$ (c,d) following adaptation to dark (a,c) or light (b,d). (e) Avoidance of the light compartment (proportion of successful avoidance trials) under indoor light (1 $\mu W\ cm^{-2}$) following 1 hr. of adaptation to dark (n=11 mice) compared with proportion of successful avoidance mice under indoor light (1 $\mu W\ cm^{-2}$; n=12 mice) and outdoor light (100 $\mu W\ cm^{-2}$; n=13 mice) following 1 hr. of adaptation to light (white light; 1 mW $cm^{-2}$/535 nm spectral component; 50 $\mu W\ cm^{-2}$). (f) Proportion of successful discrimination of the parallel bars spaced at distances of 1 versus 6 cm displayed at low (0.25 $\mu W\ cm^{-2}$) or indoor (10 $\mu W\ cm^{-2}$) light levels following 1 hr. of adaptation to dark (n=8 mice at 0.25 $\mu W\ cm^{-2}$, 8 mice at 10 $\mu W\ cm^{-2}$) or light (n=7 mice at 0.25 $\mu W\ cm^{-2}$, 7 mice at 10 $\mu W\ cm^{-2}$). (g) Learned pattern discrimination of parallel bars spaced at distances of 1 versus 6 cm displayed at indoor (10 $\mu W\ cm^{-2}$) light levels following 1, 4 or 8 hrs. of light adaptation (n=7,4,4) compared to unadapted rd1 controls.

FIG. 11 (Table 1). Statistical Significance of Light Avoidance and Learned Visually-Guided Behavior.

Success ratios were calculated for avoidance performance of condition behaviors (FIG. 4,5 & FIG. 9, 10). To determine significance in differences between conditions a pairwise contingency table was then constructed, and a Two-Sided Pearson's Chi-Square Test was initially conducted. To correct for conditions with a small n, a One-Sided Fisher's Exact Test was also conducted.

REFERENCES

1. Tuo, J., Bojanowski, C. M. & Chan, C.-C. Genetic factors of age-related macular degeneration. *Progress in retinal and eye research* 23, 229-249 (2004).
2. Leveillard, T. & Sahel, J. A. Rod-derived cone viability factor for treating blinding diseases: from clinic to redox signaling. *Sci Transl Med* 2, 26ps16 (2010).
3. Bennett, J. Taking Stock of Retinal Gene Therapy: Looking Back and Moving Forward. *Molecular Therapy* 25, 1076-1094.
4. Daiger, S. P., Bowne, S. J. & Sullivan, L. S. Perspective on genes and mutations causing retinitis pigmentosa. *Arch Ophthalmol* 125, 151-158 (2007).
5. Ferrari, S., et al. Retinitis pigmentosa: genes and disease mechanisms. *Curr Genomics* 12, 238-249 (2011).
6. Mazzoni, F., Novelli, E. & Strettoi, E. Retinal ganglion cells survive and maintain normal dendritic morphology in a mouse model of inherited photoreceptor degeneration. *J Neurosci* 28, 14282-14292 (2008).
7. Haverkamp, S., et al. Synaptic plasticity in CNGA3(−/−) mice: cone bipolar cells react on the missing cone input and form ectopic synapses with rods. *J Neurosci* 26, 5248-5255 (2006).
8. Bi, A., et al. Ectopic expression of a microbial-type rhodopsin restores visual responses in mice with photoreceptor degeneration. *Neuron* 50, 23-33 (2006).
9. Busskamp, V., et al. Genetic reactivation of cone photoreceptors restores visual responses in retinitis pigmentosa. *Science* 329, 413-417 (2010).
10. Lagali, P. S., et al. Light-activated channels targeted to ON bipolar cells restore visual function in retinal degeneration. *Nat Neurosci* 11, 667-675 (2008).
11. Thyagarajan, S., et al. Visual function in mice with photoreceptor degeneration and transgenic expression of channelrhodopsin 2 in ganglion cells. *J Neurosci* 30, 8745-8758 (2010).
12. Zhang, Y., Ivanova, E., Bi, A. & Pan, Z. H. Ectopic expression of multiple microbial rhodopsins restores ON and OFF light responses in retinas with photoreceptor degeneration. *J Neurosci* 29, 9186-9196 (2009).
13. Sengupta, A., et al. Red-shifted channelrhodopsin stimulation restores light responses in blind mice, macaque retina, and human retina. *EMBO Molecular Medicine* 8, 1248-1264 (2016).
14. Cehajic-Kapetanovic, J., et al. Restoration of Vision with Ectopic Expression of Human Rod Opsin. *Current biology: CB* 25, 2111-2122 (2015).
15. Gaub, B. M., Berry, M. H., Holt, A. E., Isacoff, E. Y. & Flannery, J. G. Optogenetic Vision Restoration Using Rhodopsin for Enhanced Sensitivity. *Mol Ther* 23, 1562-1571 (2015).
16. Lin, B., Koizumi, A., Tanaka, N., Panda, S. & Masland, R. H. Restoration of visual function in retinal degeneration mice by ectopic expression of melanopsin. *Proceedings of the National Academy of Sciences of the United States of America* 105, 16009-16014 (2008).

17. De Silva, S. R., et al. Long-term restoration of visual function in end-stage retinal degeneration using subretinal human melanopsin gene therapy. *Proc Natl Acad Sci USA* (2017).
18. Cepko, C. Neuroscience. Seeing the light of day. *Science* 329, 403-404 (2010).
19. Klapper, S. D., Swiersy, A., Bamberg, E. & Busskamp, V. Biophysical Properties of Optogenetic Tools and Their Application for Vision Restoration Approaches. *Front Syst Neurosci* 10, 74 (2016).
20. The Lasker, I.I.f.I.i.V.S. Restoring Vision to the Blind: The Lasker/IRRF Initiative for Innovation in Vision Science. *Transl Vis Sci Technol* 3, 1 (2014).
21. Vinores, S. A., et al. Blood-retinal barrier breakdown in retinitis pigmentosa: light and electron microscopic immunolocalization. *Histol Histopathol* 10, 913-923 (1995).
22. Kawamura, S. & Tachibanaki, S. Rod and cone photoreceptors: molecular basis of the difference in their physiology. *Comp Biochem Physiol A Mol Integr Physiol* 150, 369-377 (2008).
23. Korenbrot, J. I. Speed, sensitivity, and stability of the light response in rod and cone photoreceptors: facts and models. *Prog Retin Eye Res* 31, 442-466 (2012).
24. Masseck, O. A., et al. Vertebrate cone opsins enable sustained and highly sensitive rapid control of Gi/o signaling in anxiety circuitry. *Neuron* 81, 1263-1273 (2014).
25. Gutierrez, D. V., et al. Optogenetic control of motor coordination by Gi/o protein-coupled vertebrate rhodopsin in cerebellar Purkinje cells. *J Biol Chem* 286, 25848-25858 (2011).
26. Levitz, J., et al. Optical control of metabotropic glutamate receptors. *Nat Neurosci* 16, 507-516 (2013).
27. Friedmann, D., Hoagland, A., Berlin, S. & Isacoff, E. Y. A spinal opsin controls early neural activity and drives a behavioral light response. *Current biology: CB* 25, 69-74 (2015).
28. Fischer, R. M., et al. Co-expression of VAL- and TMT-opsins uncovers ancient photosensory interneurons and motorneurons in the vertebrate brain. *PLoS Biol* 11, e1001585 (2013).
29. Liegertova, M., et al. Corrigendum: Cubozoan genome illuminates functional diversification of opsins and photoreceptor evolution. *Sci Rep* 5, 14396 (2015).
30. Chen, M. H., Kuemmel, C., Birge, R. R. & Knox, B. E. Rapid release of retinal from a cone visual pigment following photoactivation. *Biochemistry* 51, 4117-4125 (2012).
31. Mark, M. D. & Herlitze, S. G-protein mediated gating of inward-rectifier K+ channels. *Eur J Biochem* 267, 5830-5836 (2000).
32. Shevtsova, Z., Malik, J. M., Michel, U., Bahr, M. & Kugler, S. Promoters and serotypes: targeting of adeno-associated virus vectors for gene transfer in the rat central nervous system in vitro and in vivo. *Exp Physiol* 90, 53-59 (2005).
33. Sancho-Pelluz, J., et al. Photoreceptor cell death mechanisms in inherited retinal degeneration. *Molecular neurobiology* 38, 253-269 (2008).
34. Schwartz, E. A. Responses of bipolar cells in the retina of the turtle. *The Journal of physiology* 236, 211-224 (1974).
35. Bourin, M. & Hascoet, M. The mouse light/dark box test. *European journal of pharmacology* 463, 55-65 (2003).
36. Merbs, S. L. & Nathans, J. Photobleaching difference absorption spectra of human cone pigments: quantitative analysis and comparison to other methods. *Photochem Photobiol* 56, 869-881 (1992).
37. Tochitsky, I., et al. Restoring visual function to blind mice with a photoswitch that exploits electrophysiological remodeling of retinal ganglion cells. *Neuron* 81, 800-813 (2014).
38. Bittner, A. K., Jeter, P. & Dagnelie, G. Grating Acuity and Contrast Tests for Clinical Trials of Severe Vision Loss. *Optometry and vision science: official publication of the American Academy of Optometry* 88, 1153-1163 (2011).
39. Wong, A. A. & Brown, R. E. Visual detection, pattern discrimination and visual acuity in 14 strains of mice. *Genes, Brain and Behavior* 5, 389-403 (2006).
40. Pepperberg, D. R. Bleaching desensitization: background and current challenges. *Vision Res* 43, 3011-3019 (2003).
41. Kang Derwent, J. J., Qtaishat, N. M. & Pepperberg, D. R. Excitation and desensitization of mouse rod photoreceptors in vivo following bright adapting light. *The Journal of physiology* 541, 201-218 (2002).
42. Di Lollo, V., Clark, C. D. & Hogben, J. H. Separating visible persistence from retinal afterimages. *Percept Psychophys* 44, 363-368 (1988).
43. Hurley, J. B. Shedding light on adaptation. *J Gen Physiol* 119, 125-128 (2002).
44. Normann, R. A. & Werblin, F. S. Control of retinal sensitivity. I. Light and dark adaptation of vertebrate rods and cones. *J Gen Physiol* 63, 37-61 (1974).
45. Doroudchi, M. M., et al. Virally delivered channelrhodopsin-2 safely and effectively restores visual function in multiple mouse models of blindness. *Mol Ther* 19, 1220-1229 (2011).
46. Caporale, N., et al. LiGluR restores visual responses in rodent models of inherited blindness. *Mol Ther* 19, 1212-1219 (2011).
47. Gaub, B. M., et al. Restoration of visual function by expression of a light-gated mammalian ion channel in retinal ganglion cells or ON-bipolar cells. *Proc Natl Acad Sci USA* 111, E5574-5583 (2014).
48. Sommer, M. E., Hofmann, K. P. & Heck, M. Distinct loops in arrestin differentially regulate ligand binding within the GPCR opsin. *Nat Commun* 3, 995 (2012).
49. Polosukhina, A., et al. Photochemical restoration of visual responses in blind mice. *Neuron* 75, 271-282 (2012).
50. Holladay, J. T. Proper method for calculating average visual acuity. *Journal of refractive surgery* (Thorofare, N. J.: 1995) 13, 388-391 (1997).
51. Broichhagen, J., et al. Orthogonal Optical Control of a G Protein-Coupled Receptor with a SNAP-Tethered Photochromic Ligand. *ACS Cent Sci* 1, 383-393 (2015).
52. Levitz, J., Broichhagen, J., Leippe, P., Konrad, D., Trauner, D. and Isacoff, E. Y. Dual optical control and mechanistic insights into photoswitchable group II and III metabotropic glutamate receptors. *Proc Natl Acad Sci USA* (2017).
53. Roska, B., Molnar, A. & Werblin, F. S. Parallel processing in retinal ganglion cells: how integration of space-time patterns of excitation and inhibition form the spiking output. *Journal of neurophysiology* 95, 3810-3822 (2006).
54. Leinonen H, Tanila H. Vision in laboratory rodents-Tools to measure it and implications for behavioral research. *Behav Brain Res*, (2017).

55. Prusky G T, West P W, Douglas R M. Behavioral assessment of visual acuity in mice and rats. *Vision Res* 40, 2201-2209 (2000).
56. Shi C, et al. Optimization of Optomotor Response-based Visual Function Assessment in Mice. *Sci Rep* 8, 9708 (2018).
57. Berson D M, Dunn F A, Takao M. Phototransduction by retinal ganglion cells that set the circadian clock. *Science* 295, 1070-1073 (2002).
58. Veit J, Hakim R, Jadi M P, Sejnowski T J, Adesnik H. Cortical gamma band synchronization through somatostatin interneurons. *Nat Neurosci* 20, 951-959 (2017).
59. Brainard D H. The psychophysics toolbox. *Spatial Vision* 10, 433-436 (1997).
60. Hill D N, Mehta S B, Kleinfeld D. Quality Metrics to Accompany Spike Sorting of Extracellular Signals. *Journal of Neuroscience* 31, 8699-8705 (2011).
61. Berry M, et al. Restoration of Patterned Vision with an Engineered Photo-Activatable G Protein-Coupled Receptor. *Nat Commun*, (2017).
62. Antunes M, Biala G. The novel object recognition memory: neurobiology, test procedure, and its modifications. *Cognitive Processing* 13, 93-110 (2012).
63. Christmas A J, Maxwell D R. A comparison of the effects of some benzodiazepines and other drugs on aggressive and exploratory behaviour in mice and rats. *Neuropharmacology* 9, 17-29 (1970).
64. Buhot M C, Dubayle D, Malleret G, Javerzat S, Segu L. Exploration, anxiety, and spatial memory in transgenic anophthalmic mice. *Behavioral neuroscience* 115, 455-467 (2001).
65. Cronin T, et al. Efficient transduction and optogenetic stimulation of retinal bipolar cells by a synthetic adeno-associated virus capsid and promoter. *EMBO Molecular Medicine* 6, 1175-1190 (2014).
66. Berry M H, et al. Restoration of patterned vision with an engineered photoactivatable G protein-coupled receptor. *Nat Commun* 8, 1862 (2017).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of restoring or enhancing visual function in an individual having retinal degeneration, the method comprising administering directly to an eye of the individual at least one recombinant expression vector comprising a nucleic acid comprising one or more of: i) a nucleotide sequence encoding a medium wavelength opsin (MW-opsin); ii) a nucleotide sequence encoding a long wavelength opsin (LW-opsin); and iii) a nucleotide sequence encoding a short wavelength opsin (SW-opsin), wherein the one or more of the nucleotide sequence encoding SW-opsin, the nucleotide sequence encoding MW-opsin, and the nucleotide sequence encoding LW-opsin are operably linked to a promoter other than an opsin promoter and are expressed in a retinal cell in the individual, thereby mediating the restoring or the enhancing visual function in the individual, wherein the retinal cell is a retinal ganglion cell, an amacrine cell, a horizontal cell, or a bipolar cell.

2. The method of claim 1, wherein the MW-opsin comprises an amino acid sequence having at least 95% amino acid sequence identity to the amino acid sequence set forth in SEQ ID NO:1; wherein the LW-opsin comprises an amino acid sequence having at least 95% amino acid sequence identity to the amino acid sequence set forth in SEQ ID NO:4, and wherein the SW-opsin comprises an amino acid sequence having at least 95% amino acid sequence identity to the amino acid sequence set forth in SEQ ID NO:5.

3. The method of claim 1, wherein the nucleic acid comprises the nucleotide sequence encoding SW-opsin, wherein the SW-opsin comprises an amino acid sequence having at least 98% amino acid sequence identity to the human SW-opsin amino acid sequence set forth in SEQ ID NO:5 or having at least 98% amino acid sequence identity to the mouse SW-opsin amino acid sequence set forth in SEQ ID NO:6.

4. The method of claim 1, wherein the at least one recombinant expression vector comprises a first nucleic acid and a second nucleic acid, and wherein: i) the first nucleic acid comprises the nucleotide sequence encoding the SW-opsin wherein the SW-opsin comprises an amino acid sequence having at least 95% amino acid sequence identity to the human SW-opsin amino acid sequence set forth in SEQ ID NO:5; and ii) the second nucleic acid comprises the nucleotide sequence encoding the SW-opsin wherein the SW-opsin comprises an amino acid sequence having at least 95% amino acid sequence identity to the mouse SW-opsin amino acid sequence set forth in SEQ ID NO:6.

5. The method of claim 1, wherein said restoring or said enhancing visual function comprises restoring or enhancing patterned vision and image recognition by the individual.

6. The method of claim 5, wherein the image recognition is of a static image or a pattern.

7. The method of claim 5, wherein the image recognition is of a moving image or a pattern.

8. The method of claim 1, wherein said restoring or said enhancing visual function comprises restoring or enhancing image recognition at a light intensity of from about $10^{-4}$ W/cm$^2$ to about 1 W/cm$^2$.

9. The method of claim 1, wherein said restoring or said enhancing visual function comprises restoring or enhancing image recognition at a light intensity that is at least 10-fold lower than the light intensity required to provide for image recognition by an individual expressing a channelrhodopsin polypeptide in a retinal cell.

10. The method of claim 1, wherein said restoring or said enhancing visual function comprises restoring or enhancing kinetics that are at least 2-fold faster than the kinetics conferred on a retinal cell by a rhodopsin polypeptide.

11. The method of claim 1, wherein the at least one recombinant expression vector is a recombinant viral vector.

12. The method of claim 11, wherein the recombinant viral vector is an adeno-associated viral vector, a lentiviral vector, a herpes simplex virus vector, or a retroviral vector.

13. The method of claim 1, wherein the nucleic acid sequence is further operably linked to a transcriptional control element that is functional in the retinal cell.

14. The method of claim 13, wherein the transcriptional control element is a retinal cell-specific promoter.

15. The method of claim 1, wherein the promoter is a synapsin promoter, a CAG promoter, a CMV promoter, a grm6 promoter, a Pleiades promoter, a ChAT promoter, a V-glut promoter, a GAD promoter, a PV promoter, a somatostatin (SST) promoter, a neuropeptide Y (NPY) promoter, a VIP promoter, a rhodopsin kinase promoter, a vitelliform macular dystrophy 2 (VMD2) gene promoter, or an interphotoreceptor retinoid-binding protein (IRBP) gene promoter.

16. The method of claim 1, wherein said administering is via intraocular injection, intravitreal injection, or subretinal injection.

17. The method of claim 1, wherein the individual has an ocular disease selected from retinitis pigmentosa, macular degeneration, retinoschisis, Leber's Congenital Amaurosis, and diabetic retinopathy.

18. The method of claim 1, wherein the individual has experienced retinal detachment or photoreceptor loss due to trauma or head injury.

19. The method of claim 1, wherein the retinal cell is a retinal ganglion cell.

20. The method of claim 1, wherein the at least recombinant expression vector is a recombinant adeno-associated viral vector.

21. The method of claim 1, wherein the individual has retinitis pigmentosa.

22. The method of claim 20, wherein the adeno-associated viral vector is AAV2.

23. The method of claim 1, wherein said administering is via a periocular, an intraocular, an intravitreal, a subconjunctiva, a retrobulbar, a scleral, a sub-retinal, or an intracameral route of administration.

24. The method of claim 1, wherein the promoter is a synapsin promoter.

25. The method of claim 1, wherein the promoter is a CAG promoter.

26. The method of claim 1, wherein the promoter is a V-glut promoter.

* * * * *

SEQUENCE LISTING

<160> NUMBER OF SEQ ID NOS: 11

<210> SEQ ID NO 1
<211> LENGTH: 364
<212> TYPE: PRT
<213> ORGANISM: Homo sapiens

<400> SEQUENCE: 1

Met Ala Gln Gln Trp Ser Leu Gln Arg Leu Ala Gly Arg His Pro Gln
1               5                   10                  15

Asp Ser Tyr Glu Asp Ser Thr Gln Ser Ser Ile Phe Thr Tyr Thr Asn
            20                  25                  30

Ser Asn Ser Thr Arg Gly Pro Phe Glu Gly Pro Asn Tyr His Ile Ala
        35                  40                  45

Pro Arg Trp Val Tyr His Leu Thr Ser Val Trp Met Ile Phe Val Val
    50                  55                  60

Ile Ala Ser Val Phe Thr Asn Gly Leu Val Leu Ala Ala Thr Met Lys
65                  70                  75                  80

Phe Lys Lys Leu Arg His Pro Leu Asn Trp Ile Leu Val Asn Leu Ala
                85                  90                  95

Val Ala Asp Leu Ala Glu Thr Val Ile Ala Ser Thr Ile Ser Val Val
            100                 105                 110

Asn Gln Val Tyr Gly Tyr Phe Val Leu Gly His Pro Met Cys Val Leu
        115                 120                 125

Glu Gly Tyr Thr Val Ser Leu Cys Gly Ile Thr Gly Leu Trp Ser Leu
    130                 135                 140

Ala Ile Ile Ser Trp Glu Arg Trp Met Val Val Cys Lys Pro Phe Gly
145                 150                 155                 160

Asn Val Arg Phe Asp Ala Lys Leu Ala Ile Val Gly Ile Ala Phe Ser
                165                 170                 175

Trp Ile Trp Ala Ala Val Trp Thr Ala Pro Pro Ile Phe Gly Trp Ser
            180                 185                 190

Arg Tyr Trp Pro His Gly Leu Lys Thr Ser Cys Gly Pro Asp Val Phe
        195                 200                 205

Ser Gly Ser Ser Tyr Pro Gly Val Gln Ser Tyr Met Ile Val Leu Met
    210                 215                 220

Val Thr Cys Cys Ile Thr Pro Leu Ser Ile Ile Val Leu Cys Tyr Leu
225                 230                 235                 240

Gln Val Trp Leu Ala Ile Arg Ala Val Ala Lys Gln Gln Lys Glu Ser
                245                 250                 255

Glu Ser Thr Gln Lys Ala Glu Lys Glu Val Thr Arg Met Val Val Val
                260                 265                 270

Met Val Leu Ala Phe Cys Phe Cys Trp Gly Pro Tyr Ala Phe Phe Ala
            275                 280                 285

Cys Phe Ala Ala Ala Asn Pro Gly Tyr Pro Phe His Pro Leu Met Ala
        290                 295                 300

Ala Leu Pro Ala Phe Phe Ala Lys Ser Ala Thr Ile Tyr Asn Pro Val
305                 310                 315                 320

Ile Tyr Val Phe Met Asn Arg Gln Phe Arg Asn Cys Ile Leu Gln Leu
                325                 330                 335

Phe Gly Lys Lys Val Asp Asp Gly Ser Glu Leu Ser Ser Ala Ser Lys
            340                 345                 350

Thr Glu Val Ser Ser Val Ser Val Ser Pro Ala
            355                 360

<210> SEQ ID NO 2
<211> LENGTH: 348
<212> TYPE: PRT
<213> ORGANISM: Homo sapiens

<400> SEQUENCE: 2

Met Asn Gly Thr Glu Gly Pro Asn Phe Tyr Val Pro Phe Ser Asn Ala
1               5                   10                  15

Thr Gly Val Val Arg Ser Pro Phe Glu Tyr Pro Gln Tyr Tyr Leu Ala
                20                  25                  30

Glu Pro Trp Gln Phe Ser Met Leu Ala Ala Tyr Met Phe Leu Leu Ile
            35                  40                  45

Val Leu Gly Phe Pro Ile Asn Phe Leu Thr Leu Tyr Val Thr Val Gln
50                  55                  60

His Lys Lys Leu Arg Thr Pro Leu Asn Tyr Ile Leu Leu Asn Leu Ala
65                  70                  75                  80

Val Ala Asp Leu Phe Met Val Leu Gly Gly Phe Thr Ser Thr Leu Tyr
                85                  90                  95

Thr Ser Leu His Gly Tyr Phe Val Phe Gly Pro Thr Gly Cys Asn Leu
            100                 105                 110

Glu Gly Phe Phe Ala Thr Leu Gly Gly Glu Ile Ala Leu Trp Ser Leu
        115                 120                 125

Val Val Leu Ala Ile Glu Arg Tyr Val Val Val Cys Lys Pro Met Ser
130                 135                 140

Asn Phe Arg Phe Gly Glu Asn His Ala Ile Met Gly Val Ala Phe Thr
145                 150                 155                 160

Trp Val Met Ala Leu Ala Cys Ala Ala Pro Pro Leu Ala Gly Trp Ser
                165                 170                 175

Arg Tyr Ile Pro Glu Gly Leu Gln Cys Ser Cys Gly Ile Asp Tyr Tyr
            180                 185                 190

Thr Leu Lys Pro Glu Val Asn Asn Glu Ser Phe Val Ile Tyr Met Phe
        195                 200                 205

Val Val His Phe Thr Ile Pro Met Ile Ile Ile Phe Phe Cys Tyr Gly

```
            210                 215                 220
Gln Leu Val Phe Thr Val Lys Glu Ala Ala Gln Gln Glu Ser
225                 230                 235                 240

Ala Thr Thr Gln Lys Ala Glu Lys Glu Val Thr Arg Met Val Ile Ile
                245                 250                 255

Met Val Ile Ala Phe Leu Ile Cys Trp Val Pro Tyr Ala Ser Val Ala
                260                 265                 270

Phe Tyr Ile Phe Thr His Gln Gly Ser Asn Phe Gly Pro Ile Phe Met
                275                 280                 285

Thr Ile Pro Ala Phe Phe Ala Lys Ser Ala Ala Ile Tyr Asn Pro Val
                290                 295                 300

Ile Tyr Ile Met Met Asn Lys Gln Phe Arg Asn Cys Met Leu Thr Thr
305                 310                 315                 320

Ile Cys Cys Gly Lys Asn Pro Leu Gly Asp Asp Glu Ala Ser Ala Thr
                325                 330                 335

Val Ser Lys Thr Glu Thr Ser Gln Val Ala Pro Ala
                340                 345

<210> SEQ ID NO 3
<211> LENGTH: 310
<212> TYPE: PRT
<213> ORGANISM: Artificial Sequence
<220> FEATURE:
<223> OTHER INFORMATION: Synthetic sequence

<400> SEQUENCE: 3

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
                20                  25                  30

Gln Cys Tyr Cys Ala Gly Trp Ile Glu Ser Arg Gly Thr Asn Gly Ala
                35                  40                  45

Gln Thr Ala Ser Asn Val Leu Gln Trp Leu Ala Ala Gly Phe Ser Ile
            50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
                100                 105                 110

Gly His Arg Val Gln Trp Leu Arg Tyr Ala Glu Trp Leu Leu Thr Cys
                115                 120                 125

Pro Val Ile Leu Ile His Leu Ser Asn Leu Thr Gly Leu Ser Asn Asp
            130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
                180                 185                 190

Ala Lys Ala Tyr Ile Glu Gly Tyr His Thr Val Pro Lys Gly Arg Cys
                195                 200                 205

Arg Gln Val Val Thr Gly Met Ala Trp Leu Phe Phe Val Ser Trp Gly
            210                 215                 220

Met Phe Pro Ile Leu Phe Ile Leu Gly Pro Glu Gly Phe Gly Val Leu
```

```
                    225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
                260                 265                 270

Glu His Ile Leu Ile His Gly Asp Ile Arg Lys Thr Thr Lys Leu Asn
                275                 280                 285

Ile Gly Gly Thr Glu Ile Glu Val Glu Thr Leu Val Glu Asp Glu Ala
                290                 295                 300

Glu Ala Gly Ala Val Pro
305                 310

<210> SEQ ID NO 4
<211> LENGTH: 364
<212> TYPE: PRT
<213> ORGANISM: Homo sapiens

<400> SEQUENCE: 4

Met Ala Gln Gln Trp Ser Leu Gln Arg Leu Ala Gly Arg His Pro Gln
1               5                   10                  15

Asp Ser Tyr Glu Asp Ser Thr Gln Ser Ser Ile Phe Thr Tyr Thr Asn
                20                  25                  30

Ser Asn Ser Thr Arg Gly Pro Phe Glu Gly Pro Asn Tyr His Ile Ala
            35                  40                  45

Pro Arg Trp Val Tyr His Leu Thr Ser Val Trp Met Ile Phe Val Val
        50                  55                  60

Thr Ala Ser Val Phe Thr Asn Gly Leu Val Leu Ala Ala Thr Met Lys
65                  70                  75                  80

Phe Lys Lys Leu Arg His Pro Leu Asn Trp Ile Leu Val Asn Leu Ala
                85                  90                  95

Val Ala Asp Leu Ala Glu Thr Val Ile Ala Ser Thr Ile Ser Ile Val
                100                 105                 110

Asn Gln Val Ser Gly Tyr Phe Val Leu Gly His Pro Met Cys Val Leu
            115                 120                 125

Glu Gly Tyr Thr Val Ser Leu Cys Gly Ile Thr Gly Leu Trp Ser Leu
130                 135                 140

Ala Ile Ile Ser Trp Glu Arg Trp Met Val Val Cys Lys Pro Phe Gly
145                 150                 155                 160

Asn Val Arg Phe Asp Ala Lys Leu Ala Ile Val Gly Ile Ala Phe Ser
                165                 170                 175

Trp Ile Trp Ala Ala Val Trp Thr Ala Pro Pro Ile Phe Gly Trp Ser
                180                 185                 190

Arg Tyr Trp Pro His Gly Leu Lys Thr Ser Cys Gly Pro Asp Val Phe
            195                 200                 205

Ser Gly Ser Ser Tyr Pro Gly Val Gln Ser Tyr Met Ile Val Leu Met
        210                 215                 220

Val Thr Cys Cys Ile Ile Pro Leu Ala Ile Ile Met Leu Cys Tyr Leu
225                 230                 235                 240

Gln Val Trp Leu Ala Ile Arg Ala Val Ala Lys Gln Gln Lys Glu Ser
                245                 250                 255

Glu Ser Thr Gln Lys Ala Glu Lys Glu Val Thr Arg Met Val Val Val
                260                 265                 270

Met Ile Phe Ala Tyr Cys Val Cys Trp Gly Pro Tyr Thr Phe Phe Ala
            275                 280                 285
```

```
Cys Phe Ala Ala Ala Asn Pro Gly Tyr Ala Phe His Pro Leu Met Ala
    290                 295                 300

Ala Leu Pro Ala Tyr Phe Ala Lys Ser Ala Thr Ile Tyr Asn Pro Val
305                 310                 315                 320

Ile Tyr Val Phe Met Asn Arg Gln Phe Arg Asn Cys Ile Leu Gln Leu
                325                 330                 335

Phe Gly Lys Lys Val Asp Asp Gly Ser Glu Leu Ser Ser Ala Ser Lys
                340                 345                 350

Thr Glu Val Ser Ser Val Ser Ser Val Ser Pro Ala
            355                 360

<210> SEQ ID NO 5
<211> LENGTH: 348
<212> TYPE: PRT
<213> ORGANISM: Homo sapiens

<400> SEQUENCE: 5

Met Arg Lys Met Ser Glu Glu Phe Tyr Leu Phe Lys Asn Ile Ser
1               5                   10                  15

Ser Val Gly Pro Trp Asp Gly Pro Gln Tyr His Ile Ala Pro Val Trp
                20                  25                  30

Ala Phe Tyr Leu Gln Ala Ala Phe Met Gly Thr Val Phe Leu Ile Gly
                35                  40                  45

Phe Pro Leu Asn Ala Met Val Leu Val Ala Thr Leu Arg Tyr Lys Lys
    50                  55                  60

Leu Arg Gln Pro Leu Asn Tyr Ile Leu Val Asn Val Ser Phe Gly Gly
65                  70                  75                  80

Phe Leu Leu Cys Ile Phe Ser Val Phe Pro Val Phe Val Ala Ser Cys
                85                  90                  95

Asn Gly Tyr Phe Val Phe Gly Arg His Val Cys Ala Leu Glu Gly Phe
                100                 105                 110

Leu Gly Thr Val Ala Gly Leu Val Thr Gly Trp Ser Leu Ala Phe Leu
            115                 120                 125

Ala Phe Glu Arg Tyr Ile Val Ile Cys Lys Pro Phe Gly Asn Phe Arg
    130                 135                 140

Phe Ser Ser Lys His Ala Leu Thr Val Val Leu Ala Thr Trp Thr Ile
145                 150                 155                 160

Gly Ile Gly Val Ser Ile Pro Pro Phe Phe Gly Trp Ser Arg Phe Ile
                165                 170                 175

Pro Glu Gly Leu Gln Cys Ser Cys Gly Pro Asp Trp Tyr Thr Val Gly
            180                 185                 190

Thr Lys Tyr Arg Ser Glu Ser Tyr Thr Trp Phe Leu Phe Ile Phe Cys
        195                 200                 205

Phe Ile Val Pro Leu Ser Leu Ile Cys Phe Ser Tyr Thr Gln Leu Leu
    210                 215                 220

Arg Ala Leu Lys Ala Val Ala Ala Gln Gln Gln Glu Ser Ala Thr Thr
225                 230                 235                 240

Gln Lys Ala Glu Arg Glu Val Ser Arg Met Val Val Val Met Val Gly
                245                 250                 255

Ser Phe Cys Val Cys Tyr Val Pro Tyr Ala Ala Phe Ala Met Tyr Met
                260                 265                 270

Val Asn Asn Arg Asn His Gly Leu Asp Leu Arg Leu Val Thr Ile Pro
            275                 280                 285

Ser Phe Phe Ser Lys Ser Ala Cys Ile Tyr Asn Pro Ile Ile Tyr Cys
    290                 295                 300
```

Phe Met Asn Lys Gln Phe Gln Ala Cys Ile Met Lys Met Val Cys Gly
305                 310                 315                 320

Lys Ala Met Thr Asp Glu Ser Asp Thr Cys Ser Ser Gln Lys Thr Glu
            325                 330                 335

Val Ser Thr Val Ser Ser Thr Gln Val Gly Pro Asn
            340                 345

<210> SEQ ID NO 6
<211> LENGTH: 346
<212> TYPE: PRT
<213> ORGANISM: Mus Musculus

<400> SEQUENCE: 6

Met Ser Gly Glu Asp Asp Phe Tyr Leu Phe Gln Asn Ile Ser Ser Val
1               5                   10                  15

Gly Pro Trp Asp Gly Pro Gln Tyr His Leu Ala Pro Val Trp Ala Phe
            20                  25                  30

Arg Leu Gln Ala Ala Phe Met Gly Phe Val Phe Val Gly Thr Pro
            35                  40                  45

Leu Asn Ala Ile Val Leu Val Ala Thr Leu His Tyr Lys Lys Leu Arg
        50                  55                  60

Gln Pro Leu Asn Tyr Ile Leu Val Asn Val Ser Leu Gly Gly Phe Leu
65                  70                  75                  80

Phe Cys Ile Phe Ser Val Phe Thr Val Phe Ile Ala Ser Cys His Gly
                85                  90                  95

Tyr Phe Leu Phe Gly Arg His Val Cys Ala Leu Glu Ala Phe Leu Gly
            100                 105                 110

Ser Val Ala Gly Leu Val Thr Gly Trp Ser Leu Ala Phe Leu Ala Phe
        115                 120                 125

Glu Arg Tyr Val Val Ile Cys Lys Pro Phe Gly Ser Ile Arg Phe Asn
130                 135                 140

Ser Lys His Ala Leu Met Val Val Leu Ala Thr Trp Ile Ile Gly Ile
145                 150                 155                 160

Gly Val Ser Ile Pro Pro Phe Phe Gly Trp Ser Arg Phe Ile Pro Glu
                165                 170                 175

Gly Leu Gln Cys Ser Cys Gly Pro Asp Trp Tyr Thr Val Gly Thr Lys
            180                 185                 190

Tyr Arg Ser Glu Tyr Tyr Thr Trp Phe Leu Phe Ile Phe Cys Phe Ile
        195                 200                 205

Ile Pro Leu Ser Leu Ile Cys Phe Ser Tyr Ser Gln Leu Leu Arg Thr
210                 215                 220

Leu Arg Ala Val Ala Ala Gln Gln Gln Glu Ser Ala Thr Thr Gln Lys
225                 230                 235                 240

Ala Glu Arg Glu Val Ser His Met Val Val Val Met Val Gly Ser Phe
                245                 250                 255

Cys Leu Cys Tyr Val Pro Tyr Ala Ala Leu Ala Met Tyr Met Val Asn
            260                 265                 270

Asn Arg Asn His Gly Leu Asp Leu Arg Leu Val Thr Ile Pro Ala Phe
        275                 280                 285

Phe Ser Lys Ser Ser Cys Val Tyr Asn Pro Ile Ile Tyr Cys Phe Met
290                 295                 300

Asn Lys Gln Phe Arg Ala Cys Ile Leu Glu Met Val Cys Arg Lys Pro
305                 310                 315                 320

Met Ala Asp Glu Ser Asp Val Ser Gly Ser Gln Lys Thr Glu Val Ser

Thr Val Ser Ser Ser Lys Val Gly Pro His
            340                 345

<210> SEQ ID NO 7
<211> LENGTH: 343
<212> TYPE: PRT
<213> ORGANISM: Artificial Sequence
<220> FEATURE:
<223> OTHER INFORMATION: Synthetic sequence

<400> SEQUENCE: 7

Glu Asp Asp Phe Tyr Leu Phe Gln Asn Ile Ser Ser Val Gly Pro Trp
1               5                   10                  15

Asp Gly Pro Gln Tyr His Leu Ala Pro Val Trp Ala Phe Tyr Leu Gln
            20                  25                  30

Ala Ala Phe Met Gly Thr Val Phe Leu Ile Gly Phe Pro Leu Asn Ala
        35                  40                  45

Met Val Leu Val Ala Thr Leu His Tyr Lys Lys Leu Arg Gln Pro Leu
    50                  55                  60

Asn Tyr Ile Leu Val Asn Val Ser Phe Gly Gly Phe Leu Leu Cys Ile
65                  70                  75                  80

Phe Ser Val Phe Pro Val Phe Val Ala Ser Cys Asn Gly Tyr Phe Val
                85                  90                  95

Phe Gly Arg His Val Cys Ala Leu Glu Gly Phe Leu Gly Thr Val Ala
            100                 105                 110

Gly Leu Val Thr Gly Trp Ser Leu Ala Phe Leu Ala Phe Glu Arg Tyr
        115                 120                 125

Val Val Ile Cys Lys Pro Phe Gly Ser Ile Arg Phe Asn Ser Lys His
    130                 135                 140

Ala Leu Thr Val Val Leu Ala Thr Trp Thr Ile Gly Ile Gly Val Ser
145                 150                 155                 160

Ile Pro Pro Phe Phe Gly Trp Ser Arg Phe Ile Pro Glu Gly Leu Gln
                165                 170                 175

Cys Ser Cys Gly Pro Asp Trp Tyr Thr Val Gly Thr Lys Tyr Arg Ser
            180                 185                 190

Glu Ser Tyr Thr Trp Phe Leu Phe Ile Phe Cys Phe Ile Val Pro Leu
        195                 200                 205

Ser Leu Ile Cys Phe Ser Tyr Thr Gln Leu Leu Arg Ala Leu Arg Ala
    210                 215                 220

Val Ala Ala Gln Gln Gln Glu Ser Ala Thr Thr Gln Lys Ala Glu Arg
225                 230                 235                 240

Glu Val Ser His Met Val Val Met Val Gly Ser Phe Cys Val Cys
                245                 250                 255

Tyr Val Pro Tyr Ala Ala Phe Ala Met Tyr Met Val Asn Asn Arg Asn
            260                 265                 270

His Gly Leu Asp Leu Arg Leu Val Thr Ile Pro Ser Phe Phe Ser Lys
        275                 280                 285

Ser Ala Cys Ile Tyr Asn Pro Ile Ile Tyr Cys Phe Met Asn Lys Gln
    290                 295                 300

Phe Arg Ala Cys Ile Leu Glu Met Val Cys Arg Lys Pro Met Ala Asp
305                 310                 315                 320

Glu Ser Asp Val Ser Gly Ser Gln Lys Thr Glu Val Ser Thr Val Ser
                325                 330                 335

Ser Ser Lys Val Gly Pro His

340

<210> SEQ ID NO 8
<211> LENGTH: 359
<212> TYPE: PRT
<213> ORGANISM: Mus Musculus

<400> SEQUENCE: 8

Met Ala Gln Arg Leu Thr Gly Glu Gln Thr Leu Asp His Tyr Glu Asp
1               5                   10                  15

Ser Thr His Ala Ser Ile Phe Thr Tyr Thr Asn Ser Asn Ser Thr Lys
            20                  25                  30

Gly Pro Phe Glu Gly Pro Asn Tyr His Ile Ala Pro Arg Trp Val Tyr
        35                  40                  45

His Leu Thr Ser Thr Trp Met Ile Leu Val Val Ala Ser Val Phe
    50                  55                  60

Thr Asn Gly Leu Val Leu Ala Ala Thr Met Arg Phe Lys Lys Leu Arg
65              70                  75                  80

His Pro Leu Asn Trp Ile Leu Val Asn Leu Ala Val Ala Asp Leu Ala
                85                  90                  95

Glu Thr Ile Ile Ala Ser Thr Ile Ser Val Val Asn Gln Ile Tyr Gly
            100                 105                 110

Tyr Phe Val Leu Gly His Pro Leu Cys Val Ile Glu Gly Tyr Ile Val
        115                 120                 125

Ser Leu Cys Gly Ile Thr Gly Leu Trp Ser Leu Ala Ile Ile Ser Trp
    130                 135                 140

Glu Arg Trp Leu Val Val Cys Lys Pro Phe Gly Asn Val Arg Phe Asp
145                 150                 155                 160

Ala Lys Leu Ala Thr Val Gly Ile Val Phe Ser Trp Val Trp Ala Ala
                165                 170                 175

Ile Trp Thr Ala Pro Pro Ile Phe Gly Trp Ser Arg Tyr Trp Pro Tyr
            180                 185                 190

Gly Leu Lys Thr Ser Cys Gly Pro Asp Val Phe Ser Gly Thr Ser Tyr
        195                 200                 205

Pro Gly Val Gln Ser Tyr Met Met Val Leu Met Val Thr Cys Cys Ile
    210                 215                 220

Phe Pro Leu Ser Ile Ile Val Leu Cys Tyr Leu Gln Val Trp Leu Ala
225                 230                 235                 240

Ile Arg Ala Val Ala Lys Gln Gln Lys Glu Ser Glu Ser Thr Gln Lys
                245                 250                 255

Ala Glu Lys Glu Val Thr Arg Met Val Val Val Met Val Phe Ala Tyr
            260                 265                 270

Cys Leu Cys Trp Gly Pro Tyr Thr Phe Phe Ala Cys Phe Ala Thr Ala
        275                 280                 285

His Pro Gly Tyr Ala Phe His Pro Leu Val Ala Ser Leu Pro Ser Tyr
    290                 295                 300

Phe Ala Lys Ser Ala Thr Ile Tyr Asn Pro Ile Ile Tyr Val Phe Met
305                 310                 315                 320

Asn Arg Gln Phe Arg Asn Cys Ile Leu His Leu Phe Gly Lys Lys Val
                325                 330                 335

Asp Asp Ser Ser Glu Leu Ser Ser Thr Ser Lys Thr Glu Val Ser Ser
            340                 345                 350

Val Ser Val Ser Pro Ala
        355

<210> SEQ ID NO 9
<211> LENGTH: 348
<212> TYPE: PRT
<213> ORGANISM: Mus Musculus

<400> SEQUENCE: 9

Met Asn Gly Thr Glu Gly Pro Asn Phe Tyr Val Pro Phe Ser Asn Val
1               5                   10                  15

Thr Gly Val Val Arg Ser Pro Phe Glu Gln Pro Gln Tyr Tyr Leu Ala
            20                  25                  30

Glu Pro Trp Gln Phe Ser Met Leu Ala Ala Tyr Met Phe Leu Leu Ile
        35                  40                  45

Val Leu Gly Phe Pro Ile Asn Phe Leu Thr Leu Tyr Val Thr Val Gln
50                  55                  60

His Lys Lys Leu Arg Thr Pro Leu Asn Tyr Ile Leu Leu Asn Leu Ala
65                  70                  75                  80

Val Ala Asp Leu Phe Met Val Phe Gly Gly Phe Thr Thr Thr Leu Tyr
                85                  90                  95

Thr Ser Leu His Gly Tyr Phe Val Phe Gly Pro Thr Gly Cys Asn Leu
            100                 105                 110

Glu Gly Phe Phe Ala Thr Leu Gly Gly Glu Ile Ala Leu Trp Ser Leu
        115                 120                 125

Val Val Leu Ala Ile Glu Arg Tyr Val Val Cys Lys Pro Met Ser
130                 135                 140

Asn Phe Arg Phe Gly Glu Asn His Ala Ile Met Gly Val Val Phe Thr
145                 150                 155                 160

Trp Ile Met Ala Leu Ala Cys Ala Ala Pro Pro Leu Val Gly Trp Ser
                165                 170                 175

Arg Tyr Ile Pro Glu Gly Met Gln Cys Ser Cys Gly Ile Asp Tyr Tyr
            180                 185                 190

Thr Leu Lys Pro Glu Val Asn Asn Glu Ser Phe Val Ile Tyr Met Phe
        195                 200                 205

Val Val His Phe Thr Ile Pro Met Ile Val Ile Phe Phe Cys Tyr Gly
210                 215                 220

Gln Leu Val Phe Thr Val Lys Glu Ala Ala Ala Gln Gln Gln Glu Ser
225                 230                 235                 240

Ala Thr Thr Gln Lys Ala Glu Lys Glu Val Thr Arg Met Val Ile Ile
                245                 250                 255

Met Val Ile Phe Phe Leu Ile Cys Trp Leu Pro Tyr Ala Ser Val Ala
            260                 265                 270

Phe Tyr Ile Phe Thr His Gln Gly Ser Asn Phe Gly Pro Ile Phe Met
        275                 280                 285

Thr Leu Pro Ala Phe Phe Ala Lys Ser Ser Ser Ile Tyr Asn Pro Val
290                 295                 300

Ile Tyr Ile Met Leu Asn Lys Gln Phe Arg Asn Cys Met Leu Thr Thr
305                 310                 315                 320

Leu Cys Cys Gly Lys Asn Pro Leu Gly Asp Asp Ala Ser Ala Thr
                325                 330                 335

Ala Ser Lys Thr Glu Thr Ser Gln Val Ala Pro Ala
            340                 345

<210> SEQ ID NO 10
<211> LENGTH: 736
<212> TYPE: PRT
<213> ORGANISM: Artificial Sequence
<220> FEATURE:
<223> OTHER INFORMATION: Synthetic sequence

<400> SEQUENCE: 10

```
Met Ala Ala Asp Gly Tyr Leu Pro Asp Trp Leu Glu Asp Asn Leu Ser
1               5                   10                  15
Glu Gly Ile Arg Glu Trp Trp Asp Leu Lys Pro Gly Ala Pro Lys Pro
            20                  25                  30
Lys Ala Asn Gln Gln Lys Gln Asp Asp Gly Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Ala Ala Asp Ala Ala Leu Glu His Asp Lys Ala Tyr Asp
65                  70                  75                  80
Gln Gln Leu Lys Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
        115                 120                 125
Phe Gly Leu Val Glu Glu Gly Ala Lys Thr Ala Pro Gly Lys Lys Arg
    130                 135                 140
Pro Val Glu Gln Ser Pro Gln Glu Pro Asp Ser Ser Gly Ile Gly
145                 150                 155                 160
Lys Thr Gly Gln Gln Pro Ala Lys Lys Arg Leu Asn Phe Gly Gln Thr
                165                 170                 175
Gly Asp Ser Glu Ser Val Pro Asp Pro Gln Pro Leu Gly Glu Pro Pro
            180                 185                 190
Ala Thr Pro Ala Ala Val Gly Pro Thr Thr Met Ala Ser Gly Gly Gly
        195                 200                 205
Ala Pro Met Ala Asp Asn Asn Glu Gly Ala Asp Gly Val Gly Asn Ala
    210                 215                 220
Ser Gly Asn Trp His Cys Asp Ser Thr Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Ala Ser Thr Gly Ala Ser Asn Asp Asn His
            260                 265                 270
Tyr Phe Gly Tyr Ser Thr Pro Trp Gly Tyr Phe Asp Phe Asn Arg Phe
        275                 280                 285
His Cys His Phe Ser Pro Arg Asp Trp Gln Arg Leu Ile Asn Asn Asn
    290                 295                 300
Trp Gly Phe Arg Pro Lys Arg Leu Asn Phe Lys Leu Phe Asn Ile Gln
305                 310                 315                 320
Val Lys Glu Val Thr Thr Asn Asp Gly Val Thr Thr Ile Ala Asn Asn
                325                 330                 335
Leu Thr Ser Thr Val Gln Val Phe Ser Asp Ser Glu Tyr Gln Leu Pro
            340                 345                 350
Tyr Val Leu Gly Ser Ala His Gln Gly Cys Leu Pro Pro Phe Pro Ala
        355                 360                 365
Asp Val Phe Met Ile Pro Gln Tyr Gly Tyr Leu Thr Leu Asn Asn Gly
    370                 375                 380
Ser Gln Ala Val Gly Arg Ser Ser Phe Tyr Cys Leu Glu Tyr Phe Pro
385                 390                 395                 400
```

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Lys Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 11
<211> LENGTH: 736
<212> TYPE: PRT
<213> ORGANISM: Artificial Sequence
<220> FEATURE:
<223> OTHER INFORMATION: Synthetic sequence

<400> SEQUENCE: 11

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

-continued

Lys Ala Asn Gln Gln Lys Gln Asp Asp Gly Arg Gly Leu Val Leu Pro
          35                  40                  45

Gly Tyr Lys Tyr Leu Gly Pro Phe Asn Gly Leu Asp Lys Gly Glu Pro
 50                  55                  60

Val Asn Ala Ala Asp Ala Ala Leu Glu His Asp Lys Ala Tyr Asp
 65              70              75                  80

Gln Gln Leu Lys Ala Gly Asp Asn Pro Tyr Leu Arg Tyr Asn His Ala
              85                  90                  95

Asp Ala Glu Phe Gln Glu Arg Leu Gln Glu Asp Thr Ser Phe Gly Gly
             100                 105                 110

Asn Leu Gly Arg Ala Val Phe Gln Ala Lys Lys Arg Val Leu Glu Pro
         115                 120                 125

Phe Gly Leu Val Glu Glu Gly Ala Lys Thr Ala Pro Gly Lys Lys Arg
 130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                 165                 170                 175

Gly Asp Ser Glu Ser Val Pro Asp Pro Gln Pro Leu Gly Glu Pro Pro
             180                 185                 190

Ala Thr Pro Ala Ala Val Gly Pro Thr Thr Met Ala Ser Gly Gly Gly
         195                 200                 205

Ala Pro Met Ala Asp Asn Asn Glu Gly Ala Asp Gly Val Gly Asn Ala
     210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                 245                 250                 255

Tyr Lys Gln Ile Ser Ser Ala Ser Thr Gly Ala Ser Asn Asp Asn His
             260                 265                 270

Tyr Phe Gly Tyr Ser Thr Pro Trp Gly Tyr Phe Asp Phe Asn Arg Phe
         275                 280                 285

His Cys His Phe Ser Pro Arg Asp Trp Gln Arg Leu Ile Asn Asn Asn
     290                 295                 300

Trp Gly Phe Arg Pro Lys Arg Leu Asn Phe Lys Leu Phe Asn Val Gln
305                 310                 315                 320

Val Lys Glu Val Thr Thr Asn Asp Gly Val Thr Thr Ile Ala Asn Asn
                 325                 330                 335

Leu Thr Ser Thr Val Gln Val Phe Ser Asp Ser Glu Tyr Gln Leu Pro
             340                 345                 350

Tyr Val Leu Gly Ser Ala His Gln Gly Cys Leu Pro Pro Phe Pro Ala
         355                 360                 365

Asp Val Phe Met Ile Pro Gln Tyr Gly Tyr Leu Thr Leu Asn Asn Gly
     370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                 405                 410                 415

Glu Asp Val Pro Phe His Ser Ser Tyr Ala His Ser Gln Ser Leu Asp
             420                 425                 430

Arg Leu Met Asn Pro Leu Ile Asp Gln Tyr Leu Tyr Tyr Leu Asn Arg
         435                 440                 445

-continued

```
Thr Gln Asp Gln Ser Gly Ser Ala Gln Asn Lys Asp Leu Leu Phe Ser
    450                 455                 460
Arg Gly Ser Pro Ala Gly Met Ser Val Gln Pro Lys Asn Trp Leu Pro
465                 470                 475                 480
Gly Pro Cys Tyr Arg Gln Gln Arg Val Ser Lys Thr Lys Thr Asp Asn
                485                 490                 495
Asn Asn Ser Asn Phe Thr Trp Thr Gly Ala Ser Lys Tyr Asn Leu Asn
            500                 505                 510
Gly Arg Glu Ser Ile Ile Asn Pro Gly Thr Ala Met Ala Ser His Lys
            515                 520                 525
Asp Asp Lys Asn Lys Phe Phe Pro Met Ser Gly Val Met Ile Phe Gly
    530                 535                 540
Lys Glu Ser Ala Gly Ala Ser Asn Thr Ala Leu Asp Asn Val Met Ile
545                 550                 555                 560
Thr Asp Glu Glu Glu Ile Lys Ala Thr Asn Pro Val Ala Thr Glu Arg
                565                 570                 575
Phe Gly Thr Val Ala Val Asn Leu Gln Ser Ser Ser Thr Asp Pro Ala
            580                 585                 590
Thr Gly Asp Val His Val Met Gly Ala Leu Pro Gly Met Val Trp Gln
            595                 600                 605
Asp Arg Asp Val Tyr Leu Gln Gly Pro Ile Trp Ala Lys Ile Pro His
    610                 615                 620
Thr Asp Gly His Phe His Pro Ser Pro Leu Met Gly Gly Phe Gly Leu
625                 630                 635                 640
Lys Asn Pro Pro Pro Gln Ile Leu Ile Lys Asn Thr Pro Val Pro Ala
                645                 650                 655
Asn Pro Pro Ala Glu Phe Ser Ala Thr Lys Phe Ala Ser Phe Ile Thr
            660                 665                 670
Gln Tyr Ser Thr Gly Gln Val Ser Val Glu Ile Glu Trp Glu Leu Gln
            675                 680                 685
Lys Glu Asn Ser Lys Arg Trp Asn Pro Glu Val Gln Tyr Thr Ser Asn
    690                 695                 700
Tyr Ala Lys Ser Ala Asn Val Asp Phe Thr Val Asp Asn Asn Gly Leu
705                 710                 715                 720
Tyr Thr Glu Pro Arg Pro Ile Gly Thr Arg Tyr Leu Thr Arg Pro Leu
                725                 730                 735
```